(12) United States Patent
Toji

(10) Patent No.: US 10,856,849 B2
(45) Date of Patent: Dec. 8, 2020

(54) ULTRASOUND DIAGNOSTIC DEVICE AND ULTRASOUND DIAGNOSTIC DEVICE CONTROL METHOD

(71) Applicant: Konica Minolta, Inc., Tokyo (JP)

(72) Inventor: Bumpei Toji, Hashima (JP)

(73) Assignee: KONICA MINOLTA, INC., Tokyo (JP)

( * ) Notice: Subject to any disclaimer, the term of this patent is extended or adjusted under 35 U.S.C. 154(b) by 446 days.

(21) Appl. No.: 15/615,126

(22) Filed: Jun. 6, 2017

(65) Prior Publication Data

US 2017/0360408 A1 Dec. 21, 2017

(30) Foreign Application Priority Data

Jun. 16, 2016 (JP) .................. 2016-120168

(51) Int. Cl.
*A61B 8/00* (2006.01)
*A61B 8/08* (2006.01)
(Continued)

(52) U.S. Cl.
CPC .............. *A61B 8/485* (2013.01); *A61B 8/469* (2013.01); *A61B 8/5207* (2013.01);
(Continued)

(58) Field of Classification Search
CPC ....... A61B 8/485; A61B 8/469; A61B 8/5207; G01S 7/52017; G01S 15/8906
See application file for complete search history.

(56) References Cited

U.S. PATENT DOCUMENTS 4,913,157 A * 4/1990 Pratt, Jr. .............. A61B 8/0875
600/449
7,252,004 B2 8/2007 Fink et al.
(Continued)

FOREIGN PATENT DOCUMENTS

JP 2014503065 A 2/2014
JP 2015092938 A 5/2015

OTHER PUBLICATIONS

Wang, "Shear Wave Imaging Using Acoustic Radiation Force", Department of Biomedical Engineering, Duke University (Year: 2013).*
(Continued)

*Primary Examiner* — Joanne M Hoffman
(74) *Attorney, Agent, or Firm* — Lucas & Mercanti, LLP

(57) ABSTRACT

An ultrasound diagnostic device includes a propagation information estimator that evaluates reliability of wavefront arrival time data in the wavefront arrival time frame data and, for reliability nonconformance wavefront arrival time data in the wavefront arrival time frame data that does not satisfy a predefined condition, generates compensated wavefront arrival time data by interpolation based on wavefront arrival time data that does satisfy the predefined condition, replaces the reliability nonconformance wavefront arrival time data with the compensated wavefront arrival time data, and generates compensated wavefront arrival time frame data; and an elastic modulus calculator that calculates shear wave propagation speed and/or elastic modulus frame data in the region of interest, based on the compensated wavefront arrival time frame data.

10 Claims, 27 Drawing Sheets

(51) Int. Cl.
*G01S 7/52* (2006.01)
*G01S 15/89* (2006.01)
*G06T 7/00* (2017.01)

(52) U.S. Cl.
CPC ...... *G01S 7/52017* (2013.01); *G01S 7/52022* (2013.01); *G01S 7/52042* (2013.01); *G01S 7/52077* (2013.01); *G01S 15/8906* (2013.01); *A61B 8/085* (2013.01); *G01S 7/52071* (2013.01); *G06T 7/0012* (2013.01)

(56) References Cited

U.S. PATENT DOCUMENTS

| | | | | |
|---|---|---|---|---|
| 7,374,538 | B2 * | 5/2008 | Nightingale | A61B 5/0053 600/443 |
| 8,494,791 | B2 * | 7/2013 | Hazard | A61B 8/485 382/131 |
| 8,532,430 | B2 * | 9/2013 | Hazard | A61B 8/485 382/103 |
| 8,758,248 | B2 * | 6/2014 | Lin | G01S 7/52022 600/438 |
| 9,237,878 | B2 * | 1/2016 | Chen | A61B 8/085 |
| 9,332,962 | B2 * | 5/2016 | Kim | A61B 8/485 |
| 10,324,065 | B2 * | 6/2019 | Lee | G01N 29/04 |
| 10,368,843 | B2 * | 8/2019 | Peterson | A61B 8/14 |
| 2006/0052699 | A1 * | 3/2006 | Angelsen | A61B 8/14 600/437 |
| 2009/0056453 | A1 * | 3/2009 | McAleavey | A61B 8/08 73/597 |
| 2011/0066030 | A1 * | 3/2011 | Yao | A61B 8/485 600/438 |
| 2012/0065507 | A1 * | 3/2012 | Brunke | A61B 8/12 600/442 |
| 2012/0116220 | A1 * | 5/2012 | Burcher | A61B 5/0048 600/438 |
| 2012/0123262 | A1 * | 5/2012 | Xie | A61B 5/0048 600/438 |
| 2013/0296698 | A1 * | 11/2013 | Fraser | A61B 8/4488 600/438 |
| 2014/0046173 | A1 * | 2/2014 | Greenleaf | G01N 21/17 600/411 |
| 2014/0296709 | A1 * | 10/2014 | Fatemi | A61B 8/0858 600/438 |
| 2015/0141821 | A1 * | 5/2015 | Yoshikawa | A61B 8/5207 600/438 |
| 2015/0216507 | A1 * | 8/2015 | Greenleaf | A61B 8/4494 600/438 |
| 2016/0143622 | A1 * | 5/2016 | Xie | A61B 8/4245 600/424 |
| 2016/0262706 | A1 * | 9/2016 | Zhao | A61B 8/485 |
| 2016/0367223 | A1 * | 12/2016 | Honjo | G01S 7/52088 |
| 2017/0042504 | A1 * | 2/2017 | Rich | A61B 8/04 |
| 2017/0055956 | A1 * | 3/2017 | Osumi | A61B 8/5246 |
| 2017/0079620 | A1 * | 3/2017 | Xie | A61B 8/485 |
| 2017/0086795 | A1 * | 3/2017 | Kanayama | A61B 8/485 |
| 2017/0156700 | A1 * | 6/2017 | Honjo | A61B 8/485 |
| 2018/0156902 | A1 * | 6/2018 | McGough | G01S 7/52052 |
| 2018/0168552 | A1 * | 6/2018 | Shi | A61B 18/1477 |
| 2018/0296189 | A1 * | 10/2018 | Hollender | G01S 7/52042 |
| 2018/0296191 | A1 * | 10/2018 | Mellema | A61B 8/485 |
| 2019/0231320 | A1 * | 8/2019 | Clark | A61B 8/14 |

OTHER PUBLICATIONS

"Interpolation and Curve Fitting", Chapter 6, ECE 1010 ECE Problem Solving I (Year: 2015).*

Doherty, "Acoustic Radiation Force Elasticity Imaging in Diagnostic Ultrasound", IEEE Trans Ultrason Ferroelectr Freq Control (Year: 2013).*

Matthew Graham (JE) Fourth-year undergraduate project, "Measuring Tissue Stiffness Using Ultrasound" (Year: 2012).*

* cited by examiner

ULTRASOUND DIAGNOSTIC DEVICE AND ULTRASOUND DIAGNOSTIC DEVICE CONTROL METHOD

This application is based on and claims the priority of Japanese Patent Application No. 2016-120168 filed on Jun. 16, 2016 in Japan, the contents of which are hereby incorporated by reference.

BACKGROUND OF THE INVENTION

(1) Field of the Invention

The present disclosure relates to ultrasound diagnostic devices and ultrasound diagnostic device control methods, and in particular to tissue elastic modulus measurement by using shear waves.

(2) Description of the Related Art

An ultrasound diagnostic device is a medical examination device that transmits ultrasound from transducers that constitute part of an ultrasound probe to the inside of a subject, receives ultrasound reflected waves (echoes) caused by a difference in acoustic impedance of tissue in the subject, and generates and displays an ultrasound tomographic image showing structure of internal tissue of the subject based on electric signals obtained.

In recent years, tissue elastic modulus measurement applying this ultrasound diagnostic technique (shear wave speed measurement (SWSM) hereinafter "ultrasound elastic modulus measurement") is being widely used for examination. This can non-invasively and easily measure hardness of a tumor mass found in organs and body tissues, and is therefore useful in investing tumor hardness in cancer screening tests and evaluating hepatic fibrosis in examination of liver disease.

In such ultrasound elastic modulus measurement, a region of interest (ROI) is determined in a subject, and a push wave (converged ultrasound wave or acoustic radiation force impulse (ARFI)) is transmitted to a specific site in the subject by converging ultrasound from a plurality of transducers, after which ultrasound waves for detection (hereinafter, "detection waves") are transmitted and reflected waves are received multiple times. It is thereby possible to calculate propagation speed of a shear wave generated by acoustic radiation force of the push wave by conducting propagation analysis of the shear wave, which represents elastic modulus of tissue, in order to display distribution of tissue elasticity as an elasticity image, for example (for examples, see U.S. Pat. Nos. 7,252,004 and 7,374,538).

SUMMARY OF THE INVENTION

Problems to be Solved by the Invention

In connection with examination by ultrasound elastic modulus measurement, there is a demand to facilitate confirmation of fine changes in a lesion by increasing signal to noise (S/N) ratio of signals for elastic image acquisition, in order to improve image quality of the elasticity image.

However, in cases such as a region in which it is difficult to obtain a reflected wave in tissue of a subject, and signal intensity of a detected acoustic line signal is minute, accuracy of detection is low, and detection of tissue displacement by a shear wave from the acoustic line signal at at least a predefined accuracy is difficult. Further, in cases in which there is a hard part in tissue of a subject, and an absolute value of displacement detected is minute, accuracy of detection is low, and calculation of a wave front of a shear wave from the displacement at at least a predefined accuracy is difficult. As a result, in a generated elasticity image, in image regions corresponding to hard portions of tissue that are supposed to be displayed as a high elastic modulus, image omissions may occur due to elastic modulus not being calculated.

The present disclosure is made in view of the above problems, and, in ultrasound elastic modulus measurement, an aim is to suppress image omission in an elasticity image in a nonconforming region where reliability of measured wavefront arrival time data is low.

Means for Solving the Problems

An ultrasound diagnostic device pertaining to one aspect of the present disclosure is an ultrasound diagnostic device that causes a probe to transmit a push wave focused on a specific site in a subject and detects propagation speed of a shear wave generated by acoustic radiation force of the push wave, the probe being connectable to the ultrasound diagnostic device and including transducers arranged in a row, the ultrasound diagnostic device comprising: ultrasound signal processing circuitry, the ultrasound signal processing circuitry comprising: a push wave pulse transmitter that supplies a push wave pulse to a plurality of the transducers that causes the plurality of the transducers to transmit the push wave; a detection wave pulse transmitter that, a plurality of times after the push wave pulse, supplies a detection wave pulse to a plurality of the transducers that causes the plurality of the transducers to transmit a detection wave that passes through a region of interest that represents a range to be analyzed in the subject; a detection wave receiver that generates acoustic line signals with respect to observation points in the region of interest, based on reflected detection waves that correspond to the detection waves and are reflected from subject tissue and received in a time sequence by a plurality of the transducers, and generates a sequence of acoustic line signal frame data; a displacement detector that, from the sequence of acoustic line signal frame data, detects displacement of tissue in the region of interest for each receive time of the reflected detection waves, and generates a sequence of displacement frame data; a propagation information analyzer that extracts shear wave wavefront position from the sequence of the displacement frame data, generates a sequence of wavefront frame data, and generates wavefront arrival time frame data by associating wavefront position included in each frame of the wavefront frame data with the receive time; a propagation information estimator that evaluates reliability of wavefront arrival time data in the wavefront arrival time frame data and, for reliability nonconformance wavefront arrival time data in the wavefront arrival time frame data that does not satisfy a predefined condition, generates compensated wavefront arrival time data by interpolation based on wavefront arrival time data that does satisfy the predefined condition, replaces the reliability nonconformance wavefront arrival time data with the compensated wavefront arrival time data, and generates compensated wavefront arrival time frame data; and an elastic modulus calculator that calculates shear wave propagation speed and/or elastic modulus frame data in the region of interest, based on the compensated wavefront arrival time frame data.

BRIEF DESCRIPTION OF THE DRAWINGS

These and the other objects, advantages and features of the invention will become apparent from the following description thereof taken in conjunction with the accompanying drawings which illustrate a specific embodiment of the invention. In the drawings.

DESCRIPTION OF EMBODIMENTS

Embodiment 1

Figure 1:
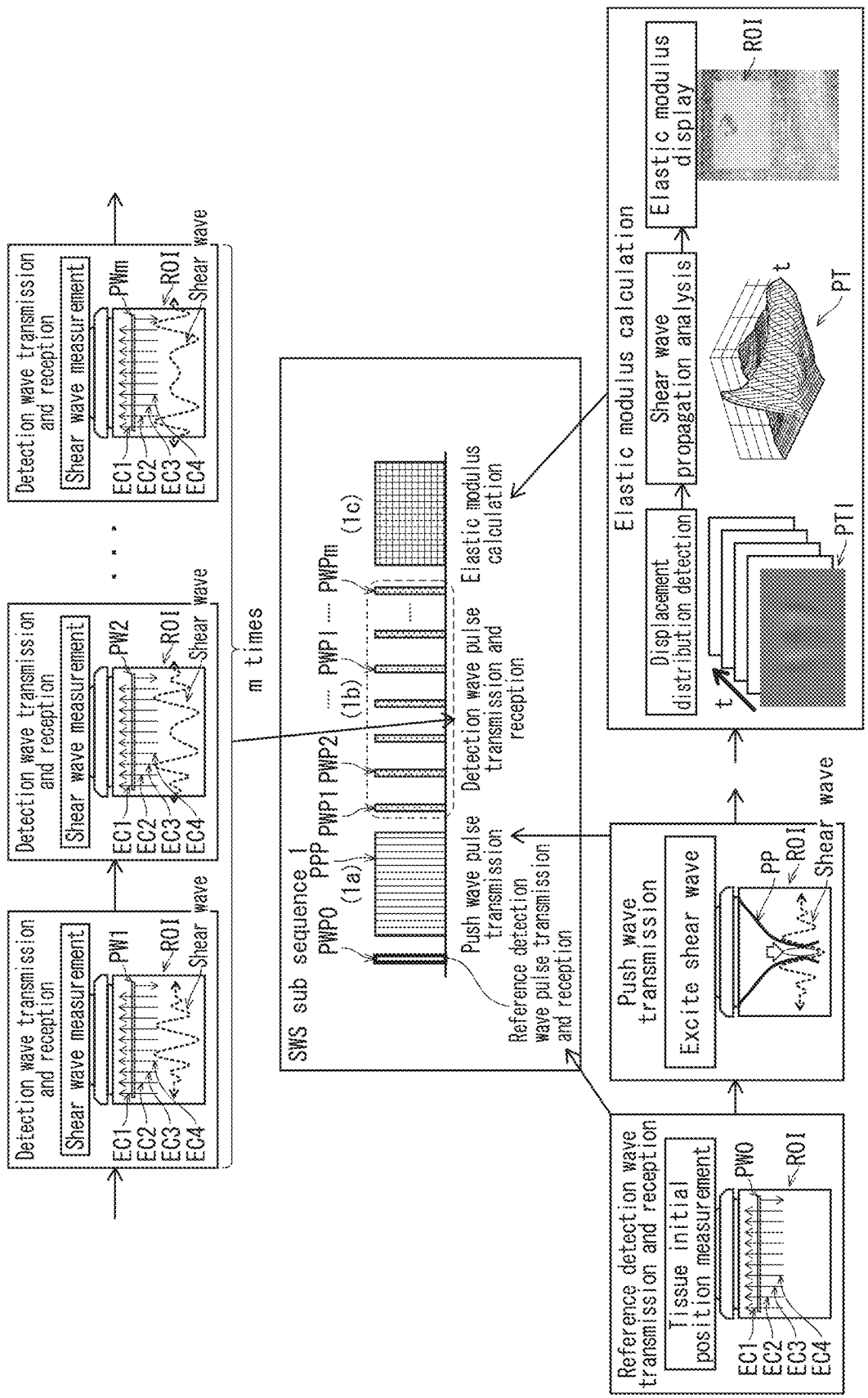
FIG. 1 is a schematic diagram showing an outline of a shear wave speed (SWS) sequence according to an ultrasound elastic modulus measurement method in ultrasound diagnostic device 100 pertaining to Embodiment 1.

An ultrasound diagnostic device 100 calculates propagation speed of a shear wave representing elastic modulus of tissue, according to an ultrasound elastic modulus measurement method. FIG. 1 is a schematic diagram showing an outline of a shear wave speed (SWS) sequence according to an ultrasound elastic modulus measurement method in the ultrasound diagnostic device 100. As shown in the central box of FIG. 1, processing of the ultrasound diagnostic device 100 consists of "reference detection wave pulse transmission and reception", "push wave pulse transmission", "detection wave pulse transmission and reception", and "elastic modulus calculation" processes.

In the process of "reference detection wave pulse transmission and reception", a reference detection wave pulse PWP0 is transmitted to an ultrasound probe, causing a plurality of transducers to transmit a detection wave PW0 in a range corresponding to a region of interest ROI in a subject and receive reflected waves EC1 to EC4, in order to generate an acoustic line signal that is a reference for initial position of tissue. In the process of "push wave pulse transmission", a push wave pulse PPP is transmitted to an ultrasound probe, causing a plurality of transducers to transmit a push wave PP obtained by converging ultrasound to a specific site in a subject, in order to excite a shear wave in subject tissue. Subsequently, in the process of "detection wave pulse transmission and reception", a detection wave pulse PWP1 (here "1" represents a natural number from one to a transmission count m of detection wave pulses PWP, and where numbers are not distinguished is referred to as detection wave pulse PWP1) is transmitted to an ultrasound probe, causing a plurality of transducers to transmit a detection wave PW1 and receive reflected waves EC1 to EC4 multiple times, in order to measure the shear wave. In the process of "elastic modulus calculation", first, displacement distribution PT1 of tissue associated with propagation of the shear wave generated by acoustic radiation force of the push pulse is calculated in a time series, then, from changes in the time series of displacement distribution PT1, shear wave propagation analysis is performed for calculating propagation speed of the shear wave representing elastic modulus of tissue, and finally distribution of tissue elasticity is imaged and displayed as an elastic modulus image, for example.

As shown above, the series of processes associated with one shear wave excitation based on push wave PP transmission is referred to as a "SWS sequence", and a process in which a plurality of "SWS sequences" are integrated is referred to as an "integrated SWS sequence".

<Ultrasound Diagnostic System 1000>

1. Configuration Outline

Figure 2:
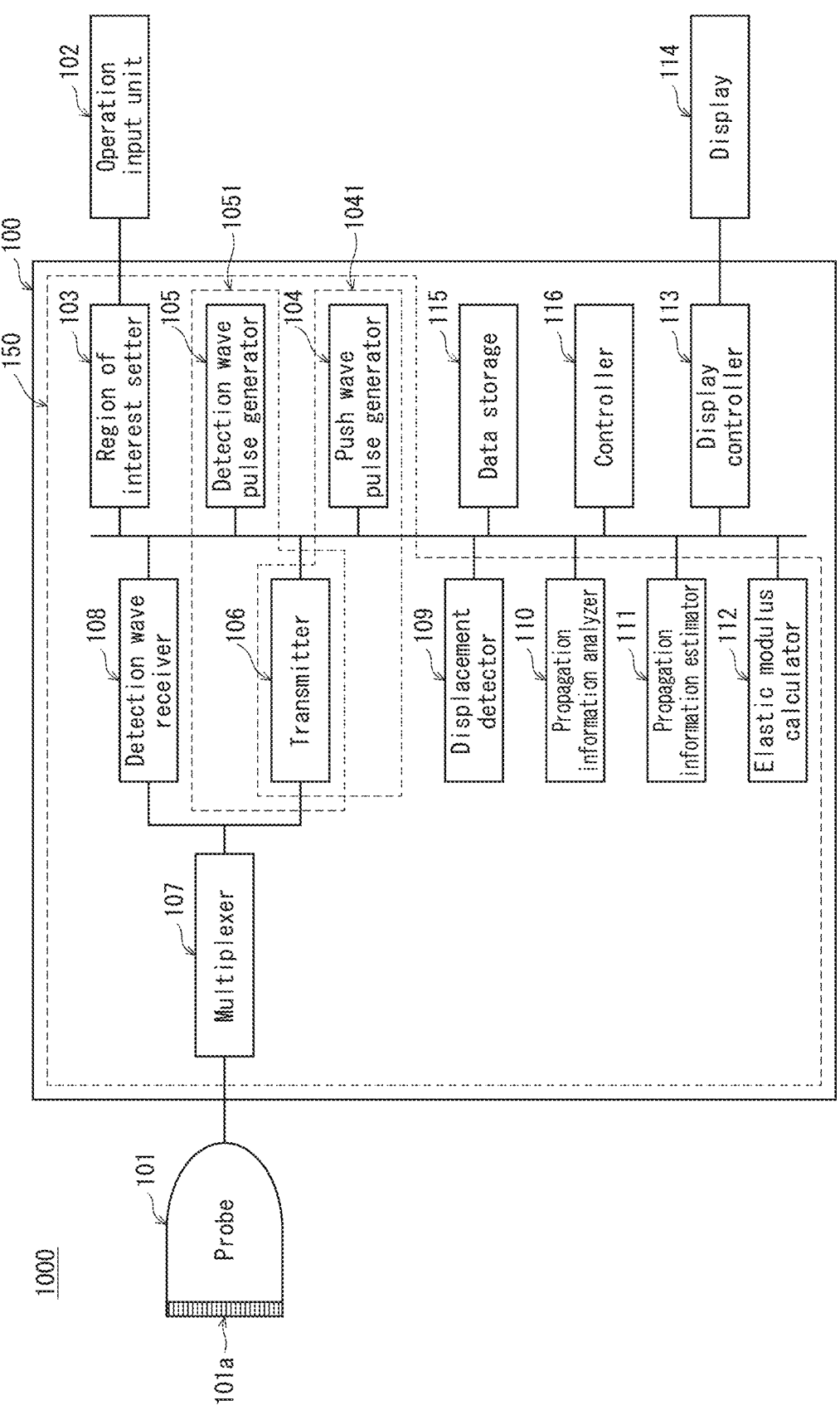
FIG. 2 is function block diagram of an ultrasound diagnostic system 1000 including ultrasound diagnostic device 100.

An ultrasound diagnostic system 1000 including the ultrasound diagnostic device 100 pertaining to Embodiment 1 is described with reference to the drawings. FIG. 2 is a function block diagram of the ultrasound diagnostic system 1000 pertaining to Embodiment 1. As shown in FIG. 2, the ultrasound diagnostic system 1000 has an ultrasound probe 101 (hereinafter, "probe 101") that has a plurality of transducers (transducer array) 101a arranged on a front end surface thereof that transmit ultrasound towards a subject and receive reflected waves, the ultrasound diagnostic device 100 that causes the probe 101 to transmit and receive ultrasound and generates an ultrasound image based on an output signal from the probe 101, an operation input unit 102 that receives operation input from a user, and a display 114 that displays the ultrasound image on a screen thereof. The probe 101, the operation input unit 102, and the display 114 are each connectable to the ultrasound diagnostic device 100. FIG. 2 shows the probe 101, the operation input unit 102, and the display 114 connected to the ultrasound diagnostic device 100.

The following describes each element connected to the ultrasound diagnostic device 100.

2. Probe 101

The probe 101 has a transducer array (101a) composed of the transducers 101a arranged in, for example, a one-dimensional direction (hereinafter, "transducer array direction"). The probe 101 converts a pulsed electric signal supplied from a transmitter 106 (hereinafter, "transmit signal") into pulsed ultrasound. The probe 101, in a state in which a transducer-side outer surface of the probe 101 is in contact with a skin surface of a subject via ultrasound gel or the like, transmits an ultrasound beam composed of a plurality of ultrasound waves emitted from a plurality of transducers towards a measurement target. Then the probe 101 receives reflected detection waves (hereinafter, "reflected waves") from the subject, a plurality of the transducers 101a convert the reflected waves to electric signals, and the probe 101 supplies the electric signals to the ultrasound diagnostic device 100.

3. Operation Input Unit 102

The operation input unit 102 receives various operation inputs such as various settings and operations with respect to the ultrasound diagnostic device 100 from a user, and outputs to a controller 116 of the ultrasound diagnostic device 100.

The operation input unit 102 may be, for example, a touch panel integrated with the display 114. In this case, various settings and operations of the ultrasound diagnostic device 100 can be performed by touch operations and drag operations on operation keys displayed on the display 114, and the ultrasound diagnostic device 100 is configured to be operable via the touch panel. Alternatively, the operation input unit 102 may, for example, be a keyboard that has various operation keys, various operation buttons, an operation panel that has a lever and the like, a mouse, or the like.

4 Display 114

The display 114 is a display device for image display, and displays an image output from a display controller 113 (described later) to a screen. A liquid crystal display, a cathode ray tube (CRT), an organic electroluminescence (EL) display, and the like can be used for the display 114.

<Configuration Outline of Ultrasound Diagnostic Device 100>

The following describes the ultrasound diagnostic device 100 pertaining to Embodiment 1.

The ultrasound diagnostic device 100 has a multiplexer 107 that selects each transducer to be used when transmitting or receiving, among the transducers 101a of the probe 101, and secures input and output of selected transducers, a transmitter 106 that controls timing of high voltage application to each of the transducers 101a of the probe 101 for ultrasound transmission, and a detection wave receiver 108 that performs receive beamforming based on reflected waves received by the probe 101 in order to generate an acoustic line signal.

Further, the ultrasound diagnostic device 100 has a region of interest setter 103 that sets a region of interest ROI as a reference for a plurality of the transducers 101a, the region of interest ROI representing an analysis target range in a subject, based on operation input from the operation input unit 102, a push wave pulse generator 104 that causes transmission of a push wave pulse PPP to a plurality of the transducers 101a, and a detection wave pulse generator 105 that causes multiple transmissions of a detection wave pulse PWP1 after the push wave pulse PPP.

Further, the ultrasound diagnostic device 100 has a displacement detector 109 that detects tissue displacement in a region of interest ROI from an acoustic line signal, a propagation information analyzer 110 that analyzes shear wave propagation information from detected tissue displacement and calculates wavefront arrival time of the shear wave at each observation point in the region of interest ROI, a propagation information estimator 111 that estimates wavefront arrival time of the shear wave for specified observation points in the region of interest ROI, and an elastic modulus calculator 112 that calculates elastic modulus or propagation speed of the shear wave at each observation point in the region of interest ROI.

Further, the ultrasound diagnostic device 100 includes a data storage 115 that stores data including an acoustic line signal outputted by the detection wave receiver 108, displacement data outputted by the displacement detector 109, wavefront data and wavefront arrival time data outputted by the propagation information analyzer 110, compensated wavefront arrival time data outputted by the propagation information estimator 111, and wavefront data and elastic modulus data outputted by the elastic modulus calculator 112; and a controller 116 that controls each component of the ultrasound diagnostic device 100.

Of these, the multiplexer 107, the transmitter 106, the detection wave receiver 108, the region of interest setter 103, the push wave pulse generator 104, the detection wave pulse generator 105, the displacement detector 109, the propagation information analyzer 110, the propagation information estimator 111, and the elastic modulus calculator 112 constitute ultrasound signal processing circuitry 150.

Elements that constitute the ultrasound signal processing circuitry 150, the controller 116, and the display controller 113 are each implemented by hardware circuits such as field programmable gate arrays (FPGA), application specific integrated circuits (ASIC), or the like. Alternatively, they may be implemented by software and a programmable device such as a central processing unit (CPU), general-purpose computing on a graphic processing unit (GPGPU), a processor, or the like. These elements can each be a single circuit component or an assembly of circuit components. Further, a plurality of elements can be combined into a single circuit component or can be an aggregate of a plurality of circuit components.

The data storage 115 is a computer-readable storage medium, and may be a flexible disk, hard disk, MO, DVD, DVD-RAM, semiconductor memory, or the like. Further, the data storage 115 may be a storage device that is externally connectable to the ultrasound diagnostic device 100.

The ultrasound diagnostic device 100 pertaining to Embodiment 1 is not limited to the ultrasound diagnostic device configuration shown in FIG. 2. For example, the multiplexer 107 may be unnecessary, or the transmitter 106 and/or the detection wave receiver 108, or a portion thereof, may be housed in the probe 101.

<Configuration of Elements of Ultrasound Diagnostic Device 100>

The following describes function blocks included in the ultrasound diagnostic device 100.

1. Region of Interest Setter 103

Typically, when a B mode image, which is a cross-section image of a subject acquired in real time by the probe 101, is being displayed on the display 114, a user, using the B mode image displayed on the display 114 as an index, specifies an analysis target range in the subject and inputs to the operation input unit 102. The region of interest setter 103 sets information specified by a user via the operation input unit 102 as input, and outputs to the controller 116. At such time, the region of interest setter 103 may set a region of interest ROI that represents an analysis target range in a subject with reference to position of the transducer array (101a) composed of the transducers 101a of the probe 101. For example, a region of interest ROI may be all or part of a detection wave irradiation region Ax of the transducer array (101a) composed of the transducers 101a.

2. Push Wave Pulse Generator 104

The push wave pulse generator 104 inputs information indicating a region of interest ROI from the controller 116, and sets a specific point at a predefined position in the region of interest ROI. Then, by causing the transmitter to transmit a push wave pulse PPP to a plurality of the transducers 101a, it is possible to make the plurality of the transducers 101a transmit a push wave PP that converges an ultrasound beam to a specific site in the subject that corresponds to a specific point (hereinafter, "transmission focus point F"). Alternatively, a predefined position outside the region of interest ROI, which is near the region of interest ROI, may be set as the transmission focus point F. In the case of a setting near the region of interest ROI, the transmission focus point F is set at a distance from the region of interest ROI that allows a shear wave to arrive at the region of interest ROI.

More specifically, the push wave pulse generator 104 determines, based on information indicated by the region of interest ROI, a position of the transmission focus point F of a push wave and a transducer array to transmit a push wave (hereinafter, "push wave transmission transducer array Px").

Figure 3A:
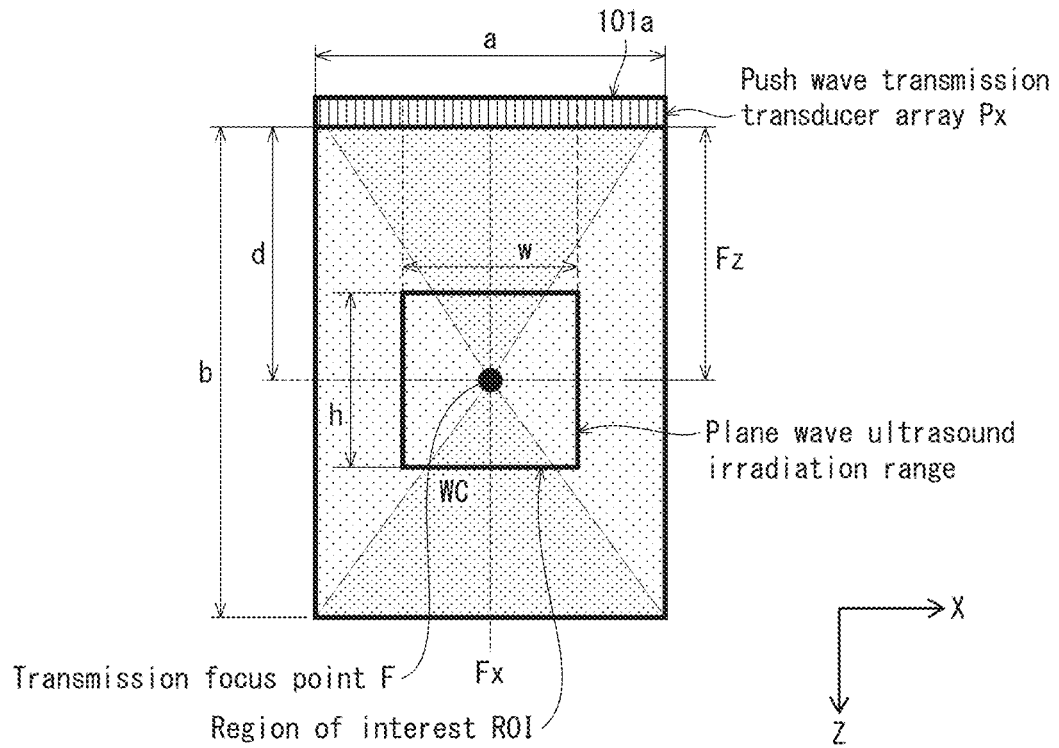
FIG. 3A is a schematic diagram showing a position of a transmission focus point F of a push wave generated by push wave pulse generator 104.

FIG. 3A is a schematic diagram showing a position of a transmission focus point F of a push wave generated by the push wave pulse generator 104. A row direction length w and a subject depth direction length h of a region of interest ROI are fractions of a row direction length a and a subject depth direction length b, respectively, of an ultrasound wave irradiation range by a plane wave, and a case in which a region of interest ROI is set near a center of an ultrasound irradiation range is described as an example. According to the present embodiment, as shown in FIG. 3A, as an example of a position of the transmission focus point F, a row direction transmission focus point position Fx coincides with a row direction center position WC of the region of interest ROI, and a depth direction transmission focus point position Fz coincides with a depth d to a center of the region of interest ROI.

Further, the push wave transmission transducer array Px is set based on the depth direction transmission focus point position Fz. According to the present embodiment, the push wave pulse transmission transducer array length a is configured to be an array length of all of the transducers 101a. However, positions of the region of interest ROI and the transmission focus point F relative to each other are not limited to the above example, and may be appropriately changed according to form of a site to be examined in a subject, or for other reasons.

For example, the example shown in FIG. 3A may be changed so that the row direction transmission focus point position Fx in the position of the transmission focus point F is offset in a positive or negative direction along the X axis from the row direction center position WC of the region of interest ROI. In this case, row direction center points of the region of interest width w and the transducer array are different. Further, the row direction transmission focus point position Fx in the position of the transmission focus point F may be offset to a position outside the region of interest ROI in a positive or negative direction along the X axis from the row direction center position WC of the region of interest ROI.

Further, in a case in which the region of interest width w is relatively large, a plurality of push waves may be generated, each having different transmission focus points F.

Note that "converging" an ultrasound beam by push waves means that the ultrasound beam is focused and is a focus beam, that is, an area irradiated by the ultrasound beam decreases after transmission and achieves a minimum value at a specified depth, but does not indicate limitation to a case in which the ultrasound beam is focused to one point. The "transmission focus point F" may indicate an ultrasound beam center at a depth at which an ultrasound beam converges.

Position of the transmission focus point F and information indicating the push wave transmission transducer array Px, together with pulse width of the push wave pulse PPP, are outputted to the transmitter 106 as a transmission control signal.

3. Detection Wave Pulse Generator 105

The detection wave pulse generator 105 inputs information indicating a region of interest ROI from the controller 116 and causes the transmitter to transmit a detection wave pulse PWP1 to a plurality of the transducers 101a multiple times, thereby causing the plurality of transducers 101a that belong to a detection wave pulse transmission transducer array Tx to transmit a detection wave PW so that an ultrasound beam passes through the region of interest ROI. More specifically, the detection wave pulse generator 105, based on information indicating a region of interest ROI, determines a transducer array to transmit a detection wave pulse PWP1 (hereinafter, "detection wave transmission transducer array Tx") so that an ultrasound beam passes through the region of interest ROI.

Figure 3B:
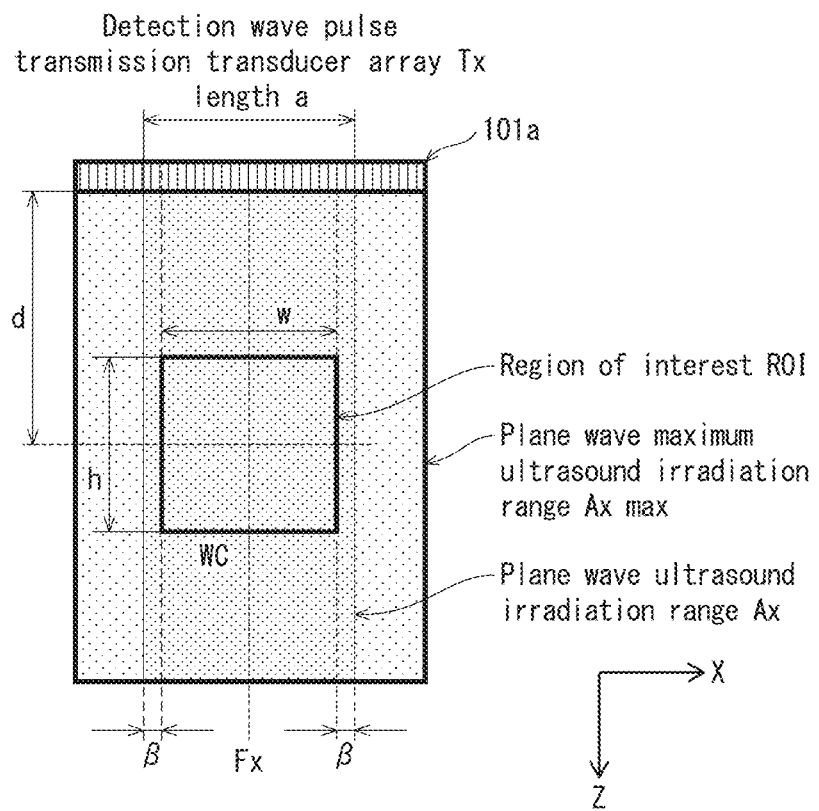
FIG. 3B is a schematic diagram showing a schematic configuration of a detection wave pulse generated by detection wave pulse generator 105.

FIG. 3B is a schematic diagram showing a schematic configuration of a detection wave pulse PWP1 generated by the detection wave pulse generator 105. As shown in FIG. 3B, the detection wave pulse generator 105 sets the detection wave pulse transmission transducer array Tx so that a detection wave, which is a plane wave driven by detection wave pulse transmission transducers in the same phase, passes through an entirety of the region of interest ROI. A length a of the detection wave pulse transmission transducer array Tx is preferably set larger than the region of interest width w. According to the present example, the region of interest width w is set to be positioned inward of ends of the detection wave pulse transmission transducer array Tx in the array direction by a predefined distance β. The detection wave PW is a plane wave, and therefore propagates in a Z direction, perpendicular to the transducer array direction. Accordingly, the region of interest ROI is included in an ultrasound irradiation region Ax with a margin of distance at both ends in the X direction. Thus, it is possible to generate an acoustic line signal for an observation point anywhere in a region of interest ROI by transmission and reception of one detection wave, and to transmit the detection wave pulse PWP1 so that an ultrasound beam reliably passes through the entirety of the region of interest ROI.

Further, the detection wave pulse transmission transducer array Tx may be all of the transducers 100a. The ultrasound irradiation region Ax can be set to a maximum ultrasound irradiation region Axmax according to a plane wave.

Information indicating the detection wave pulse transmission transducer array Tx is outputted along with a pulse width of a detection wave pulse PWP1 to the transmitter 106 as a transmission control signal.

4. Transmitter 106

The transmitter 106 is connected to the probe 101 via the multiplexer 107, and in order to transmit ultrasound from the probe 101, is a circuit that controls timing of application of a high voltage to each of all of the transducers 101a of the probe 101, or each of a plurality of transducers included in the push wave transmission transducer array Px or the detection wave transmission transducer array Tx. Note that, as shown in FIG. 2, a configuration including the push wave pulse generator 104 and the transmitter 106 is referred to as the push pulse transmitter 1041 and a configuration including the transmitter and the detection wave pulse generator 105 is referred to as the detection wave pulse transmitter 1051.

Figure 4A:
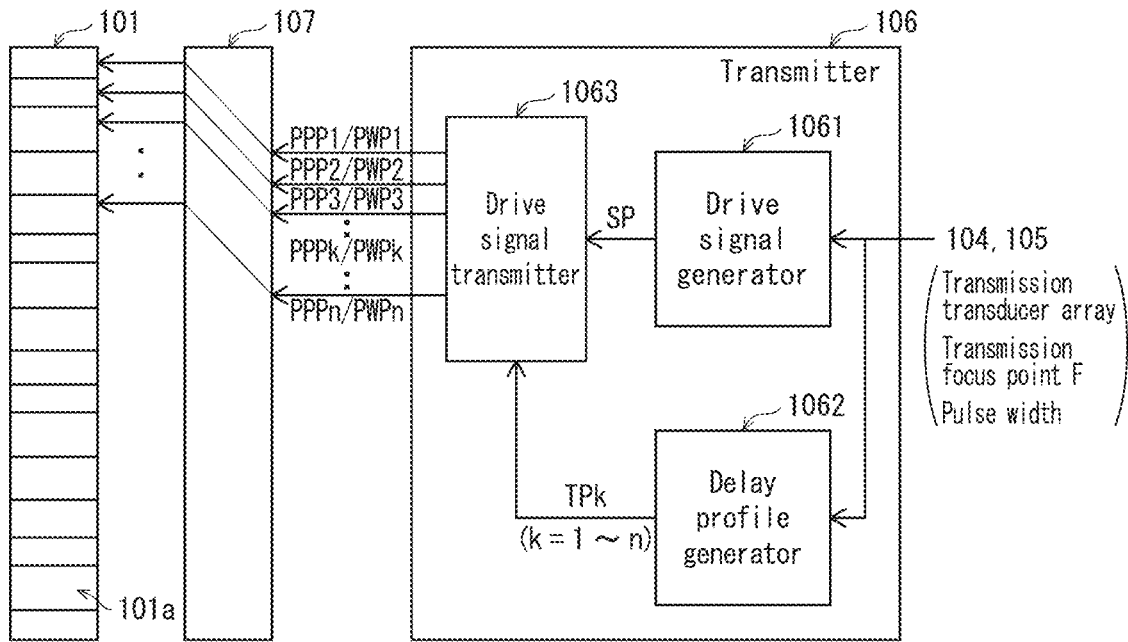
FIG. 4A is a function block diagram showing configuration of transmitter 106.

FIG. 4A is a function block diagram showing configuration of the transmitter 106. As shown in FIG. 4A, the transmitter 106 includes a drive signal generator 1061, a delay profile generator 1062, and a drive signal transmitter 1063.

(1) Drive Signal Generator 1061

The drive signal generator 1061 is a circuit that generates, among transmission control signals from the push wave pulse generator 104 and the detection wave pulse generator 105, a pulse signal SP for causing all or a portion of the transducers 101a of the probe 101 to transmit an ultrasound beam, based on information indicating pulse width and the push wave transmission transducer array Px or the detection wave transmission transducer array Tx.

(2) Delay Profile Generator 1062

The delay profile generator 1062 is a circuit that, among transmission control signals obtainable from the push wave pulse generator 104 and the detection wave pulse generator 105, sets and outputs for each transducer a delay time TPk (k being a natural number from 1 to a number n of the transducers 101a) that determines a transmission timing of an ultrasound beam, based on information indicating the transmission focus point F and the push wave transmission transducer array Px or the detection wave transmission transducer array Tx. Thus, ultrasound beam focusing is performed by causing transmission of an ultrasound beam to be delayed for each transducer by a delay time assigned thereto.

(3) Drive Signal Transmitter 1063

The drive signal transmitter 1063 performs push wave transmission processing that supplies a push wave pulse PPP, causing transmission of a push wave, to each of the transducers included in the push wave transmission transducer array Px among the transducers 101a of the probe 101, based on a pulse signal SP from the drive signal generator 1061 and a delay time TPk from the delay profile generator 1062. The push wave transmission transducer array Px is selected by the multiplexer 107. However, configurations pertaining to supply of the push wave pulse PPP are not limited to the description above. For example, a configuration may be used that does not use the multiplexer 107.

Figure 5:
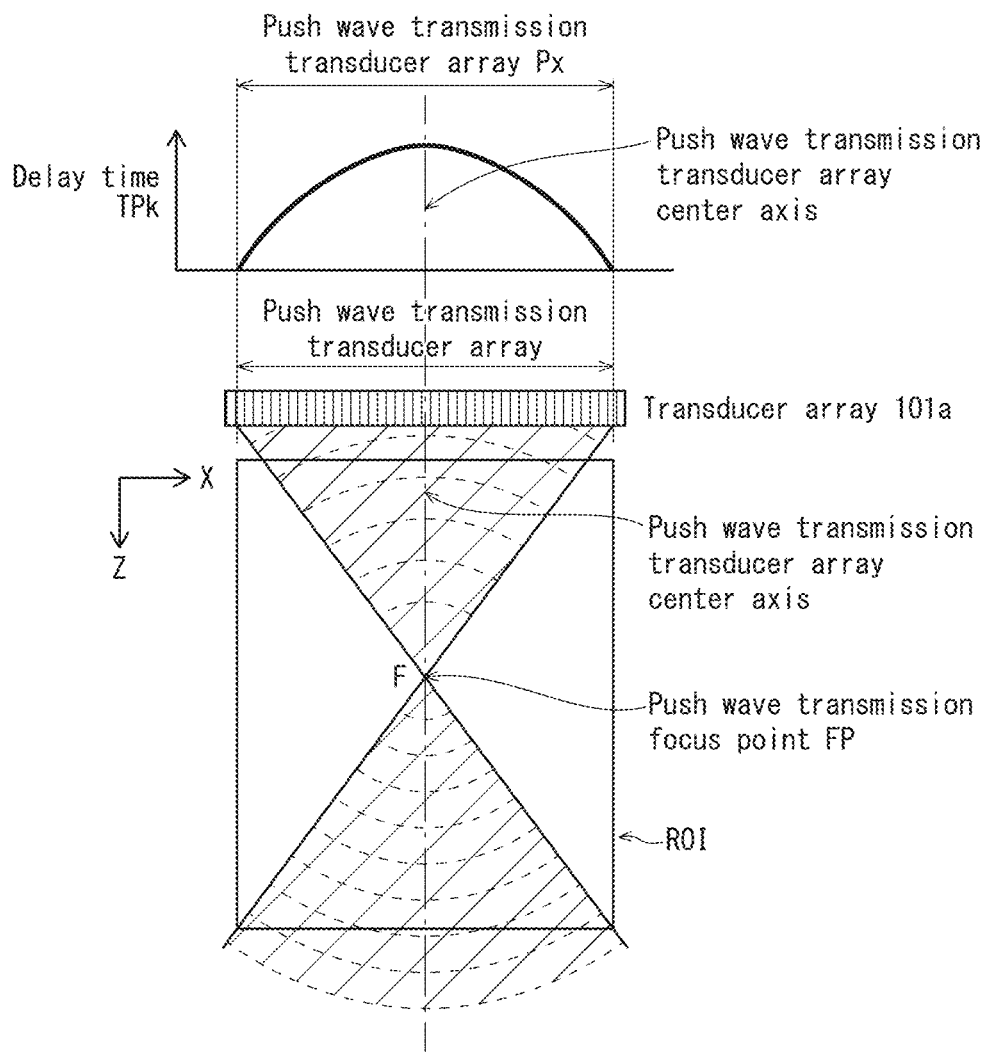
FIG. 5 is a schematic diagram showing configuration of a push wave.

FIG. 5 is a schematic diagram showing configuration of a push wave. With respect to the push wave transmission transducer array Px, a push wave pulse PPP to which a large value for the delay time TPk is applied is transmitted to a transducer positioned at a center of the transducer array. Thus, as shown in FIG. 5, a push wave PP in which ultrasound beams converge to a specific site in a subject, corresponding to the transmission focus point F, is transmitted from the push wave transmission transducer array Px.

Further, the drive signal transmitter 1063 performs detection wave transmission processing that supplies a detection wave pulse PWP1, causing transmission of an ultrasound beam, to each transducer included in the detection transmission transducer array Tx among the transducers 101a of the probe 101. The detection wave transmission transducer array Tx is selected by the multiplexer 107. However, configurations pertaining to supply of the detection wave pulse PWP1 are not limited to the description above. For example, a configuration may be used that does not use the multiplexer 107.

Figure 6A:
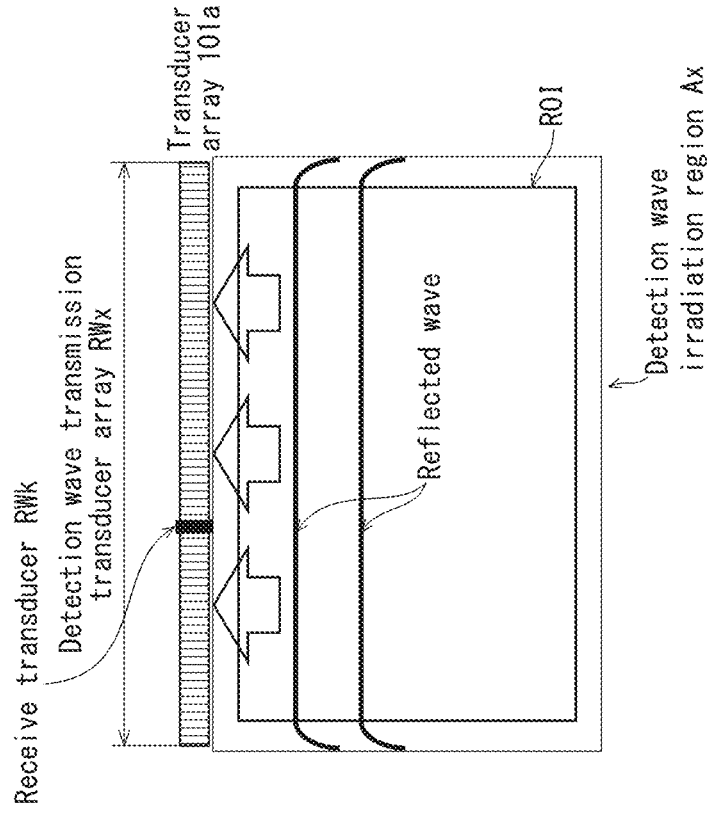
FIG. 6A is a schematic diagram showing configuration of detection wave transmission.
Figure 6B:
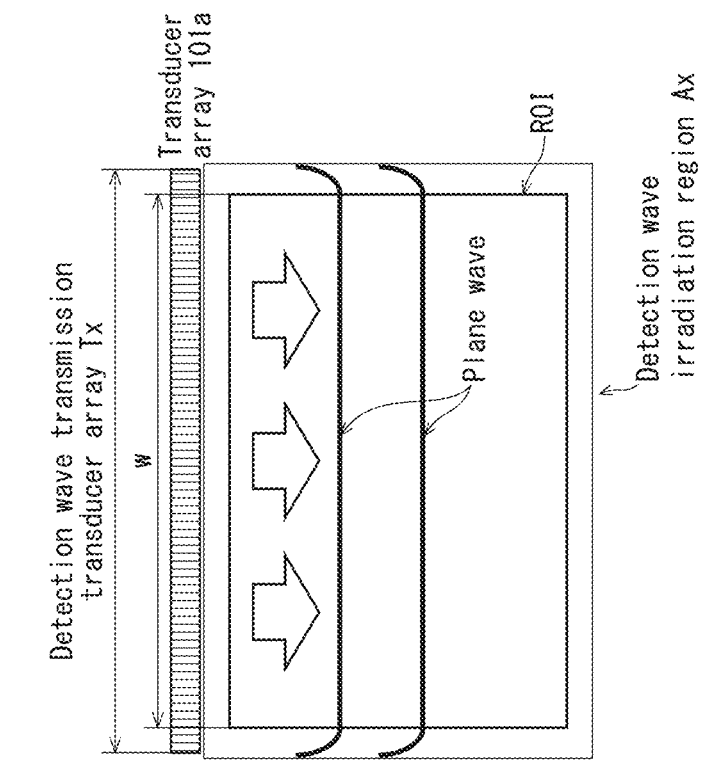
FIG. 6B is a schematic diagram showing configuration of reflected wave reception.

FIG. 6A is a schematic diagram showing configuration of detection wave transmission. The delay time TPk is not applied to transducers included in the detection wave transmission transducer array Tx, and detection wave pulses PWP1 having the same phase as each other are transmitted to the detection wave transmission transducer array Tx. Thus, as shown in FIG. 6A, a plane wave that proceeds in a subject depth direction is transmitted from the transducers in the detection wave transmission transducer array Tx. A region on a plane including the detection wave transmission transducer array Tx corresponding to a range in the subject to which a detection wave arrives is referred to as a detection wave irradiation region Ax.

The transmitter 106, after push wave pulse PPP transmission, repeatedly transmits a detection wave pulse PWP1 based on a transmission control signal from the detection wave pulse generator 105. After transmission of one push wave pulse PPP, one series of multiple transmissions of a detection wave pulse PWP1 from the same detection wave transmission transducer array Tx is referred to as a "transmission event".

2. Detection Wave Receiver 108 Configuration

The detection wave receiver 108 is a circuit that generates an acoustic line signal for a plurality of observation points Pij in the detection wave irradiation region Ax, based on reflected waves from subject tissue received by the transducers 101a in a time series corresponding to a plurality of detection wave pulses PWP1, in order to generate a sequence of acoustic line signal frame data DS1 (where l is a natural number from 1 to m, referred to as acoustic line signal frame data DS1 where numbers are not distinguished). That is, the detection wave receiver 108, after transmission of a detection wave pulse PWP1, generates an acoustic line signal from electric signals obtained at a plurality of the transducers 101a, based on a reflected wave received by the probe 101. Here, i is a natural number from 1 to n, indicating a coordinate in the x direction in the detection wave irradiation region Ax, and j is a natural number from 1 to zmax, indicating a coordinate in the z direction. Note that an "acoustic line signal" is a signal obtained by performing delay-and-sum processing on a receive signal (radio frequency (RF) signal).

Figure 4B:
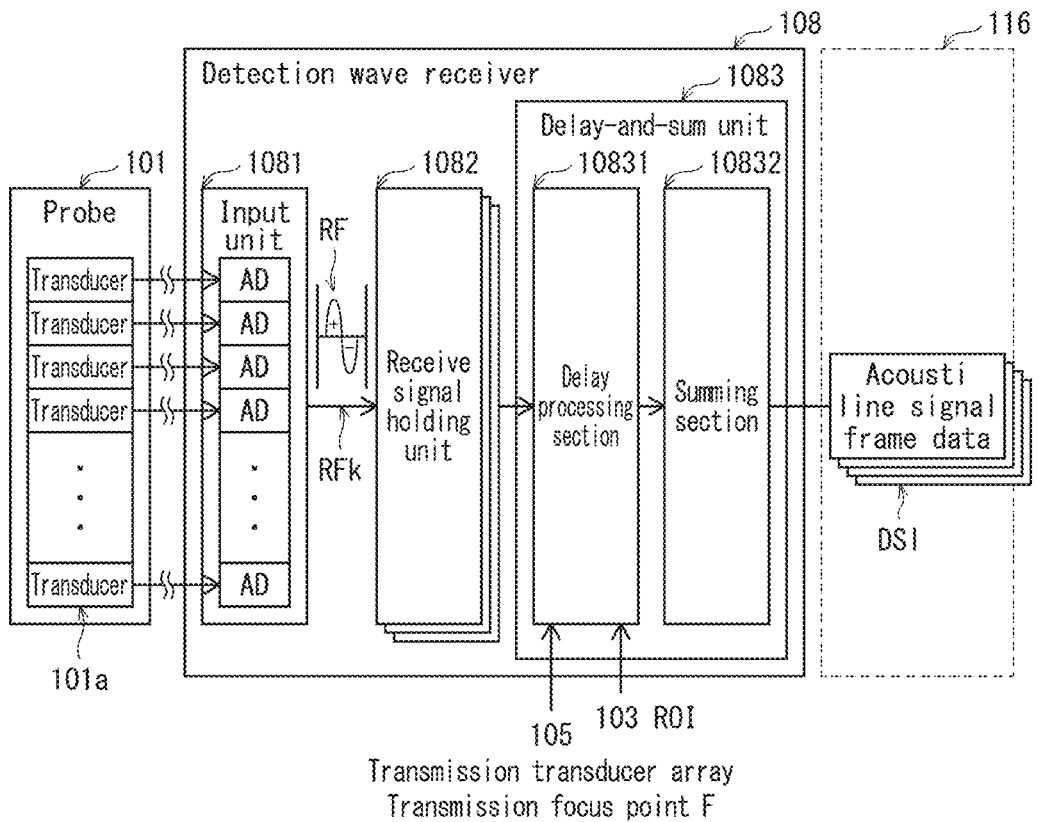
FIG. 4B is a function block diagram showing configuration of detection wave receiver 108.

FIG. 4B is a function block diagram showing configuration of the detection wave receiver 108. The detection wave receiver 108 includes an input unit 1081, a receive signal holding unit 1082, and a delay-and-sum unit 1083.

2.1 Input Unit 1081

The input unit 1081 is connected to the probe 101 via the multiplexer 107, and is a circuit that generates a receive signal (RF signal) based on reflected waves at the probe 101. Here, a receive signal RFk (where k is a natural number from 1 to n) is an RF signal obtained by analogue/digital (A/D) conversion of an electric signal converted from a reflected wave received by transducers, based on transmission of a detection wave pulse PWP1. A receive signal RFk is composed of a series of signals (receive signal series) that continue in the transmission direction of ultrasound (subject depth direction) received by each receive transducer RWk.

The input unit 1081 generates a receive signal RFk for each receive transducer RWk for each transmission event, based on reflected waves obtained at each receive transducer RWk. A receive transducer array is composed from part or all of the transducers 101a of the probe 101, and is selected by the multiplexer 107 based on an instruction from the controller 116. According to the present example, all of the transducers 101a are selected as a receive transducer array. Thus, reflected waves from observation points in the entirety of the detection wave irradiation region Ax due to one receive process can be received by using all transducers, in order to generate a receive transducer array of all transducers. A generated receive signal RFk is outputted to the receive signal holding unit 1082.

2.2 Receive Signal Holding Unit 1082

The receive signal holding unit 1082 is a computer-readable storage medium such as a semiconductor memory, for example. The receive signal holding unit 1082 inputs receive signals RFk for each receive transducer RWk from the input unit 1081, synchronized to a transmission event, holding same until one frame of acoustic line signal frame data is generated.

The receive signal holding unit 1082 may be a portion of the data storage 115.

2.3 Delay-and-Sum Unit 1083

The delay-and-sum unit 1083 is a circuit that, synchronized to a transmission event, after performing delay processing on receive signals RFk from an observation point Pij in a region of interest ROI and received by receive transducers RPk included in the detection wave receive transducer array Rx, performs summing for all the receive transducers RPk to generate an acoustic line signal DS. The detection wave receive transducer array Rx is composed from receive transducers RPk that are part or all of the transducers 101a of the probe 101, and is selected by delay-and-sum unit 1083 and the multiplexer 107 based on an instruction from the controller 116. According to the present example, a transducer array including at least all of the transducers of the detection wave pulse transmission transducer array Tx for one transmission event is selected as the detection wave receive transducer array Rx.

The delay-and-sum unit 1083 includes a delay processing section 10831 and a summing section 10832 for processing receive signals RFk.

(1) Delay Processing Section 10831

The delay processing section 10831 is a circuit that identifies, from receive signals RFk of receive transducers RPk in the detection wave receive transducer array Rx, a receive signal as corresponding to a receive transducer RPk, based on reflected ultrasound reflection from an observation point Pij, by compensating according to an arrival time difference (delay) of the reflected ultrasound to the receive transducer RPk, which is obtained by dividing a difference in distance between an observation point Pij and the receive transducer RPk by a speed of sound value.

Figure 7:
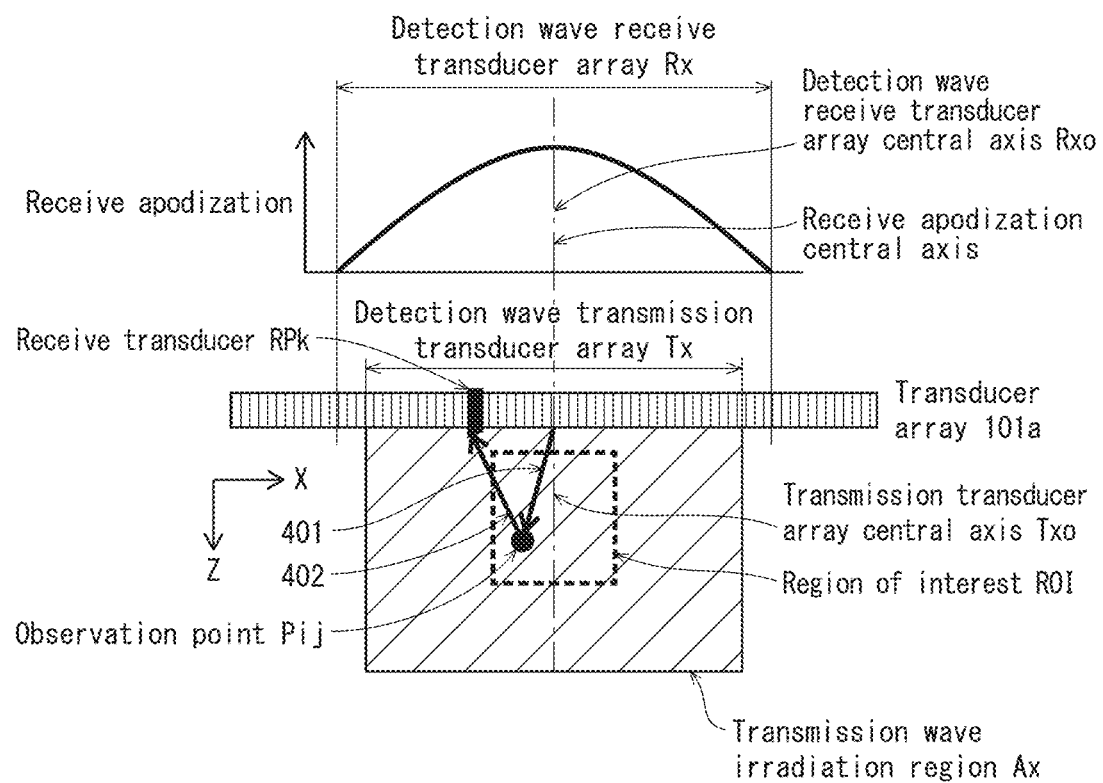
FIG. 7 is a schematic diagram showing configuration of an ultrasound wave propagation path measurement method in delay processing section 10831.

FIG. 7 is a schematic diagram showing configuration of an ultrasound wave propagation path measurement method in the delay processing section 10831. FIG. 7 shows a propagation path of ultrasound radiated from the detection wave pulse transmission transducer array Tx and reflected at an observation point Pij at an arbitrary position in the region of interest ROI to reach a receive transducer RPk.

a) Transmission Time Detection

A detection wave PW1 transmitted from the detection wave transmission transducer array Tx (all of the transducer array (101a)) is a plane wave, as mentioned above. Accordingly, the delay processing section 10831, in response to a transmission event, calculates a transmission path to an observation point Pij as a shortest path 401 until a detection wave PW1 emitted orthogonally to the detection wave transmission transducer array Tx reaches the observation point Pij, then divides by the speed of sound to calculate transmission time.

b) Receive Time Detection

The delay processing section 10831, in response to a transmission event, with respect to an observation point Pij, calculates a receive path until ultrasound reflected at the observation point Pij reaches a receiver transducer RPk included in the detection wave receive transducer array Rx. A receive path when a reflected wave reflected at an observation point Pij returns to a receive transducer RPk is geometrically calculated to have a length of a path 402 from the observation point Pij to the receive transducer RPk. This is divided by the speed of sound to calculate receive time.

c) Delay Calculation

Next, the delay processing section 10831 calculates a total propagation time from transmission time and receive time to each receive transducer RPk, then, based on the total propagation time, calculates a delay to apply to the receive signal RFk for each receive transducer RPk.

d) Delay Processing

Next, the delay processing section 10831 identifies, from receive signals RFk of each receive transducer RPk, a receive signal RFk corresponding to a delay (receive signal corresponding to time obtained by subtracting a delay) as a signal corresponding to a receive transducer RPk, based on a reflected wave from an observation point Pij.

The delay processing section 10831, in response to a transmission event, inputs receive signals RFk from the receive signal holding unit 1082, and identifies a receive signal RFk for each receive transducer RPk, for all observation points Pij in a region of interest ROI.

(2) Summing Section 10832

The summing section 10832 is a circuit that inputs receive signals RFk identified as corresponding to receive transducers RPk and outputted from the delay processing section 10831, sums the receive signals RFk, and generates an acoustic line signal DSij, which has been subjected to delay-and-sum with respect to an observation point Pij.

Further, an acoustic line signal DSij for an observation point Pij may be generated by multiplying a receive signal RFk (identified as corresponding to a receive transducer RPk) by a receive apodization (weighting series) prior to summing. Receive apodization is a series of weighting coefficients applied to receive signals corresponding to receive transducers RPk in the detection wave receive transducer array Rx. Receive apodization is set so that a weight for a transducer positioned at a center of an array direction of the detection wave receive transducer array Rx is a maximum weight, a central axis of distribution of the receive apodization coincides with a detection wave receive transducer array central axis Rxo, and distribution has a symmetrical shape across the central axis. Shape of distribution is not particularly limited.

The summing section 10832 generates an acoustic line signal DSij for each observation point Pij present in a region of interest ROI, in order to generate acoustic line signal frame data DS1.

Then, synchronized to transmission events, transmission and reception of a detection wave pulse PWP1 is repeated to generate acoustic line signal frame data DS1 for all of transmission events. Generated acoustic line signal frame data DS1 is outputted to and stored in the data storage 115 for each transmission event.

3. Displacement Detector 109

The displacement detector 109 is a circuit that detects displacement of tissue in a detection wave irradiation region Ax from a sequence of acoustic line signal frame data DS1.

Figure 8:
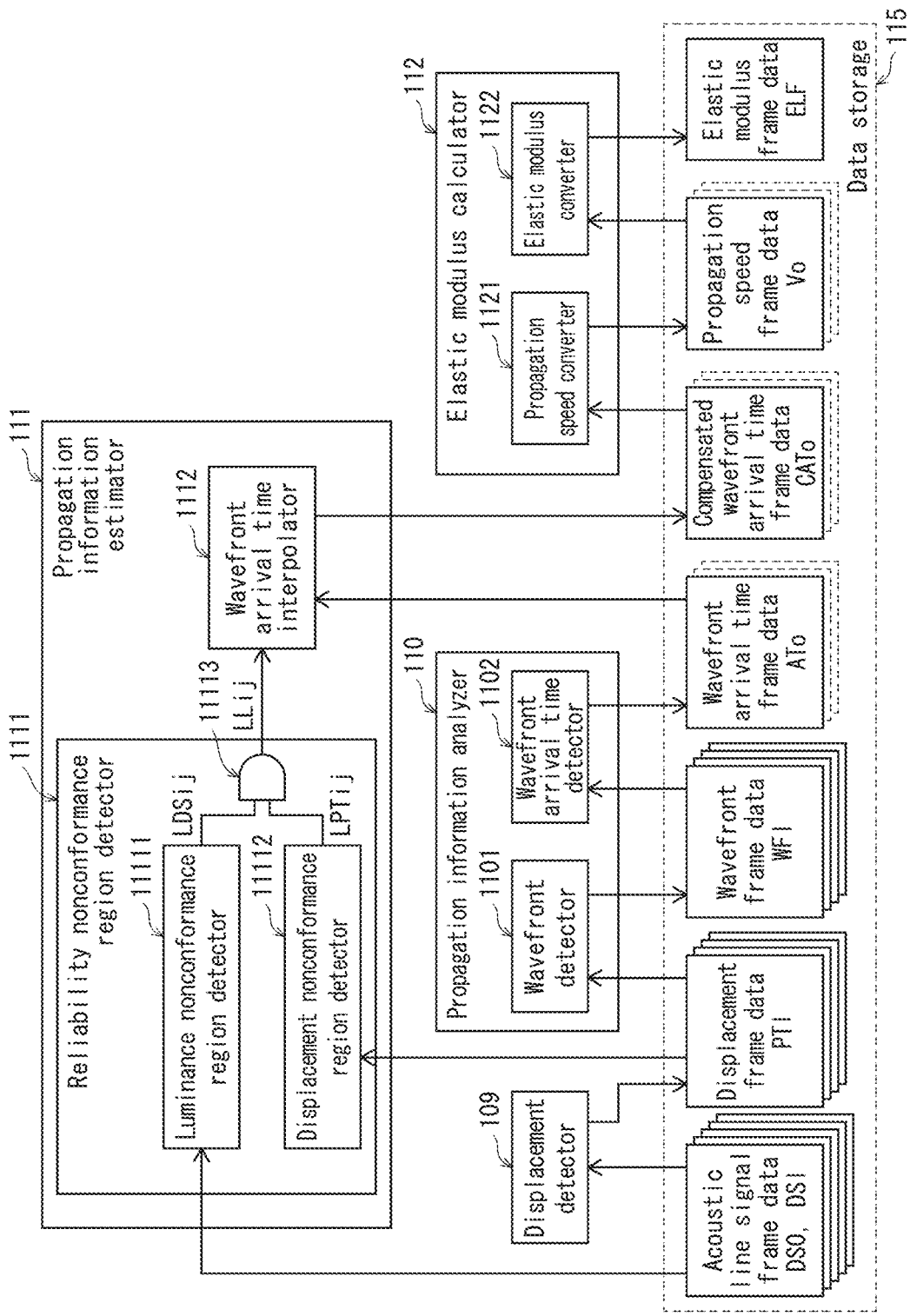
FIG. 8 is a function block diagram showing configuration of a displacement detector 109, a propagation information analyzer 110, a propagation information estimator 111, and an elastic modulus calculator 112.

FIG. 8 is a function block diagram showing configuration of the displacement detector 109, the propagation information analyzer 110, the propagation information estimator 111, and the elastic modulus calculator 112. The displacement detector 109 acquires one frame of acoustic line signal frame data DS1 as a target for displacement detection in a sequence of acoustic line signal frame data DS1 and one frame of acoustic line signal frame data DS0 as a reference (hereinafter, "reference acoustic line signal frame data DS0") from the data storage 115 via the controller 116. The reference acoustic line signal frame data DS0 is a reference signal for extracting displacement due to a shear wave in acoustic line signal frame data DS1 corresponding to a transmission event, and more specifically is acoustic line signal frame data acquired from a detection wave irradiation region Ax prior to push wave pulse PPP transmission. Thus, the displacement detector 109 detects displacement (movement of image information) PTij of an observation point Pij in detection wave irradiation region Ax of acoustic line signal frame data DS1 from a difference between acoustic line signal frame data DS1 and reference acoustic line signal frame data DS0, and generates displacement frame data PT1 in which displacement PTij is associated with coordinates of observation point Pij (here, 1 is a natural number from 1 to m, and displacement frame data PT1 is referred to where numbers are not distinguished). The displacement detector 109 outputs generated displacement frame data PT1 to the data storage 115.

4. Propagation Information Analyzer 110

The propagation information analyzer 110 is a circuit that calculates wavefront arrival time data ATij for a plurality of observation points Pij in a region of interest ROI, and calculates wavefront arrival time frame data AT1 for the region of interest ROI. The propagation information analyzer 110 is composed of a wavefront detector 1101 and a wavefront arrival time detector 1102.

The wavefront detector 1101, for each transmission event, from a sequence of displacement frame data PT1, with respect to observation points Pij in a region of interest ROI, generates a sequence of wavefront frame data WF1 representing shear wave wavefront position at time points on a time axis corresponding to each detection wave pulse PWP1, and outputs the sequence of wavefront frame data WF1 (here, 1 is a natural number from 1 to m, and is referred to as wavefront frame data WF1 where the number is not distinguished) to the data storage 115.

More specifically, the wavefront detector 1101 acquires displacement frame data PT1 from the data storage 115. The propagation information analyzer 110 detects an extremum of displacement data PTij from displacement frame data PT1, and extracts extrema of displacement data PTij that are continuous on an XZ plane as shear wave wavefront position WFij. The propagation information analyzer 110 extracts wavefront position WFij for a region of interest ROI in each transmission event in order to generate a sequence of wavefront frame data WF1.

The wavefront arrival time detector 1102, from a sequence of wavefront frame data WF1, detects a shear wave wavefront WF, position WFij, and travel direction at each time displacement frame data PT1 is acquired (upon which wavefront frame data WF1 depends), generates wavefront arrival time frame data ATo based on the wavefront position WFij of wavefront frame data WF1 and frame data acquisition time t1, and outputs the wavefront arrival time frame data ATo (here, o is a natural number representing a number of different wavefronts, and is referred to as wavefront arrival time frame data AT when numbers are not distinguished) to the data storage 115.

5. Propagation Information Estimator 111

The propagation information estimator 111 is a circuit that evaluates reliability of wavefront arrival time data AT in wavefront arrival time frame data ATo, and generates compensated wavefront arrival time frame data CATo (where o is a natural number representing a number of a wavefront, and compensated wavefront arrival time frame data CAT is used where wavefront number is not distinguished), which is obtained by replacing reliability nonconformance wavefront arrival time data ATij with compensated wavefront arrival time data CATij, which is interpolated based on wavefront arrival time data ATij that satisfies a predefined condition.

The propagation information estimator 111 is composed of a reliability nonconformance region detector 1111 and a wavefront arrival time interpolator 1112.

The reliability nonconformance region detector 1111 is composed of a luminance nonconformance region detector 11111, a displacement nonconformance region detector 11112, and an adder 11113.

The luminance nonconformance region detector 11111 detects a reliability nonconformance observation point LLij included in a reliability nonconformance region LLR in which data reliability of an acoustic line signal DSij in acoustic line signal frame data DS1, upon which wavefront arrival time frame data ATo depends, is equal to or below a threshold value. More specifically, the luminance nonconformance region detector 11111, for each transmission event, acquires acoustic line signal frame data DS1, and detects a luminance nonconformance point LDSij, which is where signal strength of acoustic line signal DSij is equal to or lower than a threshold value, with respect to an observation point Pij in a region of interest ROI. Coordinates ij of a detected observation point LDSij are outputted to the adder 11113. When it is difficult to obtain reflected waves in a portion of tissue of a subject, and an absolute value of a detected acoustic line signal DS is equal to or less than a threshold value, accuracy of detection is low, and it is difficult to calculate displacement from the acoustic line signal by at least a predefined accuracy.

The displacement nonconformance region detector 11112 detects a reliability nonconformance observation point LLij included in a reliability nonconformance region LLR in which data reliability of displacement data PTij in displacement frame data PT1, upon which wavefront arrival time frame data ATo depends, is equal to or below a threshold value. More specifically, the displacement nonconformance region detector 11112, for each transmission event, acquires displacement frame data PT1 and detects a displacement nonconformance point LPTij, which is where an absolute value of displacement of displacement data PTij is equal to or lower than a threshold value, with respect to an observation point Pij in a region of interest ROI. Coordinates ij of a detected displacement nonconformance point LPTij are outputted to the adder 11113. When a portion of hard tissue is present in a subject and an absolute value of displacement data PT detected is small and equal or lower than a threshold value, detection accuracy is low and it is difficult to calculate a wavefront from displacement by at least a predefined accuracy.

The adder 11113 adds coordinates of a luminance nonconformance point LDSij and coordinates of a displacement nonconformance point LPTij to calculates coordinates of a reliability nonconformance observation point LLij, and outputs a region including the reliability nonconformance observation point LLij as a reliability nonconformance region LLR to the wavefront arrival time interpolator 1112.

The wavefront arrival time interpolator 1112 inputs the reliability nonconformance observation point LLij and specifies a reliability nonconformance region LLR in wavefront arrival time frame data ATo. Wavefront arrival time data AT (reliability nonconformance wavefront arrival time data AT) for a reliability nonconformance observation point LLij is interpolated based on wavefront arrival time data AT that satisfies a predefined condition, in order to calculate compensated wavefront arrival time data CATij. Then, compensated wavefront arrival time frame data CATo (where o is a natural number representing a number of a wavefront, and compensated wavefront arrival time frame data CAT is used where wavefront number is not distinguished), which is obtained by replacing reliability nonconformance wavefront arrival time data AT in wavefront arrival time frame data ATo with compensated wavefront arrival time data CATij, is generated and outputted to the data storage 115.

According to the above configuration, it is possible to suppress image omission in an elasticity image in a region in which reliability of measured wavefront arrival time data is low in ultrasound elastic modulus measurement.

As a method of interpolating reliability nonconformance wavefront arrival time data AT, spline interpolation and polygonal line approximation interpolation can be used. Alternatively, a configuration may be adopted in which before and after a shear wave arrives at either side of a region of wavefront arrival time data are considered to be boundary times, and shear wave arrival time is estimated based on boundary detection processing. As a boundary detection processing method, active contour model, dynamic programming, and the like can be used.

6. Elastic Modulus Calculator 112

The elastic modulus calculator 112 is a circuit that calculates propagation speed of a shear wave or elastic modulus for an observation point Pij in a region of interest ROI, and calculates elastic modulus frame data ELF for the region of interest ROI. The elastic modulus calculator 112 is composed of a propagation speed converter 1121 and an elastic modulus converter 1122.

The propagation speed converter 1121 converts wavefront arrival time frame data ATo to propagation speed data Vij at an observation point Pij in a region of interest ROI, and generates and outputs to the data storage 115 propagation speed frame data Vo (where o is a natural number and represents a number of a wavefront, and propagation speed frame data V is used where wavefront number is not distinguished) for the region of interest ROI. When compensated wavefront arrival time frame data CAT is present in plurality, propagation speed frame data VF is calculated by averaging coordinates ij of propagation speed frame data Vo calculated from each compensated wavefront arrival time frame data CATo.

The elastic modulus converter 1122 inputs propagation speed data Vo, converts propagation speed data V to elastic modulus data EL for an observation point Pij in a region of interest ROI, generates elastic modulus frame data ELF for the region of interest ROI, and outputs to the data storage 115.

The elastic modulus calculator 112 outputs generated elastic modulus frame data ELF to the data storage 115 via the controller 116.

8. Other Configuration

The data storage 115 is a storage medium that sequentially stores a generated receive signal series RF, a sequence of acoustic line signal frame data DS1, a sequence of displacement frame data PT1, a sequence of wavefront frame data WF1, wavefront arrival time frame data AT, compensated wavefront arrival time frame data CAT, propagation speed frame data V1, and elastic modulus frame data EL.

The controller 116 controls each block in the ultrasound diagnostic device 100, based on instruction from the operation input unit 102. As the controller 116, a processor such as a CPU can be used.

Further, although not illustrated, the ultrasound diagnostic device 100 has a B mode image generator that generates ultrasound images (B mode images) in a time series based on components reflected from tissue of a subject among ultrasound signals outputted based on transmission and reception of detection waves by the transmitter 106 and the detection wave receiver 108, without transmission of a push wave pulse PPP. The B mode image generator inputs acoustic line signal frame data from the data storage 115, performs processing such as envelope detection and logarithmic compression on the acoustic line signal to convert it to a luminance signal corresponding to intensity thereof, then subjects the luminance signal to coordinate transformation to an orthogonal coordinate system to generate B mode image frame data. Note that ultrasound transmission and reception by the transmitter 106 and the detection wave receiver 108 for acquiring an acoustic line signal for B mode image generation can use a publicly-known method. B mode image frame data is outputted to and stored by the data storage 115. The display controller 113 configures a B mode image as a display image and causes the display 114 to display same.

Further, the elastic modulus calculator 112 may be configured to generate and display an elasticity image mapped to color information based on elastic modulus represented by elastic modulus frame data ELF. For example, an elasticity image may be generated in different colors in which coordinates for which the elastic modulus is equal to or greater than a certain value are red, coordinates for which the elastic modulus is less than the certain value are green, and coordinates for which elastic modulus could not be acquired are black. Thus, convenience for a user can be improved. The elastic modulus calculator 112 outputs generated elastic modulus frame data ELF and an elasticity image to the data storage 115, and the controller 116 outputs the elasticity image to the display controller 113. Further, the display controller 113 performs a geometric transformation on an elasticity image to transform it to image data for display, and outputs the post-transformation elasticity image to the display 114.

Further, the elastic modulus calculator 112 may be configured to generate an elasticity image to display elastic modulus data ELij that depends on compensated wavefront arrival time data CATo in a different mode from elastic modulus data ELij that does not depend on compensated wavefront arrival time data CATo, and the display controller 113 may be configured to cause the display 114 to display compensated elastic modulus data ELij in a different mode from other data. According to the above configuration, a user can recognize that a portion of an elasticity image that depends on compensated wavefront arrival time data is a region of lower reliability that measured wavefront arrival time data, improving convenience for the user.

<Operations>

The following describes operations of an integrated SWS sequence of the ultrasound diagnostic device 100 configured as described above.

1. Operation Outline

Figure 9:
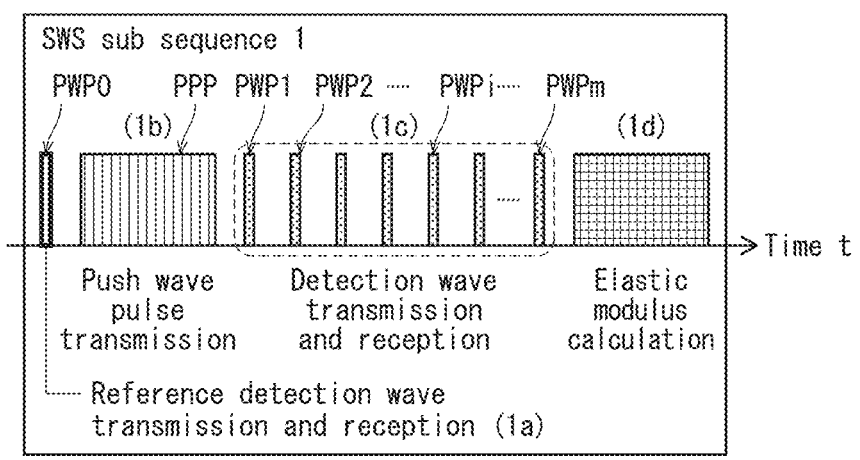
FIG. 9 is a schematic diagram showing an outline of a process of an integrated SWS sequence in ultrasound diagnostic device 100.

FIG. 9 is a schematic diagram showing an outline of a process of an integrated SWS sequence in the ultrasound diagnostic device 100. An SWS sequence by the ultrasound diagnostic device 100 includes a step (1a) of reference detection wave transmission and reception, acquiring reference acoustic line signal frame data DS0 for extracting displacement due to a shear wave corresponding to each subsequent transmission event; a step (1b) of transmitting a push wave pulse PPP to transmit a push wave PP that converges on a specific site F in a subject, in order to excite a shear wave in the subject; a step (1c) of repeated (m) times transmission and reception of a detection wave pulse PWP1 for detection wave PW1 transmission and reception through a region of interest ROI; and a step (1d) of elastic modulus detection for calculating shear wave propagation speed VF and elastic modulus ELF by shear wave propagation analysis.

2. SWS Sequence Operation

The following describes an operation of ultrasound elastic modulus measurement processing after a B mode image is displayed on the display 114, in which tissue is drawn based on reflection components from tissue of a subject based on a publicly-known method.

B mode image frame data is generated without transmission of a push wave pulse PPP, and acoustic line signal frame data thereof is generated in a time series based on reflected components from tissue of a subject, based on transmission and reception of ultrasound by the transmitter 106 and the detection wave receiver 108, the acoustic line signal then being subjected to processing such as envelope detection, logarithmic compression, and the like, converting it into a luminance signal, then subjecting the luminance signal to coordinate transformation to an orthogonal coordinate system. The display controller 113 causes the display 114 to display a B mode image in which tissue of a subject is drawn.

Figure 10:
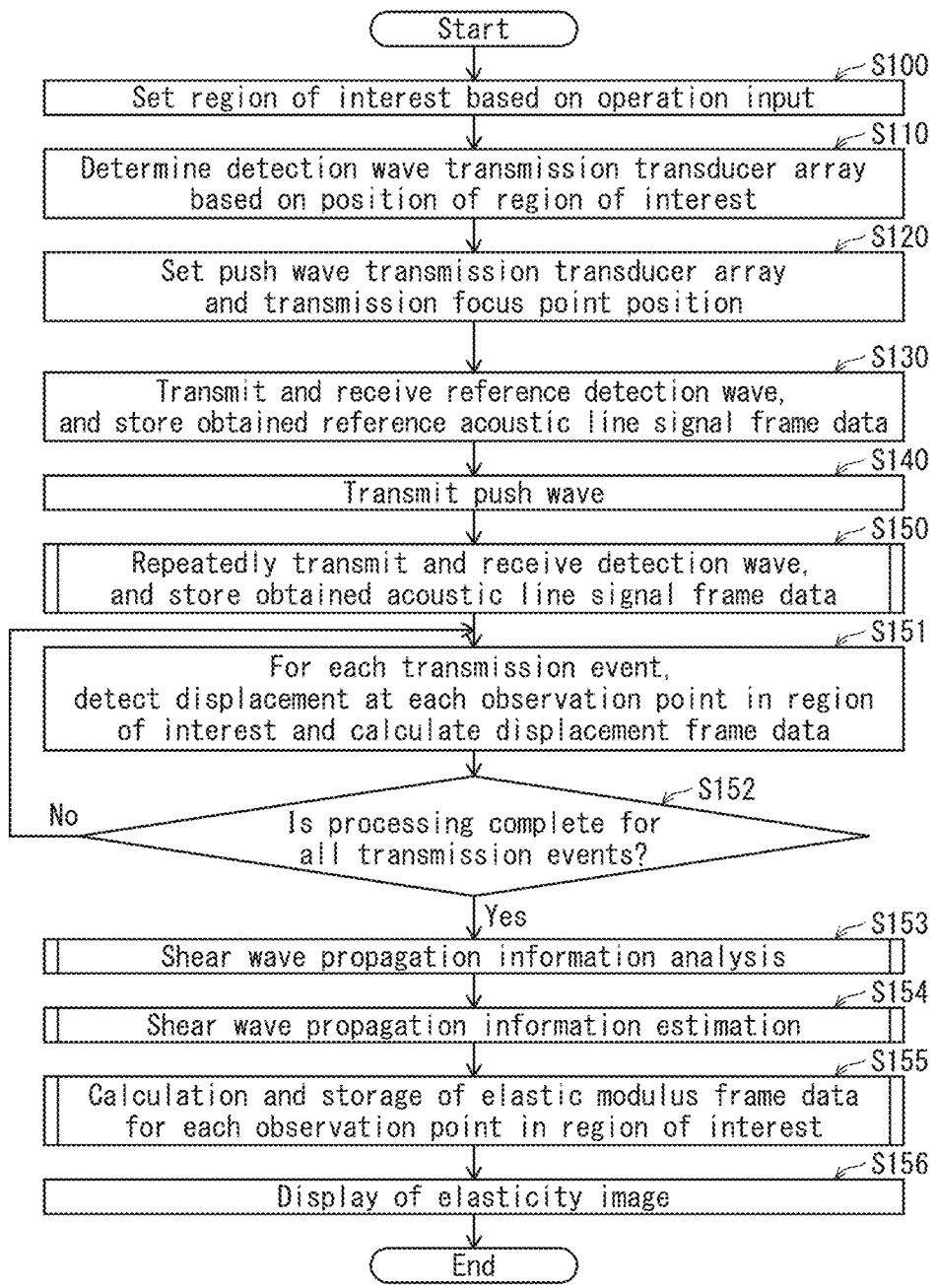
FIG. 10 is a flowchart showing an operation of ultrasound elastic modulus calculation of ultrasound diagnostic device 100.

FIG. 10 is a flowchart showing an operation of ultrasound elastic modulus calculation of the ultrasound diagnostic device 100.

[Steps S100 to S140]

In step S100, in a state in which a B mode image, which is a tomographic image of a subject acquired in real time by the probe 101 is displayed on the display 114, the region of interest setter 103 inputs information designated by a user via the operation input unit 102 in order to set a region of interest ROI representing an analysis target range in the subject using position of the probe 101 as a reference, and outputs the region of interest ROI to the controller 116.

Designation of a region of interest ROI by a user is performed, for example, by display on the display 114 of a latest B mode image stored in the data storage 115, and designating the region of interest ROI through an input unit (not illustrated) such as a touch panel or mouse. A region of interest ROI may, for example, be an entire region of a B mode image, or it may be a fixed range including a central portion of the B mode image.

In step S120, the push wave pulse generator 104 inputs information indicating a region of interest ROI from the controller 116, sets position of a transmission focus point F of a push wave pulse PPP, and sets a push wave transmission transducer array Px. According to the present example, as shown in FIG. 3B, row direction transmission point position Fx coincides with row direction center position WC of detection wave irradiation region Ax, and depth direction transmission focus point position Fz coincides with depth d to a center of the detection wave irradiation region Ax. Further, a push wave transmission transducer array Px is all of the transducers 101a. However, positions of the detection wave irradiation region Ax and the transmission focus point F relative to each other are not limited to the above example, and may be appropriately changed according to form of a site to be examined in a subject, or for other reasons.

Position of the transmission focus point F and information indicating the push wave transmission transducer array Px, together with pulse width of the push wave pulse PPP, are outputted to the transmitter 106 as a transmission control signal.

In step S130, the transmitter 106 transmits a detection wave pulse PWP0 to a transducer included in a detection wave transmission transducer array Tx, causing transmission of a detection wave PW0 into a subject, and the detection wave receiver 108 receives a reflected wave ec of the detection wave PW0 and generates reference acoustic line signal frame data DS0, which is a reference for tissue displacement. Reference acoustic line signal frame data DS0 is outputted to and stored by the data storage 115. Generation of acoustic line signal frame data is described later.

In step S140, the transmitter 106 causes transmission of a push wave pulse PPP to transducers included in a push wave transmission transducer array Px, thereby causing the transducers to transmit a push wave PP, which is a convergence of ultrasound beams to a specific site in a subject corresponding to the transmission focus point F.

More specifically, the transmitter 106 generates a transmission profile based on a transmission control signal composed of information indicating position of the transmission focus point F and the push wave transmission transducer array Px acquired by the push wave pulse generator 104 and pulse width of the push wave pulse PPP. A transmission profile is composed of pulse signal SP and delay time TPk with respect to each transmission transducer included in the push wave transmission transducer array Px. Thus, a push wave pulse PPP is supplied to each transmission transducer based on a transmission profile. Each transmission transducer transmits a push wave PP that is pulsed and converges to a specific site in a subject.

Figure 11A:
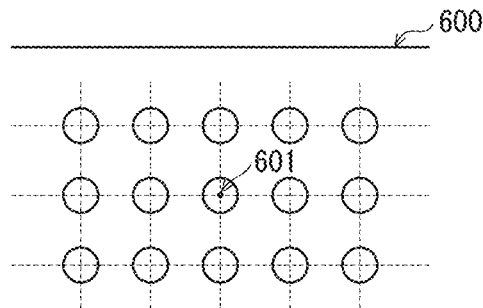
FIG. 11A to FIG. 11E are schematic diagrams showing how a shear wave is generated by a push wave PP.

Here, generation of a shear wave by a push wave PP is described with reference to schematic diagrams FIG. 11A to FIG. 11E. FIG. 11A to FIG. 11E are schematic diagrams showing how a shear wave is generated by a push wave PP. FIG. 11A is a schematic diagram showing tissue prior to application of a push wave PP in a region in a subject corresponding to a detection wave irradiation region Ax. In FIG. 11A to FIG. 11E, each "○" indicates a portion of tissue in a subject, which is centered on an intersection of dashed lines when not under load.

Figure 11B:
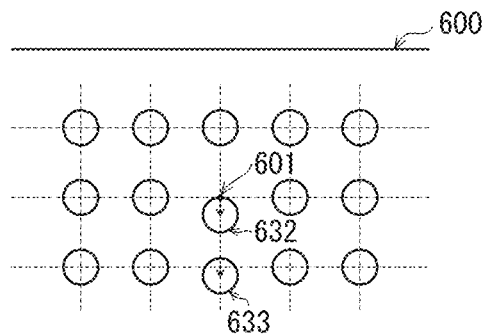

Here, when the probe 101, in close contact with a skin surface 600, applies a push wave PP to a focus site 601 in the subject, which corresponds to the transmission focus point F, tissue 632 at the focus site 601 is pushed and moved in a travel direction of the push wave PP, as shown in the schematic diagram of FIG. 11B. Further, tissue 633, which is in the travel direction of the push wave PP from the tissue 632, is pushed by the tissue 632 and moves in the travel direction of the push wave PP.

Figure 11C:
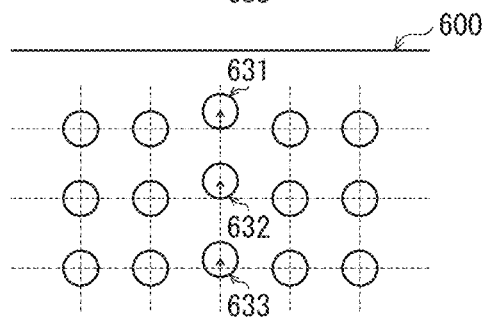

Subsequently, when transmission of the push wave PP ends, the tissues 632, 633 attempt to return to their original positions, and therefore tissue 631, the tissue 632, and the tissue 633 start vibrating along the travel direction of the push wave PP, as shown in the schematic diagram of FIG. 11C.

Figure 11D:
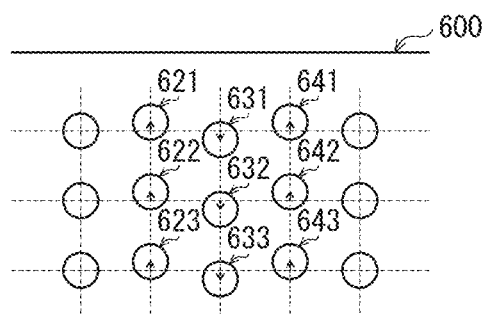

As shown in the schematic diagram of FIG. 11D, vibrations propagate to tissues 621, 622, 623 and tissues 641, 642, 643, which are adjacent to the tissues 631, 632, 633.

Figure 11E:
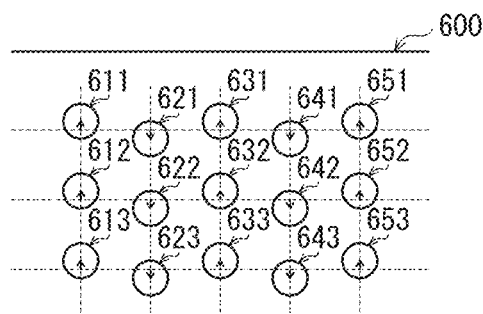

Further, as shown in the schematic diagram of FIG. 11E, vibrations further propagate to tissues 611, 612, 613 and tissues 651, 652, 653. Accordingly, in the subject, vibrations propagate in a direction perpendicular to the direction of vibration. In other words, a shear wave is generated at a point of application of the push wave PP, and propagates in the subject.

[Step S150]

Description continues with reference to FIG. 10.

In step S150, a detection wave pulse PWP1 is repeatedly transmitted, and transmission and reception to the region of interest ROI is used to generate and stores a sequence of acoustic line signal frame data DS1. More specifically, the transmitter 106 transmits detection wave pulses PWP1 to cause transducers included in the detection wave transmission transducer array Tx to transmit detection waves PW1 into the subject, and the detection wave receiver 108 generates acoustic line signal frame data DS1 based on reflected waves EC received by transducers included in the detection wave receive transducer array Rx. Immediately after transmission of a push wave PP ends, the above process is repeated 10,000 times per second, for example. Thus, acoustic line signal frame data DS1 for the detection wave irradiation region Ax of a subject is repeatedly generated immediately after generation of a shear wave and until propagation ends. A sequence of acoustic line signal frame data DS1 is outputted to and stored by the data storage 115.

A method of generating acoustic line signal frame data DS1 in step S150 is described in detail later.

[Step S151]

In step S151, the displacement detector 109 detects displacement of an observation point Pij in the region of interest ROI for each transmission event.

Figure 12:
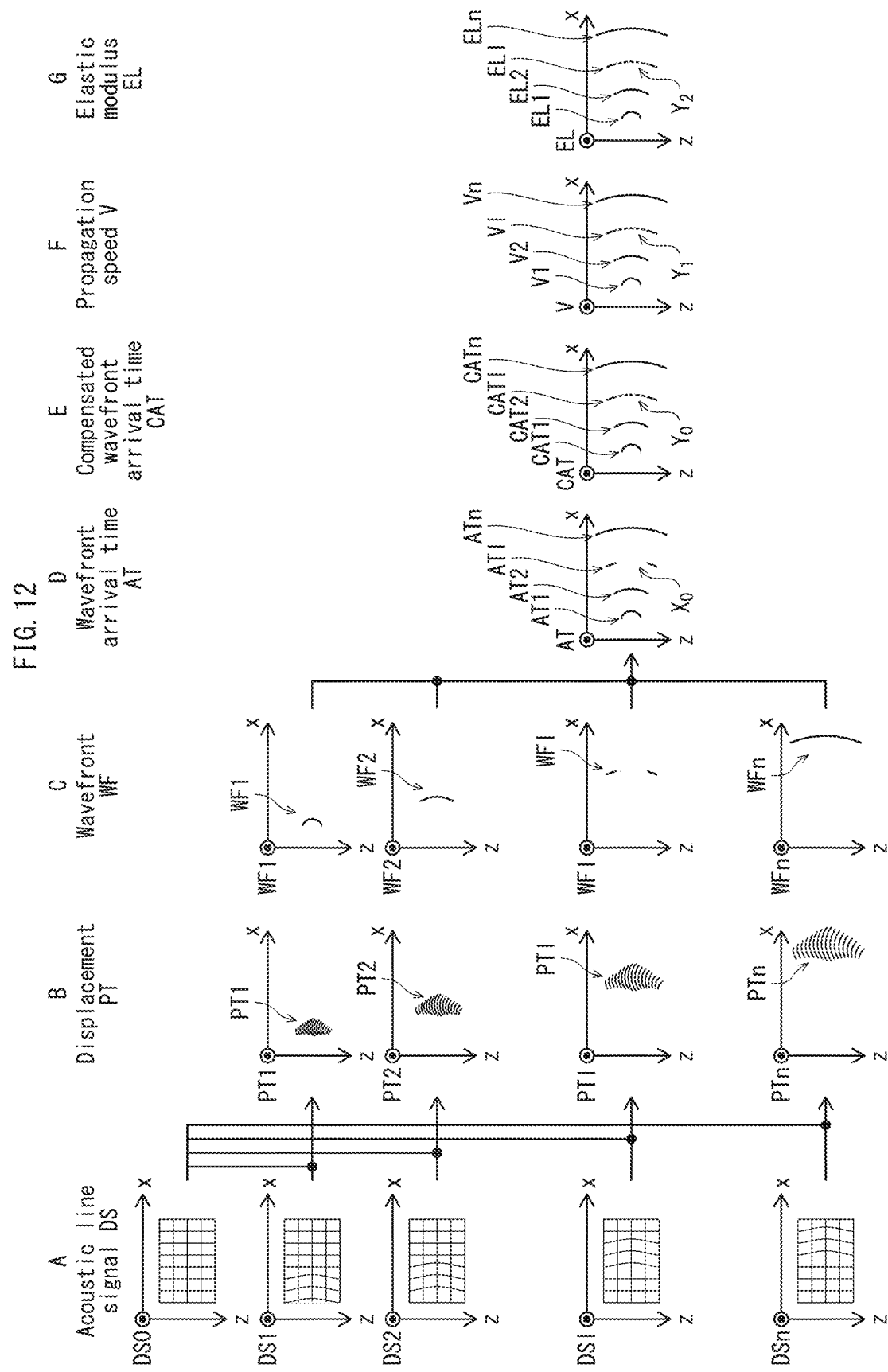
FIG. 12 is a schematic diagram illustrating operations of displacement detection and shear wave propagation analysis.

FIG. 12 is a schematic diagram illustrating operations of displacement detection and shear wave propagation analysis.

First, the displacement detector 109 acquires reference acoustic line signal frame data DS0 stored in the data storage 115 in step S130. As above, reference acoustic line signal frame data DS0 is acoustic line signal frame data acquired prior to push wave PP transmission, that is, prior to shear wave generation.

Next, the displacement detector 109 detects displacement of pixels at a time of acquisition of acoustic line signal frame data DS1, from differences from reference acoustic line signal frame data DS0, with respect to each acoustic line signal frame data DS1 stored in the data storage 115 in step S150.

Column A in FIG. 12 shows reference acoustic line signal frame data DS0 and acoustic line signal frame data DS1 generated for each transmission event, while column B shows displacement frame data PT1 calculated for each transmission event. As shown in column A and column B in FIG. 12, displacement frame data PT1 is calculated by comparing acoustic line signal frame data DS1 to reference acoustic line signal frame data DS0, and detecting which acoustic line signal DSij of an observation point P'ij in acoustic line signal frame data DS1 an acoustic line signal DSij of an observation point Pij in reference acoustic line signal frame data DS0 is similar to, in order to calculate displacement of an observation point P'ij relative to an observation point Pij.

More specifically, acoustic line signal frame data DS1 is divided into regions of predefined size such as eight pixels by eight pixels, each region is pattern matched to reference acoustic line signal frame data DS0, and displacement of each pixel of acoustic line signal frame data DS1 is thereby detected.

As a method of pattern matching, a method can be used in which, for each region, differences in luminance values are calculated for each pixel with respect to a reference region of the same size in reference acoustic line signal frame data DS0, then absolute values obtained are summed, then a region and a reference region that have a lowest total value are assumed to be the same region, and a difference between a reference point (for example, a top-left corner) of the region and a reference point of the reference region is calculated as displacement.

Size of a region may be a size other than eight pixels by eight pixels, and instead of a sum of absolute values of luminance differences a sum of squared luminance differences may be used. Further, as displacement, a difference in z coordinates (difference in depth) may be calculated between a reference point of a region and a reference point of a reference region. Thus, with respect to tissue of a subject corresponding to observation points Pij of each acoustic line signal frame data DS1, how far the tissue moves due to a push wave PP or shear wave is calculated as displacement.

Note that methods of displacement detection are not limited to pattern matching. Any technique may be used for detecting motion between two sequences of acoustic line signal frame data DS1, such as correlation processing between acoustic line signal frame data DS1 and reference acoustic line signal frame data DS0 for example. The displacement detector 109 generates displacement data PTij of an observation point in a region of interest ROI by associating coordinates ij with displacement of an observation point Pij pertaining to one frame of acoustic line signal frame data DS1, and outputs displacement frame data PT1 for the region of interest ROI to the data storage 115.

[Steps S152 to S155]

The propagation information analyzer 110 outputs displacement frame data PT1 to the data storage 115 (step S173). Then the propagation information analyzer 110 determines whether or not processing of step S151 is complete for all defined transmission events (step S152); when incomplete, processing returns to step S151 and processing continues for the transmission event of the next detection wave pulse PWP1; and when complete, processing proceeds to step S153.

In step S153, the propagation information analyzer 110 inputs a sequence of displacement frame data PT1, detects a wavefront of a shear wave from displacement data PTij of observation points Pij in the region of interest ROI for each transmission event, and generates a sequence of wavefront frame data WF1 representing wavefront positions WFij. Further, the propagation information analyzer 110 detects a wavefront WF and position WFij of a shear wave at each time displacement frame data PT1 is acquired from a sequence of wavefront frame data WF1, generates wavefront arrival time frame data ATo for each wavefront, and outputs same to the data storage 115. Details of shear wave propagation information analysis method in step S153 are provided later.

In step S154, the propagation information estimator 111 inputs wavefront arrival time frame data ATo, evaluates reliability of wavefront arrival time data ATij, detects reliability nonconformance wavefront arrival time data ATij for which an indicator of reliability is equal to or below a threshold and does not satisfy a predefined condition, and generates compensated wavefront arrival time data CATij by interpolation of reliability nonconformance wavefront arrival time data ATij based on wavefront arrival time data ATij that satisfies a predefined condition. The propagation information estimator then generates compensated wavefront arrival time frame data CATo in which reliability nonconformance wavefront arrival time data ATij is replaced by compensated wavefront arrival time data CATij, and outputs same to the data storage 115. Details of shear wave propagation information estimation method in step S154 are provided later.

In step S155, the elastic modulus calculator 112 calculates shear wave propagation speed data Vij or elastic modulus data ELij for an observation point Pij in the region of interest ROI, calculates elastic modulus frame data ELF for the region of interest ROI, and outputs same to the data storage 115. Details of calculation of elastic modulus frame data ELF in step S155 are provided later.

In step S156, the elastic modulus calculator 112 generates an elasticity image mapped with color information, based on elastic modulus represented by elastic modulus frame data ELF; and the display controller 113 performs a geometric transformation on the elasticity image to generate image data for screen display, and outputs a geometrically transformed elasticity image to the display 114.

This completes SWS sequence processing shown in FIG. 10. According to the ultrasound elastic modulus measurement processing above, elastic modulus frame data ELF according to a SWS sequence can be calculated.

3. Details of Processing in Step S153.

In step S153, the propagation information analyzer 110 detects a wavefront from displacement frame data PT1 of an observation point Pij in a region of interest ROI in each transmission event.

Figure 13:
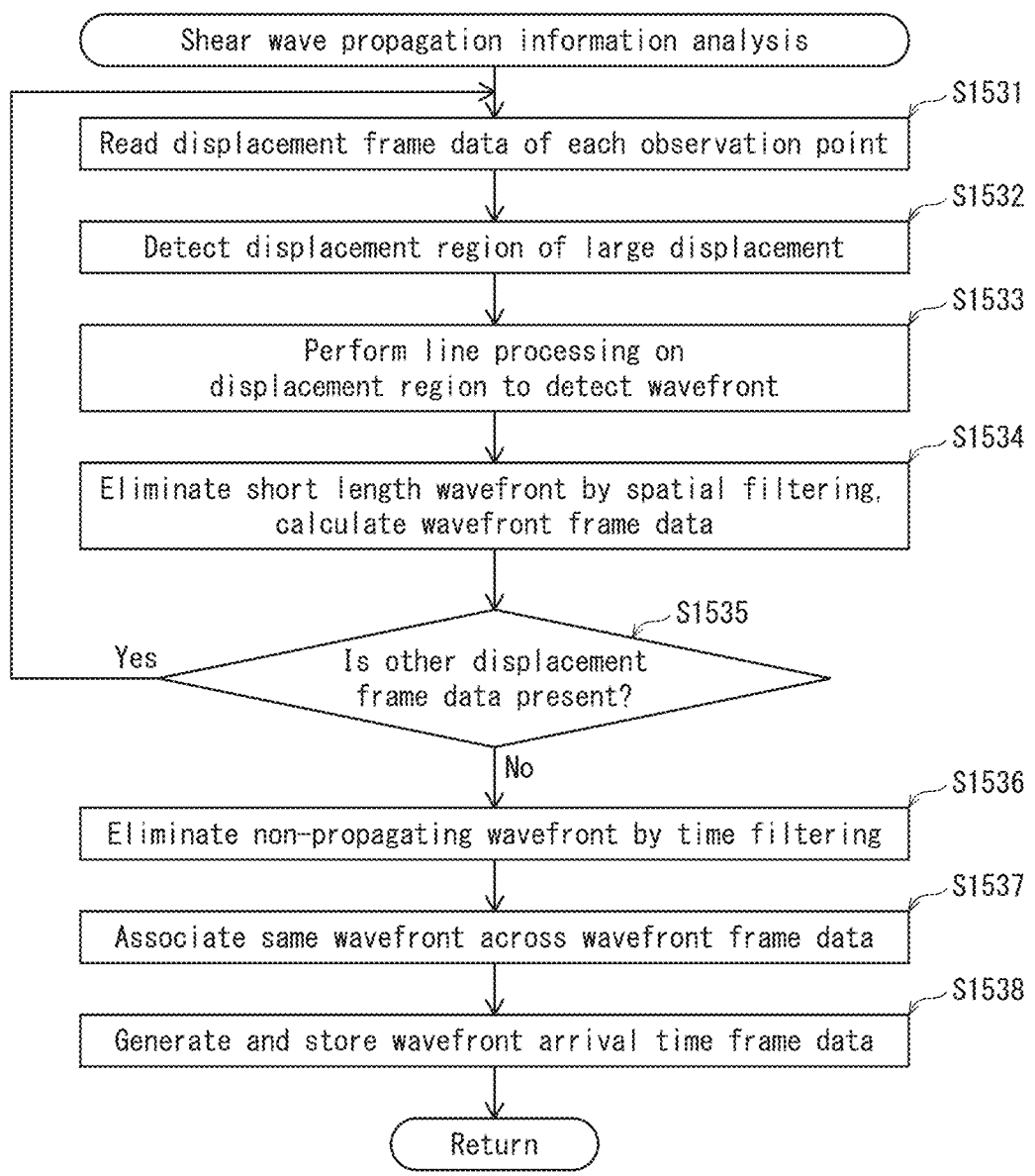
FIG. 13 is a flowchart showing an operation of shear wave propagation information analysis of ultrasound diagnostic device 100.

Details are described with reference to the flowchart of FIG. 13. FIG. 13 is a flowchart showing an operation of shear wave propagation information analysis. FIG. 14A to FIG. 14F are schematic diagrams showing an operation of shear wave propagation analysis.

Initially, displacement frame data PT1 for each observation point Pij corresponding to a transmission event is acquired from the data storage 115 (step S1531).

Next, a displacement region of relatively large displacement is extracted (step S1532). The propagation information analyzer 110 extracts a displacement region from displacement frame data PT1 in which displacement is greater than a predefined threshold.

The following description references FIGS. 14A, 14B, 14C, 14D, 14E, and 14F.

Figure 14A:
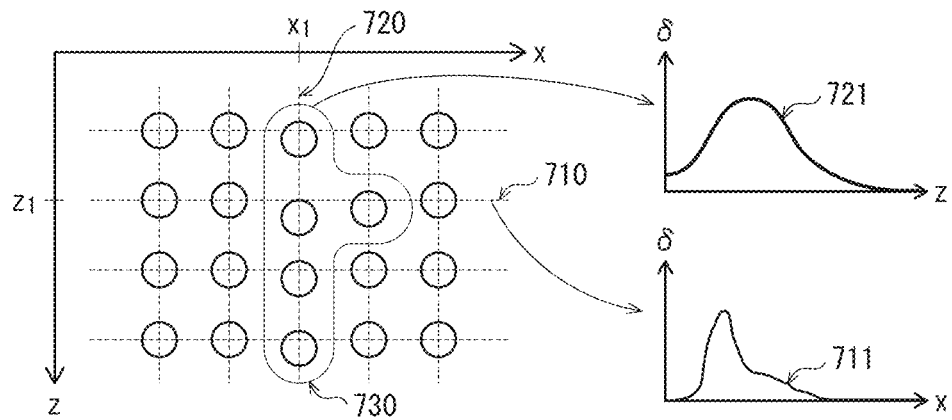
FIG. 14A to FIG. 14F are schematic diagrams showing an operation of shear wave propagation analysis.

FIG. 14A shows an example of a displacement image represented by displacement frame data. As in FIG. 11A to 11E, each "o" in the drawing indicates a portion of tissue in a subject corresponding to a region of interest ROI, a position of which is centered on an intersection of dashed lines prior to application of a push wave PP. Further, the x axis is a row direction of transducers of the probe 101 and the z axis is a depth direction of a subject. The propagation information analyzer 110 treats a displacement amount $\delta$ for each z coordinate as a function of coordinates x, and extracts a region for which a displacement amount $\delta$ is large, by using a dynamic threshold. Further, treating a displacement amount $\delta$ for each x coordinate as a function of coordinates z, and using a dynamic threshold, a region that exceeds a threshold is extracted as a region for which displacement amount $\delta$ is large. Here, a dynamic threshold is determined by performing signal analysis or image analysis of a target region. The threshold is not a fixed value, but varies according to factors such as width and maximum value of a signal of a target region. FIG. 14A illustrates a graph 711 in which displacement is plotted on a straight line 710 for which $z=z_1$, and a graph 721 in which displacement is plotted on a straight line 720 for which $x=x_1$. Thus, for example, a displacement region 730 in which a displacement amount $\delta$ is greater than a threshold can be extracted.

Further, column B of FIG. 12 shows displacement frame data PT1 calculated for each transmission event, and a hatched region in each displacement frame data PT1 indicates a region in which displacement amount $\delta$ is larger than a threshold. As shown in column B of FIG. 12, as time passes a displacement region moves in the X direction and increases in size.

Figure 15A:
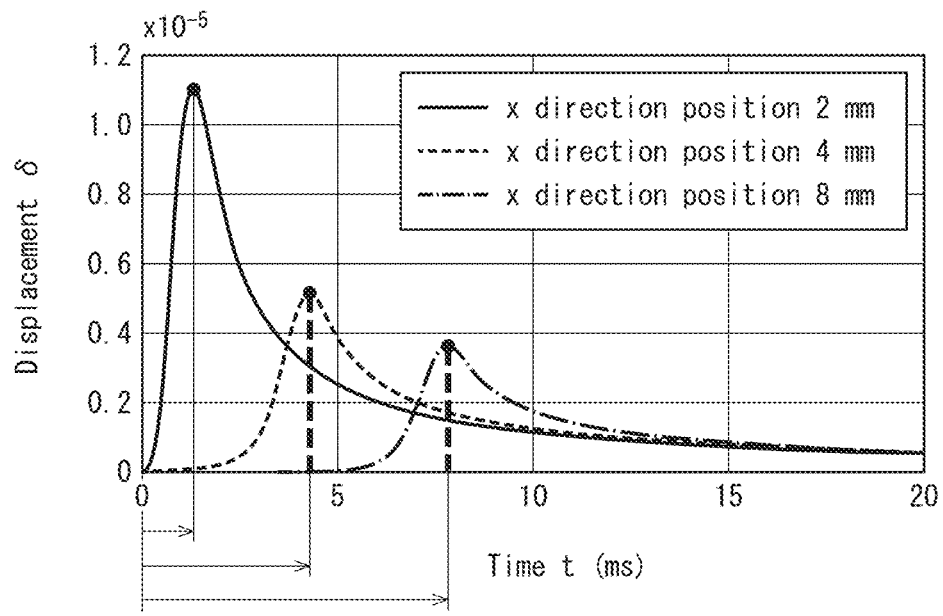
FIG. 15A and FIG. 15B are schematic diagrams showing shear wave propagation states.

FIG. 15A is a schematic diagram showing shear wave propagation in which the horizontal axis is time and the vertical axis is displacement, and experimental results show changes over time of displacement amount $\delta$ at positions 2 mm, 4 mm, and 8 mm in the X direction. It can be seen that as time passes, a displacement region moves in the X direction, peak displacement decreases, and the displacement region increases in size.

Figure 14B:
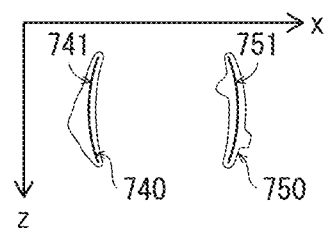
Figure 14C:
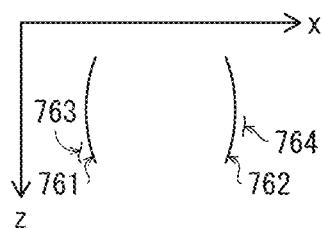
Figure 14D:
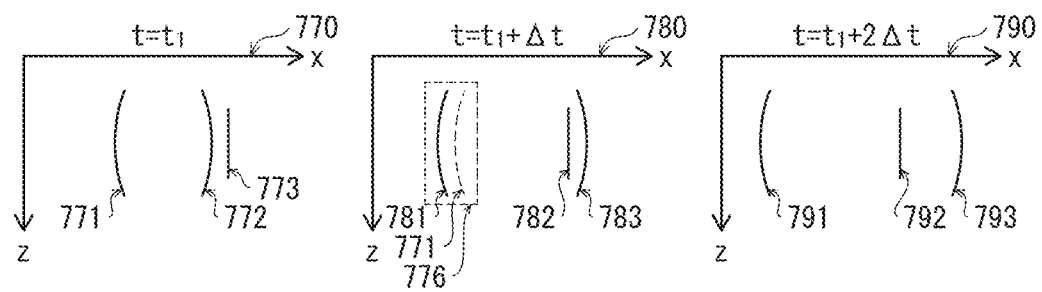

Next, the propagation information analyzer 110 extracts a wavefront by performing a thinning process on the displacement region (step S1533). Displacement regions 740, 750 shown in the schematic diagram of FIG. 14B are each a region extracted as a displacement region 730 in step S1532. The propagation information analyzer 110 extracts a wavefront by using, for example, the thinning algorithm of Hilditch. For example, in the schematic diagram of FIG. 14B, a wavefront 741 is extracted from the displacement region 740 and a wavefront 751 is extracted from the displacement region 750. Note that the thinning algorithm is not limited to Hilditch, and any thinning algorithm may be used. Further, for each displacement region, a process of removing coordinates for which a displacement amount $\delta$ is equal to or less than a threshold may be repeated while increasing the threshold until width of the displacement region is a single pixel. The propagation information analyzer 110 outputs an extracted wavefront as wavefront frame data WF1 to the data storage 115.

Next, the propagation information analyzer 110 performs spatial filtering on the wavefront frame data WF1 to eliminate short wavefronts (step S1534). For example, length of each wavefront extracted in step S1533 is extracted, and a wavefront that has a length less than half of the average length of all wavefronts is eliminated. More specifically, as indicated in the wavefront image of FIG. 14C, the propagation information analyzer 110 calculates the average length of wavefronts 761, 762, 763, 764, and eliminates as noise the wavefronts 763 and 764, which each have a shorter length than the average length. Thus, erroneously detected wavefronts can be eliminated.

The propagation information analyzer 110 performs the operations of steps S1531 to S1534 with respect to all of displacement frame data PT1 (step S1535). Thus, wavefront frame data WF1 is generated one-to-one with respect to displacement frame data PT1.

Column C of FIG. 12 shows wavefront frame data WF1 calculated for each transmission event, in which each arc-shaped fine line in wavefront frame data WF1 is a wavefront. As shown in column C of FIG. 12, as time elapses a wavefront WF moves in the X direction and length of its arc increases.

Next, the propagation information analyzer 110 performs time filtering on the wavefront frame data WF1 to eliminate non-propagating wavefronts (step S1536). More specifically, with respect to two or more temporally consecutive wavefront frame data WF1, a change over time in wavefront position is detected, and a wavefront for which speed is abnormal is eliminated as noise.

The propagation information analyzer 110, for example, detects changes in wavefront positions over time between a wavefront image 770 at time $t=t_1$, a wavefront image 780 at time $t=t_1+\Delta t$, and a wavefront image 790 at time $t=t_1+2\Delta t$. For example, with respect to wavefront 771, in wavefront image 780, the propagation information analyzer 110 performs a correlation process in a region 776 that is centered on a position corresponding to the wavefront 771, the region 776 covering an area in which a shear wave could possibly move in the time period $\Delta t$ in directions perpendicular to the wavefront, i.e., the x axis direction in FIG. 14D. Thus, the correlation process is performed in a range that includes both a positive x axis direction (right in FIG. 14D) and a negative x axis direction (left in FIG. 14D) from the wavefront 771. This is to detect both transmitted and reflected waves. Thus, the propagation information analyzer 110 detects that a movement destination of the wavefront 771 is a wavefront 781 in the wavefront image 780, and calculates a movement distance of the wavefront 771 over the time period $\Delta t$. In the same way, with respect to wavefronts 772 and 773, in the wavefront image 780, the propagation information analyzer 110 performs a correlation process in regions that are centered on positions corresponding to each wavefront, covering areas in which a shear wave could possibly move in the time period $\Delta t$ in directions perpendicular to the wavefronts. Thus, the propagation information analyzer 110 detects that the wavefront 772 moves to a position of a wavefront 783 and the wavefront 773 moves to a position of a wavefront 782.

The same processing is performed for wavefront image 780 and wavefront image 790, detecting movement of wavefront 781 to a position of wavefront 791, wavefront 782 to a position of wavefront 797, and wavefront 783 to a position of wavefront 793. Here, the single wavefront indicated by the wavefront 773, the wavefront 782, and the wavefront 792 has a significantly shorter travel distance than other wavefronts, i.e. a significantly slower propagation speed. Such a wavefront is most likely a false positive, and is therefore eliminated as noise. Thus, as shown in wavefront frame data 300 of FIG. 14E, wavefronts 801 and 802 can be detected.

According to these operations, a sequence of wavefront frame data WF1 over time can be generated. The propagation information analyzer 110 outputs a generated sequence of wavefront frame data WF1 to the data storage 115. Here, generated wavefront correspondence information may be outputted to the data storage 115 (step S1537). Here, correspondence information means information indicating which wavefront in each wavefront image a given wavefront corresponds to. For example, when it is detected that the wavefront 772 moves to the position of the wavefront 783, the correspondence information indicates that the wavefront 783 and the wavefront 772 are the same wavefront.

Next, the propagation information analyzer 110 generates wavefront arrival time frame data AT (step S1538). More specifically, the propagation information analyzer 110 detects wavefront position, speed, and relationship therebetween for each time, from the wavefront frame data WF1 and the correspondence information.

Figure 14E:
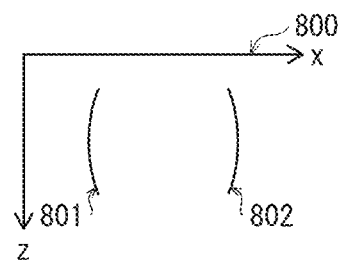

Generation of wavefront arrival time frame data AT is described with reference to FIG. 14E. FIG. 14E shows wavefront frame data WF1 at a time t and wavefront frame data WF1 at a time $t+\Delta t$ combined as wavefront frame data 810. Here, it is assumed that correspondence information exists that indicates that a wavefront 811 at time t and a wavefront 812 at time $t+\Delta t$ are the same wavefront. The propagation information analyzer 110 detects coordinates of the wavefront 812 $(x_t+\Delta_t, z_t+\Delta_t)$ that correspond to coordinates of the wavefront 811 $(x_t, z_t)$. Thus, the propagation information analyzer 110 can estimate that a shear wave that passes through coordinates $(x_t, z_t)$ at time t arrives at coordinates $(x_t+\Delta_t, z_t+\Delta_t)$ at time $t+\Delta t$. Thus, a relationship can be established between a time t when wavefront 811 reaches coordinates $(x_t, z_t)$ and a time $t+\Delta t$ when wavefront 812, which is the same wavefront, reaches coordinates $(x_t+\Delta_t, z_t+\Delta_t)$. Similarly, a time at which a wavefront arrives at arbitrary coordinates (x, z) from a wavefront position detected from wavefront frame data WF1 acquired at a predefined time can be calculated by two-dimensional interpolation calculation.

Column D of FIG. 12 shows wavefront arrival time frame data AT, in which wavefronts WF in wavefront frame data WF1 calculated for each transmission event are collected in one frame, and plotted using a time of acquisition of each wavefront frame data WF1 as a function value, with each arc-shaped fine line in the wavefront arrival time frame data AT representing wavefront arrival time.

Figure 15B:
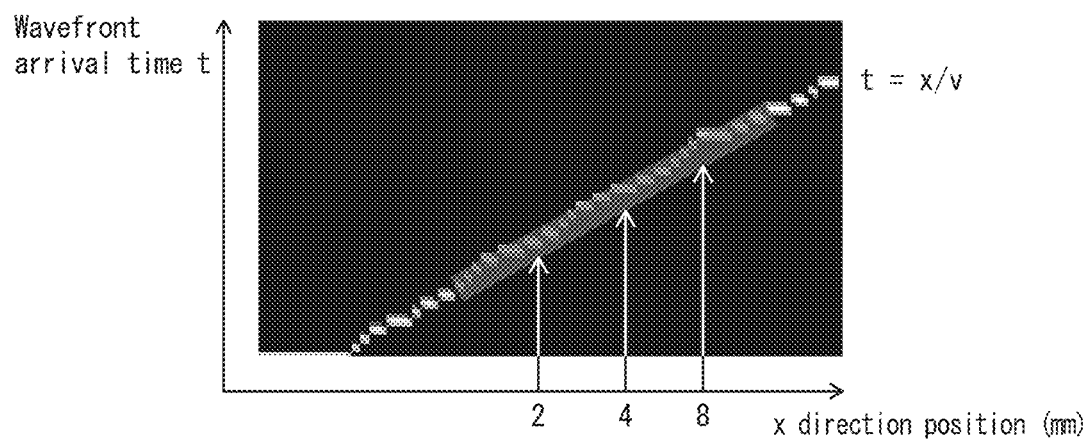

Further, FIG. 15B is a schematic diagram showing shear wave propagation, in which the horizontal axis is an x direction position and the vertical axis is wavefront arrival time, showing experiment results indicating wavefront arrival time at positions 2 mm, 4 mm, and 8 mm along the x direction. As x direction position increases, wavefront arrival time increases linearly, and it can be seen that the wavefront propagates at a constant speed V.

4. Details of Processing in Step S154.

In step S154, the propagation information estimator 111 inputs wavefront arrival time frame data ATo, evaluates reliability of wavefront arrival time data ATij, and generates compensated wavefront arrival time frame data CATo in which reliability nonconformance wavefront arrival time data ATij is replaced by compensated wavefront arrival time data CATij.

Figure 16:
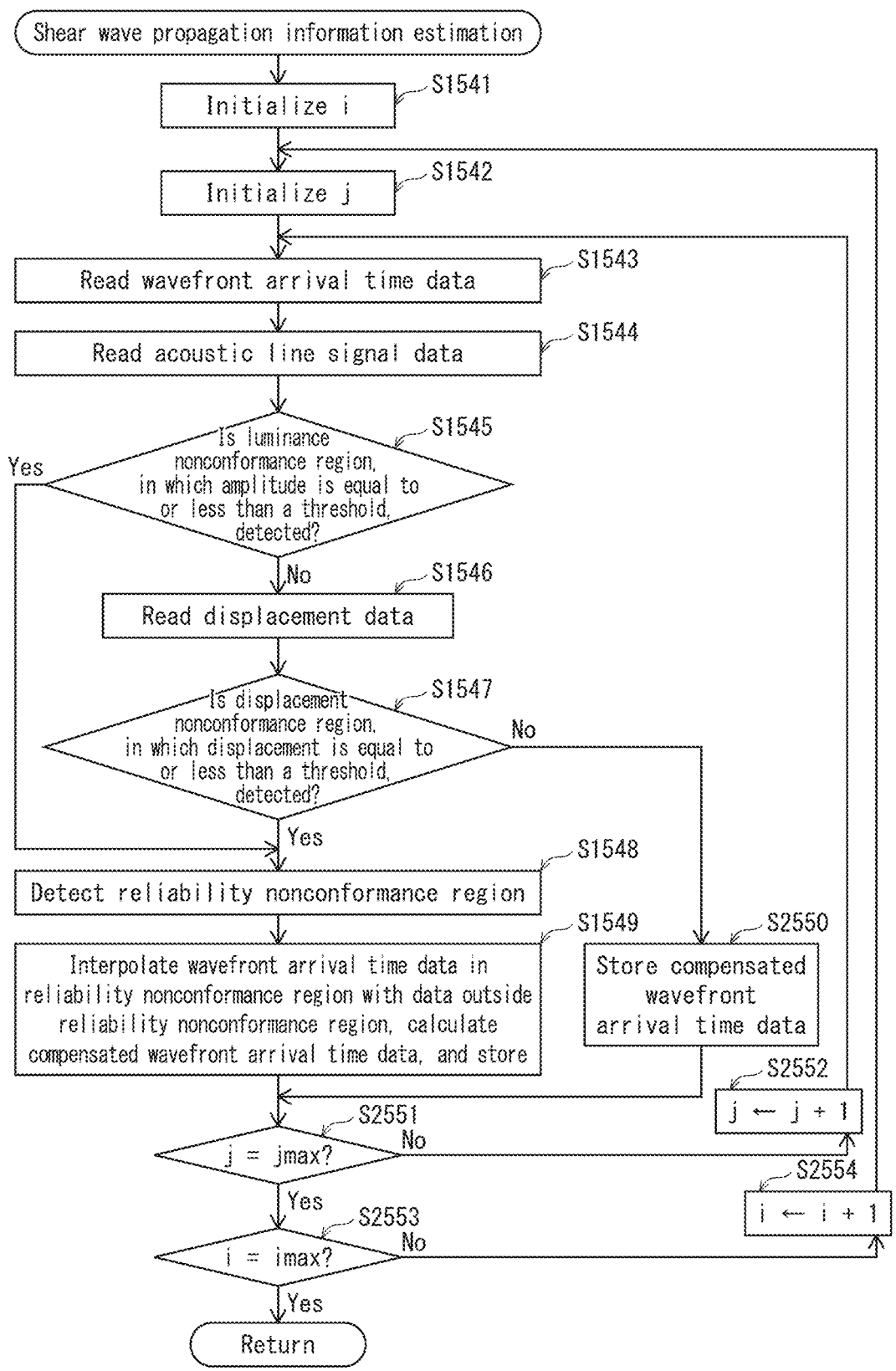
FIG. 16 is a flowchart showing an operation of shear wave propagation information estimation of ultrasound diagnostic device 100.

Details are described with reference to the flowchart of FIG. 16. FIG. 16 is a flowchart showing an operation of shear wave propagation information estimation.

Initially, j and i are initialized to minimum values in region of interest ROI (step S1541, S1542). The propagation information estimator 111 acquires, from the data storage 115, wavefront arrival time data ATij for an observation point Pij corresponding to a transmission event (step S1543).

Next, the propagation information estimator 111 acquires, from the data storage 115, an acoustic line signal DSij of the observation point Pij corresponding to the transmission event (step S1544), and determines whether or not the acoustic line signal DSij is a luminance nonconformance point LDSij in which an absolute value of signal strength is equal to or less than a threshold (step S1545). When greater than the threshold, processing proceeds to step S1546, and when equal to or less than the threshold, processing proceeds to step S1550.

Next, the propagation information estimator 111 acquires, from the data storage 115, displacement data PTij of the observation point corresponding to the transmission event (step S1546), and determines whether or not the displacement data PTij is a displacement nonconformance point LPTij in which an absolute value is equal to or less than a threshold (step S1547). When greater than the threshold, processing proceeds to step S1550, and when equal to or less than the threshold, processing proceeds to step S1548.

In step S1548, the propagation information estimator 111 detects a luminance nonconformance point LDSij that does not satisfy a predefined luminance condition or a displacement nonconformance point LPTij that does not satisfy a predefined displacement condition as a reliability nonconformance observation point LLij; interpolates wavefront arrival time data AT at a reliability nonconformance observation point LLij (reliability nonconformance wavefront arrival time data AT) based on wavefront arrival time data AT that satisfies a predefined condition in order to calculate compensated wavefront arrival time data CATij; and outputs same to the data storage 115 (step S1549). As a method of interpolating reliability nonconformance wavefront arrival time data AT, spline interpolation and polygonal line approximation interpolation can be used.

Figure 17A:
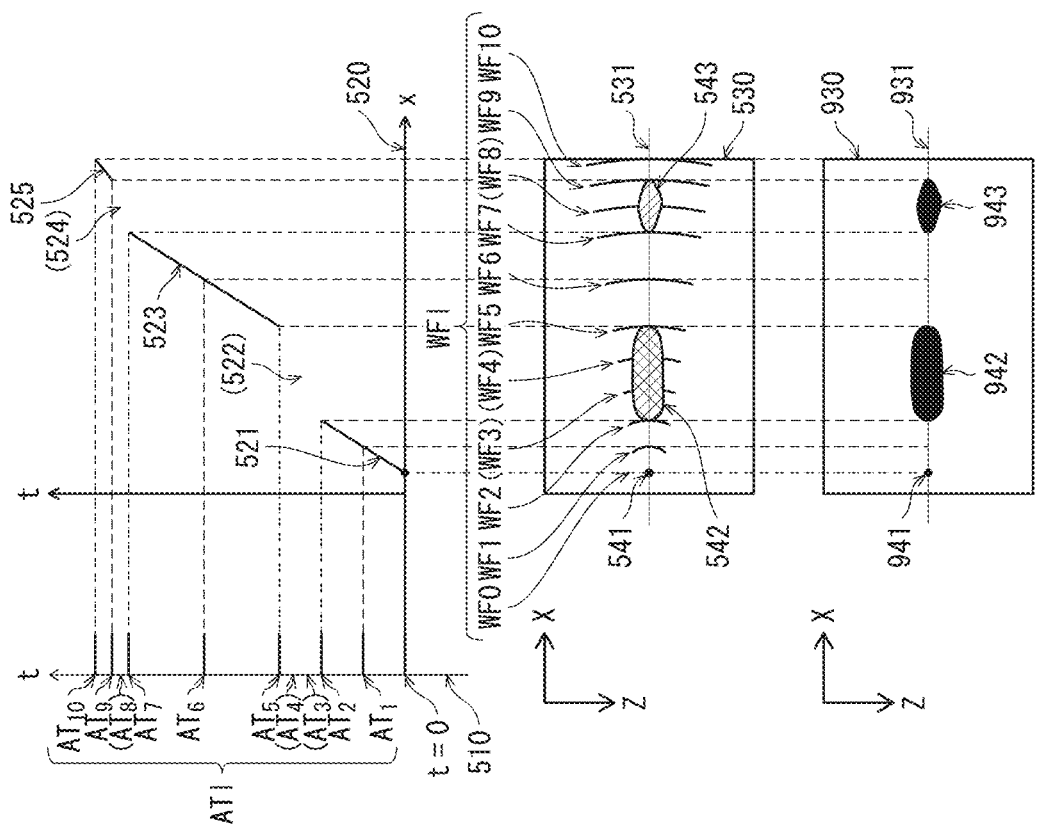
FIG. 17A and FIG. 17B are schematic diagrams showing shear wave propagation estimation operations.
Figure 17B:
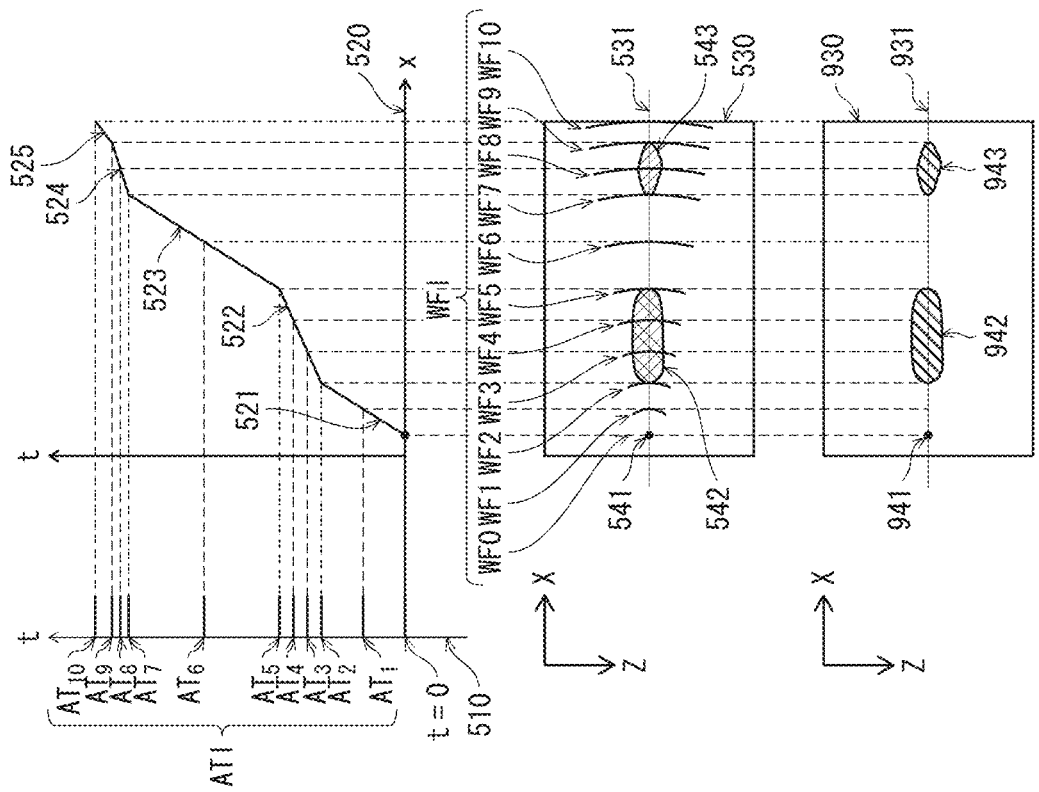
Figure 18:
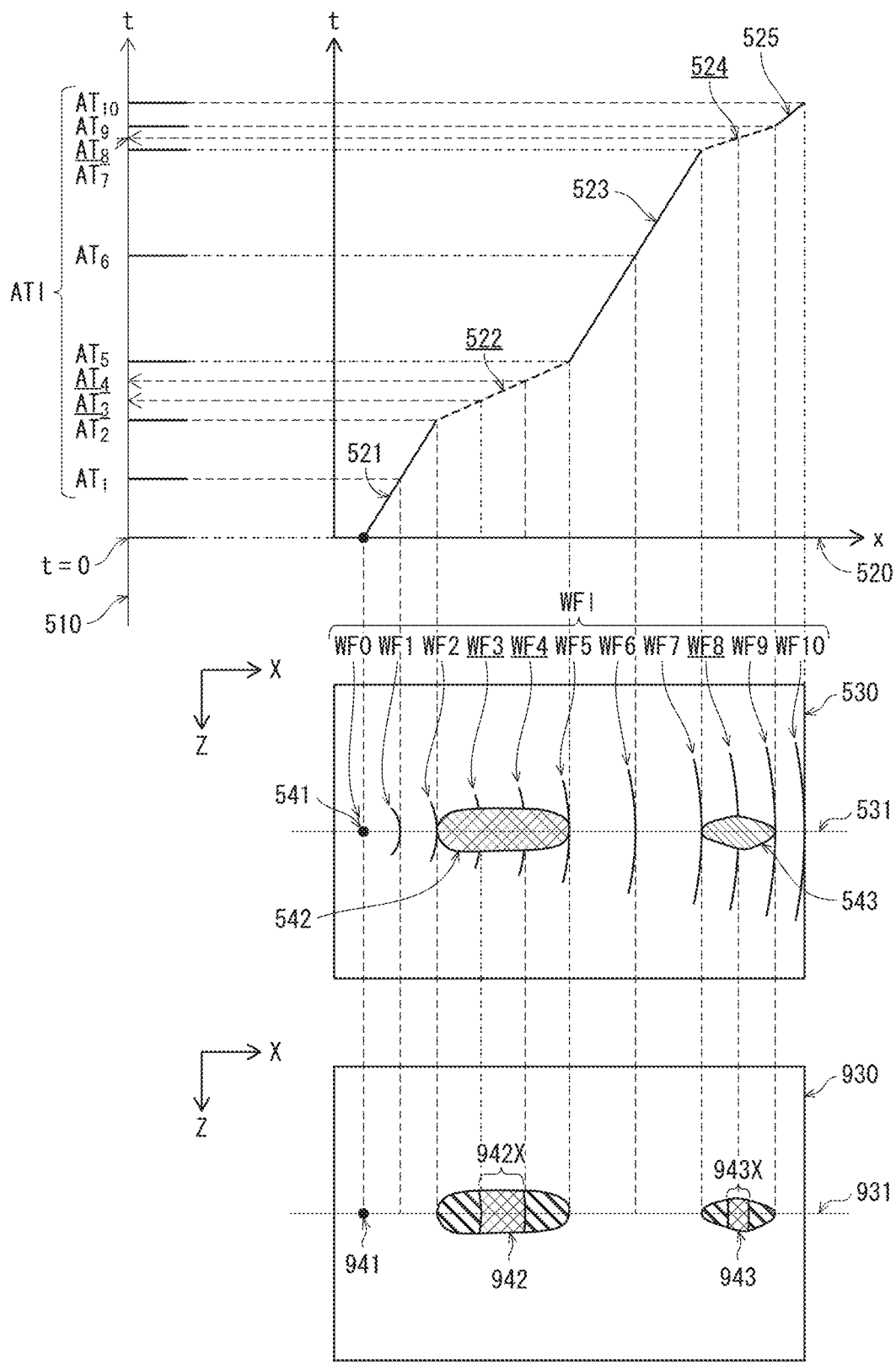
FIG. 18 is schematic diagram showing a shear wave propagation estimation operation.

FIG. 17A and FIG. 17B are schematic diagrams showing shear wave propagation estimation operations. In FIG. 17A, FIG. 17B, and FIG. 18, each elasticity image 930 is an elasticity image of a region of interest ROI. Each image 530 is an image showing each wavefront WF1 in wavefront frame data WF1 in the elasticity image 930 of the region of interest ROI. Here, inclusions 542, 543 are image portions representing harder portions than surrounding tissue in a subject. A focus point F of a push wave PP in each elasticity image acquired is a focus point 541. Each graph 520 is a graph showing how x direction position and wavefront WF1 relate to wavefront arrival time AT1 on a straight line 531 along a certain depth that includes the focus point 541 of the push wave PP. Shear wave propagation speed V is represented as slope of the graph 520.

As shown in graph 520, shear wave propagation speed V is fast in a section 522 corresponding to the inclusion 542 and a section 524 corresponding to the inclusion 543, and slow in other sections 521, 523, 525. The inclusions 542, 543 are harder than surrounding tissue, and therefore an absolute value of displacement due to a shear wave is less than in surrounding tissue. Thus, in regions of the image 530 corresponding to the inclusions 542, 543, it may occur that a wavefront WF1 cannot be detected.

FIG. 17A shows a case in which a wavefront WF3 and a wavefront WF4 in a region of the image 530 corresponding to the inclusion 542 and a wavefront WF8 in a region of the image 530 corresponding to the inclusion 543 are detected normally. In the graph 520, wavefront arrival time AT3 and wavefront arrival time AT4, corresponding to the wavefront WF3 and the wavefront WF4 in the section 522 corresponding to the inclusion 542, and wavefront arrival time AT8 corresponding to the wavefront WF8 in the section 524 corresponding to the inclusion 543, are calculated normally. As a result, an image portion 942 corresponding to the inclusion 542 and an image portion 943 corresponding to the inclusion 543 are generated normally in the elasticity image 930.

FIG. 17B shows a case in which the wavefront WF3 and the wavefront WF4 in a region of the image 530 corresponding to the inclusion 542 and the wavefront WF8 in a region of the image 530 corresponding to the inclusion 543 are not detected normally. In the graph 520, wavefront arrival time AT3 and wavefront arrival time AT4, corresponding to the wavefront WF3 and the wavefront WF4 in the section 522 corresponding to the inclusion 542, and wavefront arrival time AT8 corresponding to the wavefront WF8 in the section 524 corresponding to the inclusion 543, are not calculated and become blank data. As a result, an image portion 942 corresponding to the inclusion 542 and an image portion 943 corresponding to the inclusion 543, which should be displayed as a high elastic modulus in the elasticity image 930, become blank.

FIG. 18 shows a case in which the ultrasound diagnostic device 100 pertaining to the present invention is used. In a case in which the wavefront WF3 and the wavefront WF4 in a region of the image 530 corresponding to the inclusion 542 and the wavefront WF8 in a region of the image 530 corresponding to the inclusion 543 are not detected normally, the wavefront arrival time AT3 and the wavefront arrival time AT4 in the section 522 corresponding to the inclusion 542 and the wavefront arrival time AT8 in the section 524 corresponding to the inclusion 543 are calculated by interpolation based on a relationship between x direction position in other sections 521, 523, 525 and wavefront arrival time AT. In the graph 520, wavefront arrival time AT3 and wavefront arrival time AT4, corresponding to the wavefront WF3 and the wavefront WF4 in the section 522 corresponding to the inclusion 542, and wavefront arrival time AT8 corresponding to the wavefront WF8 in the section 524 corresponding to the inclusion 543, are each calculated based on a corresponding interpolation calculation.

As a result, an image portion 942 corresponding to the inclusion 542 and an image portion 943 corresponding to the inclusion 543 are also generated in the elasticity image 930, based on estimated values of wavefront WF. In the elasticity image 930, an image portion 942X corresponding to the wavefront WF3 and the wavefront WF4 in the image portion 942 corresponding to the inclusion 542, and an image portion 943X corresponding to the wavefront WF8 in the image portion 943 corresponding to the inclusion 543, may be displayed in a different manner so that it can be seen that they are generated based on estimated values.

In step S1550, wavefront arrival time data ATij is stored in the data storage 115 as compensated wavefront arrival time CATij, then whether or not processing is complete for all j in the region of interest ROI is determined (step S1551), and whether or not processing is complete for all i in the region of interest ROI is determined (step S1553). When incomplete, i or j is incremented (steps S1552, S1554), in order to generate compensated wavefront arrival time data CATij for another observation point Pij (step S1549), and when complete, processing ends.

5. Details of Processing in Step S155.

In step S155, the elastic modulus calculator 112 calculates shear wave propagation speed data or elastic modulus data based on compensated wavefront arrival time frame data CATo for an observation point Pij in the region of interest ROI, and calculates elastic modulus frame data ELF for the region of interest ROI.

Figure 19:
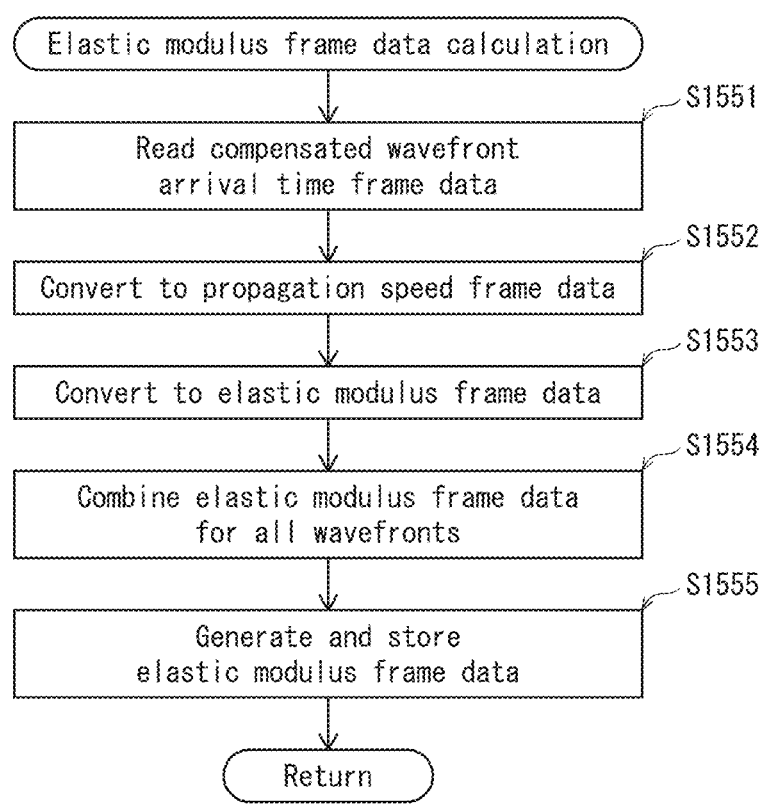
FIG. 19 is a flowchart showing an operation of elastic modulus calculation of ultrasound diagnostic device 100.

FIG. 19 is a flowchart showing an operation of ultrasound elastic modulus calculation of the ultrasound diagnostic device 100. Initially, the elastic modulus calculator 112 reads compensated wavefront arrival time frame data CATo from the data storage 115 (step S1551) and converts to propagation speed frame data VFo according to a method indicated below (step S1552).

Figure 14F:
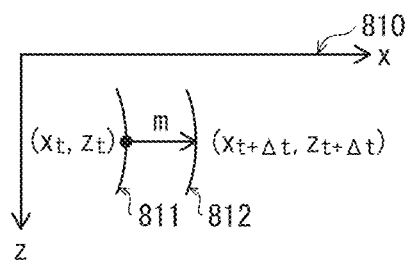

In FIG. 14F, speed $V(x_t, z_t)$ at which a shear wave passes coordinates $(x_t, z_t)$ can be estimated as a value of a distance m between coordinates $(x_t, z_t)$ and coordinates $(x_t+\Delta_t, z_t+\Delta_t)$ divided by a required time $\Delta t$. That is:

$$V(x_t,z_t)=m/\Delta t=\sqrt{\{(x_{t+\Delta t}-x_t)^2+(z_{t+\Delta t}-z_t)^2\}}/\Delta t$$

The elastic modulus calculator 112 extracts compensated wavefront arrival time data CAT from compensated wavefront arrival time frame data CATo and performs the above processing for all wavefronts, and acquires shear wave speed V for all coordinates a given wavefront passes.

Column F of FIG. 12 shows propagation speed frame data VF obtained by differentiating wavefront arrival time frame data AT calculated for each transmission event.

Next, the elastic modulus calculator 112 converts propagation speed frame data VFo to elastic modulus frame data (step S1553). Elastic modulus frame data is elastic modulus calculated at each coordinate based on shear wave propagation speed. Elastic modulus is proportional to the square of the speed of the shear wave.

$$EL(x_t,z_t)=K\times V(x_t,z_t)^2$$

K is a constant and is approximately three in human tissue.

The column G of FIG. 12 shows elastic modulus frame data ELF calculated by the above equation from propagation speed frame data VF.

According to the above processing, the elastic modulus calculator combines elastic modulus frame data elo for all wavefronts o (where o is a natural number representing wavefront number, and elastic modulus frame data EL is used where wavefront number is not distinguished) (step S1554). The elastic modulus calculator 112 averages elastic modulus frame data elo with respect to all wavefronts o, indexed with coordinates ij, to generate one frame of elastic modulus frame data ELF, and stores same in the data storage 115 (step S1555).

Thus, calculation processing of elastic modulus measurement based on shear wave propagation analysis is completed.

6. Details of Processing in Step S150

Figure 20:
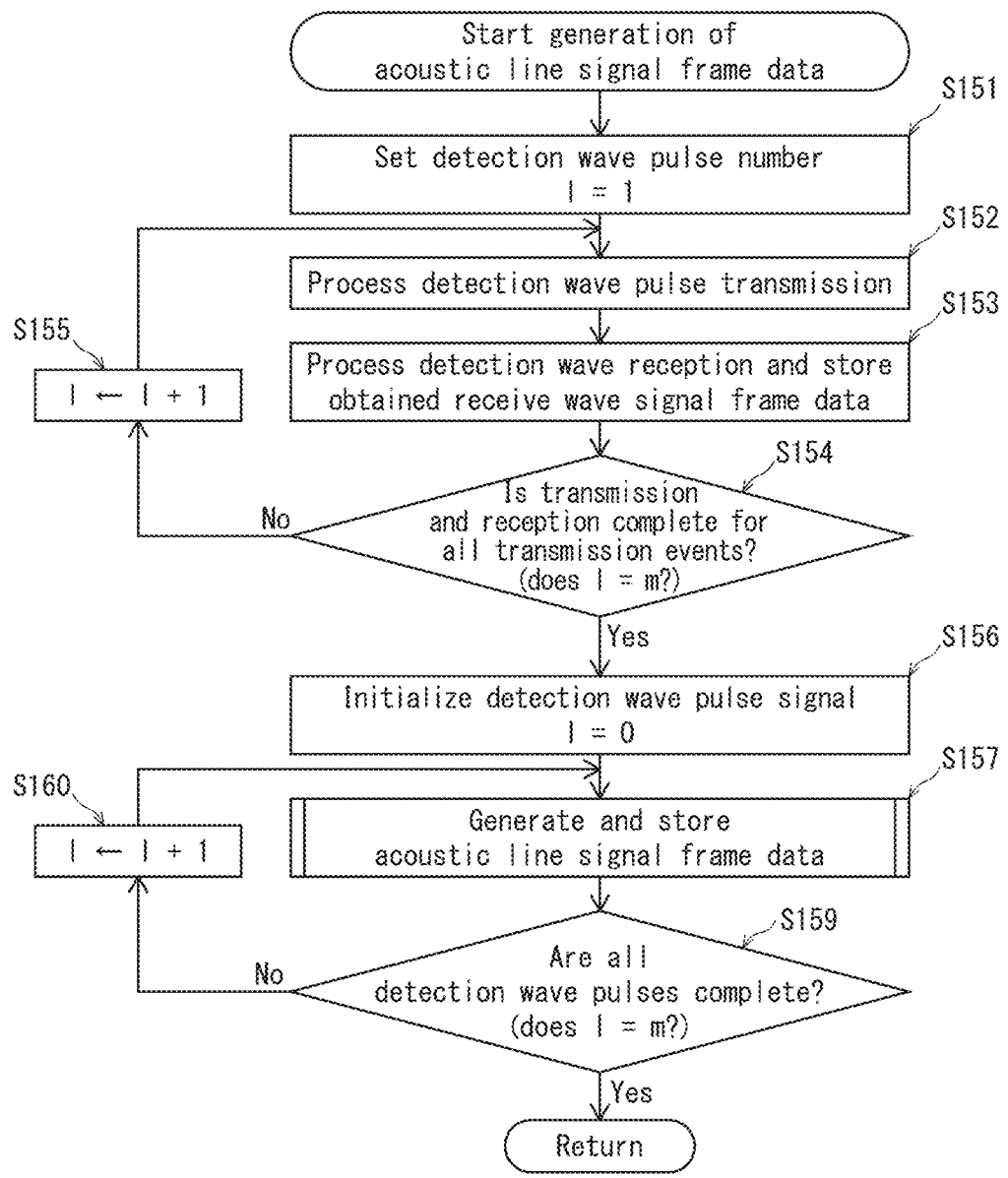
FIG. 20 is a flowchart showing an operation of receive beamforming.

An outline of the process of generating acoustic line signal frame data DS1 in step S150 is described below. FIG. 20 is a flowchart showing beamforming operation of the detection wave receiver 108.

Initially, detection wave identification number 1 is set to 1 (step S151), and the transmitter performs a transmission process (transmission event) of transmitting a detection wave pulse PWP1 for causing transducers included in the detection wave transmission transducer array Tx among the transducers 101a of the probe 101 to transmit a detection wave PW1 (step S152).

Next, the detection wave receiver 108 generates a receive signal RFk based on an electric signal obtained from a reflected wave at the probe 101, outputs same to the data storage 115, and stores the receive signal RFk in the data storage 115 (step S153). It is then determined whether or not transmission and reception of a detection wave is complete for the number m of all defined transmission events (step S154). If not complete, 1 is incremented (step S155), processing returns to step S152, and a transmission event is performed from the detection wave transmission transducer array Tx. If complete, processing proceeds to step S156.

Next, the detection wave identification number 1 is initialized to 0 (step S156), and the detection wave receiver 108 generates an acoustic line signal for each observation point Pij in the detection wave irradiation region Ax, based on a receive signal RFk stored in the data storage 115, in order to generate acoustic line signal frame data DS1, output same to the data storage 115, and store the acoustic line signal frame data DS1 in the data storage 115 (step S157). A method of generating acoustic line signal frame data DS1 in step S157 is described in detail later.

It is then determined whether or not generation of acoustic line signal frame data DS1 based on a detection wave pulse PWP1 is complete for the number m of all transmission events (step S159), when not complete 1 is incremented (step S160) and processing returns to step S157, and when complete processing ends.

Thus, processing of step S150 in FIG. 19 is completed.
7. Details of Processing in Step S157

Details of the process of generating acoustic line signal frame data DS1 in step S157 are described below.

Figure 21:
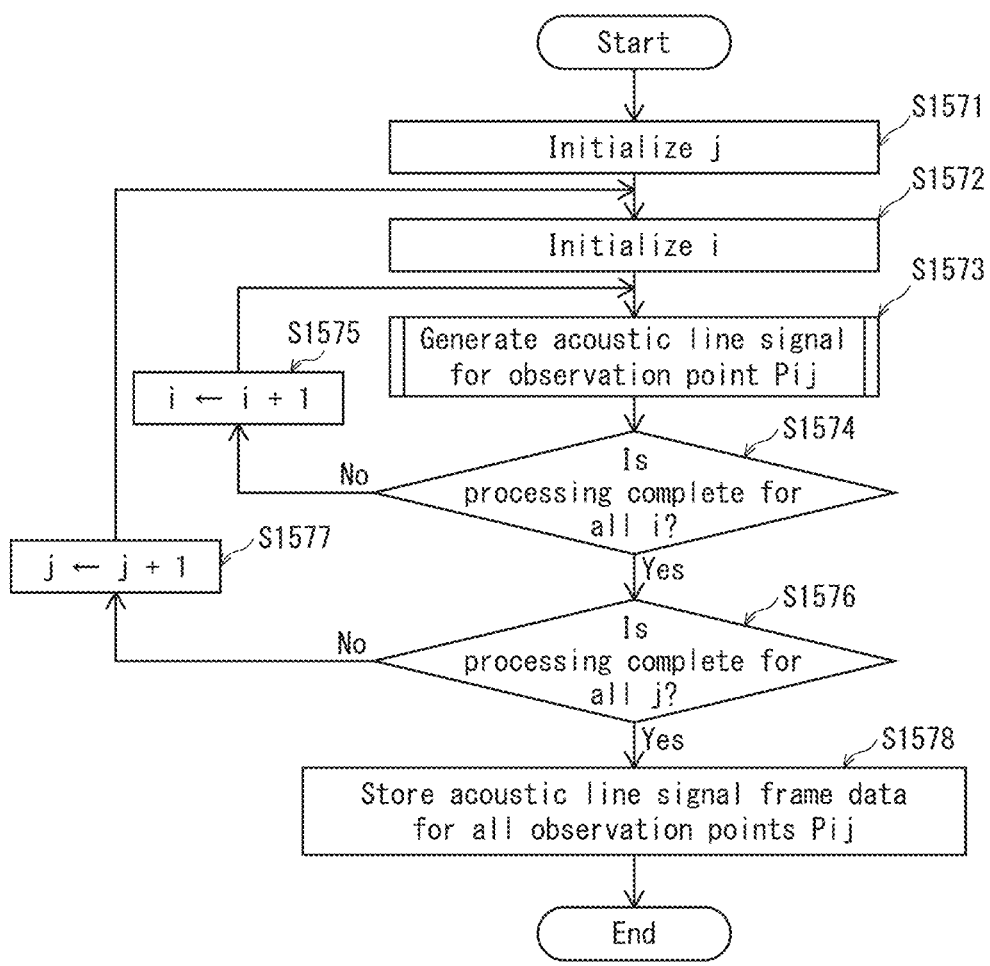
FIG. 21 is a flowchart showing an acoustic line signal frame data generation operation.

FIG. 21 is a flowchart showing the acoustic line signal frame data generation operation of the detection wave receiver 108.

Initially, j and i are initialized to minimum values in the detection wave irradiation region Ax (steps S1571, S1572). Next, the detection wave receiver 108 generates an acoustic line signal DSij for an observation point Pij (step S1573). Details of processing in step S1573 are provided later.

Next, it is determined whether or not processing is complete for all of i in the detection wave irradiation region Ax (step S1574) and whether or not processing is complete for all of j in the detection wave irradiation region Ax (step S1576), when not complete, i or j is incremented (steps S1575, S1577), and an acoustic line signal is generated for an observation point Pij (step S1573), and when complete, processing proceeds to step S1578.

At this stage, acoustic line signal DSij is generated for all observation points Pij in the detection wave irradiation region Ax for one transmission event, and acoustic line signal frame data DS1 is generated. In step S1578, generated acoustic line signal frame data DS1 is outputted to and stored in the data storage 115.

Thus, processing of step S157 in FIG. 20 is completed.
8. Details of Processing in Step S1573

Figure 22:
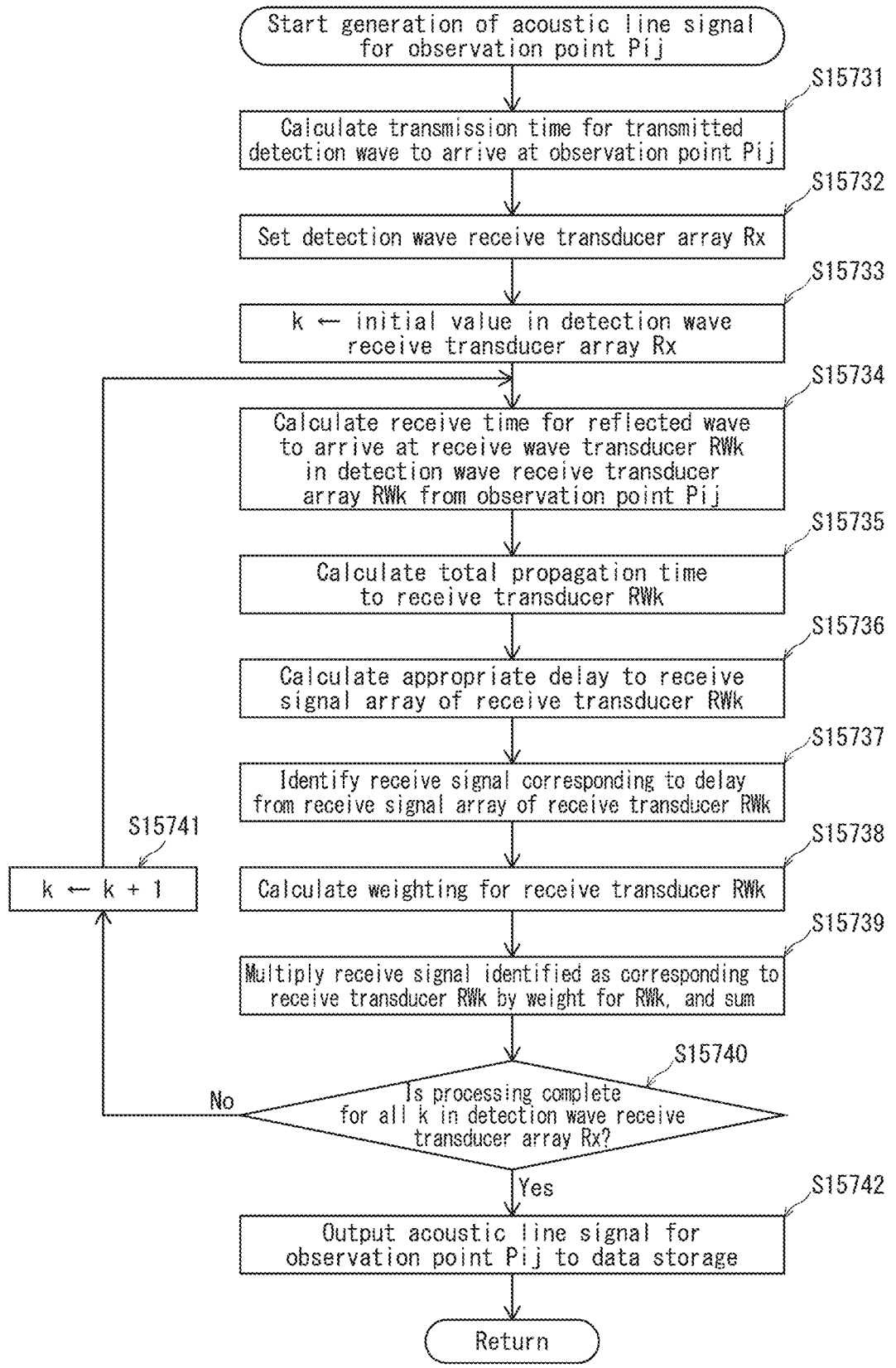
FIG. 22 is a flowchart showing an acoustic line signal data generation operation with respect to an observation point Pij.

Next, operation of processing in generating an acoustic line signal for an observation point Pij in step S1573 is described. FIG. 22 is a flowchart showing acoustic line signal generation operation for an observation point Pij by the detection wave receiver 108.

Initially, in step S15731, the delay processing section 10831 calculates a transmission time for transmitted ultrasound to reach the observation point Pij in the subject, for an observation point Pij present in the detection wave irradiation region Ax. As stated above, transmission time is calculated so a transmission path to the observation point Pij is set as a shortest path 401 from the detection wave transmission transducer array Tx for a detection wave PW1 emitted perpendicular to the transducer array to arrive at the observation point Pij, and length of the transmission path is divided by the speed of sound CS of the ultrasound.

Next, the detection wave receive transducer array Rx is set (step S15732).

Next, a transducer identification number k of a receive transducer RWk in the detection wave receive transducer array Rx is initialized to a minimum value in the detection wave receive transducer array Rx (step S15733), and after a transmitted detection wave is reflected at the observation point Pij in the subject, a receive time to arrive at the receive transducer RWk of the detection wave receive transducer array Rx is calculated (step S15734). Receive time can be calculated by dividing a geometrically determined length of the path 402 from the observation point Pij to the receive transducer RWk by the speed of sound CS of ultrasound. Further, from a total of transmission time and receive time, a total propagation time is calculated for ultrasound transmitted from the detection wave transmission transducer array Tx and reflected at the observation point Pij to arrive at the receive transducer RWk (step S15735), and a delay for the receive transducer RWk is calculated from differences in total propagation among receive transducers RWk in the detection wave receive transducer array Rx (step S15736).

In step S15737, the delay processing section 10831, from receive signals corresponding to receive transducers RWk in the detection wave receive transducer array Rx, identifies a receive signal RFk corresponding to a time obtained by subtracting delay for the receive transducer RWk as a receive signal based on a reflected wave from the observation point Pij.

Next, a weighting section (not illustrated) calculates receive apodization for each receive transducer RWk so weight for a transducer positioned at a center in the row direction of the detection wave receive transducer array Rx is maximized (step S15738). The summing section 10832 multiplies the receive signal RFk identified as corresponding to a receive transducer RWk by a weight of the receive transducer RWk, and sums the results to calculate an acoustic line signal DSij for the observation point Pij (step S150159).

It is then determined whether or not calculation of acoustic line signal DSij is complete for all receive transducers RWk in the detection wave receive transducer array Rx (step S15740), when not complete, k is incremented (step S15741) and delay is calculated for another receive transducer RWk (step S15739), and when complete, processing proceeds to step S15742. At this stage, acoustic line signal DSij for an observation point Pij for all receive transducers RWk in the detection wave receive transducer array Rx has been calculated. The acoustic line signal DSij for the observation point Pij is outputted to and stored by the data storage 115 (step S15762).

Thus, processing of step S1573 in FIG. 21 is completed.

<Effects>

Conventionally, in cases such as a region in which it is difficult to obtain a reflected wave in tissue of a subject, and signal intensity of a detected acoustic line signal is minute, accuracy of detection is low, and detection of tissue displacement by a shear wave from the acoustic line signal at at least a predefined accuracy is difficult; further, in cases in which there is a hard part in tissue of a subject, and an absolute value of displacement detected is minute, accuracy of detection is low, and calculation of a wavefront of a shear wave from the displacement at at least a predefined accuracy is difficult. Thus, in a generated elasticity image, in image regions corresponding to hard portions of tissue that are supposed to be displayed as a high elastic modulus, image omissions may occur due to elastic modulus not being calculated.

However, according to the ultrasound diagnostic device 100 pertaining to Embodiment 1, a configuration is used that includes a propagation information estimator that evaluates reliability of wavefront arrival time in wavefront arrival time frame data, extracts a reliability nonconformance region of the wavefront arrival time frame data, interpolates reliability nonconformance wavefront arrival time data in wavefront arrival time frame data based on wavefront arrival time data that satisfies a predefined condition to generate compensated wavefront arrival time data, and generates compensated wavefront arrival time frame data by replacing reliability nonconformance wavefront arrival time data with compensated wavefront arrival time data; and an elastic modulus calculator that calculates propagation speed of a shear wave in a region of interest or elastic modulus, based on the compensated wavefront arrival time frame data.

According to the above configuration, it is possible to suppress image omission in an elasticity image in a region in which reliability of measured wavefront arrival time data is low.

Embodiment 2

According to the ultrasound diagnostic device 100 pertaining to Embodiment 1, the elastic modulus calculator 112 is configured to calculate shear wave propagation speed based on compensated wavefront arrival time frame data CATo for observation points Pij in a region of interest ROI.

However, a configuration may be used that calculates propagation speed frame data based on displacement frame data PT1 with respect to observation points Pij other than reliability nonconformance observation points LLij that do not satisfy a predefined condition due to data reliability being equal to or less than a threshold.

An ultrasound diagnostic device 100A pertaining to Embodiment 2 is different from Embodiment 1 in that a configuration is used in which a reliability nonconformance observation point LLij that does not satisfy a predefined condition due to data reliability being equal to or less than a threshold is calculated, and for observation points Pij other than the reliability nonconformance observation point LLij, propagation speed frame data based on displacement frame data PT1 is calculated to convert propagation speed frame data to elastic modulus frame data, while for reliability nonconformance observation points LLij, as for Embodiment 1, the elastic modulus calculator 112 calculates shear wave propagation speed frame data based on compensated wavefront arrival time frame data CATo, in order to convert propagation speed frame data to elastic modulus frame data.

The following describes the ultrasound diagnostic device 100A.

<Configuration>

In the ultrasound diagnostic device 100A, configuration of the propagation information analyzer and the elastic modulus calculator are different from those of Embodiment 1, and therefore these configurations of the ultrasound diagnostic device 100A are described below. Other configuration is the same as for the ultrasound diagnostic device 100 and description thereof is omitted.

Figure 23:
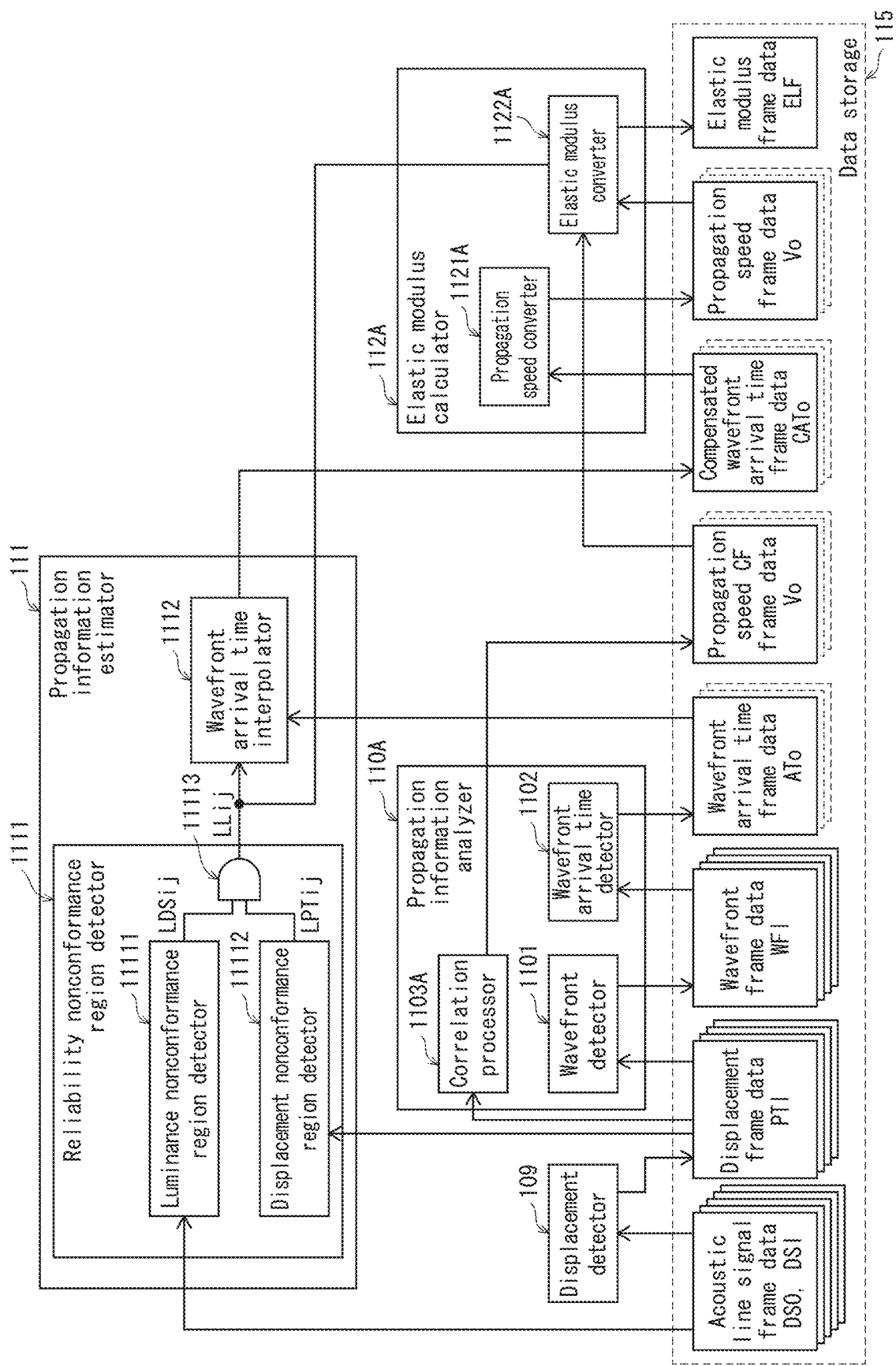
FIG. 23 is a function block diagram showing configuration of displacement detector 109, propagation information analyzer 110A, propagation information estimator 111, and an elastic modulus calculator 112A in ultrasound diagnostic device 100A pertaining to Embodiment 2.

FIG. 23 is a function block diagram of the ultrasound diagnostic device 100A showing configuration of the displacement detector 109, a propagation information analyzer 110A, the propagation information estimator 111, and an elastic modulus calculator 112A. Of these, configuration of the propagation information analyzer 110A and the elastic modulus calculator 112A is described below.

The propagation information analyzer 110A is composed of the wavefront detector 1101, the wavefront arrival time detector 1102, and a correlation processor 1103A, which differs from the ultrasound diagnostic device 100 in that it includes the correlation processor 1103A.

The correlation processor 1103A directly generates, by using cross-correlation processing, propagation speed CF frame data Vo from a sequence of displacement frame data PT1 for each translation event, and outputs to the data storage 115.

Figure 24B:
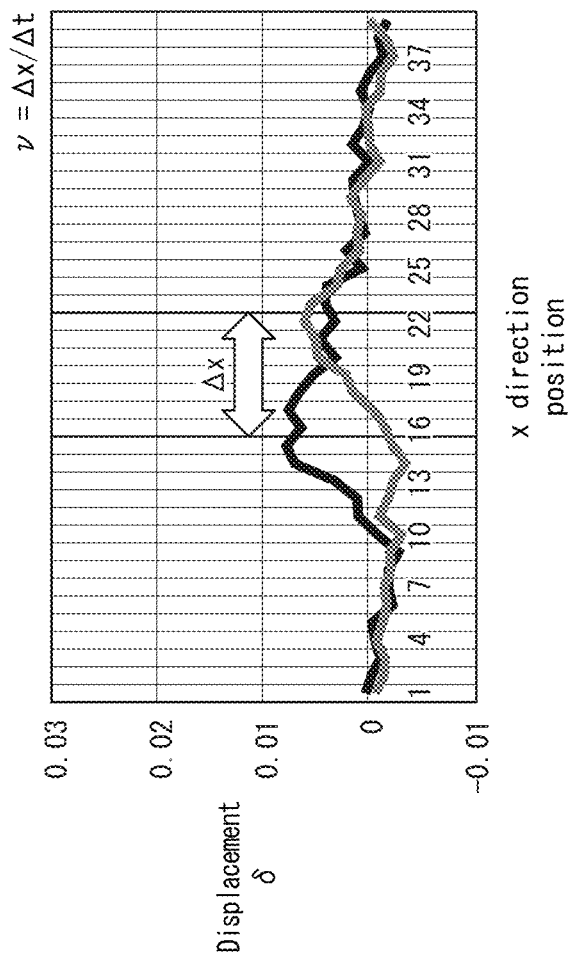
FIG. 24A and FIG. 24B are schematic diagrams showing shear wave propagation analysis operations of ultrasound diagnostic device 100A.
Figure 24A:
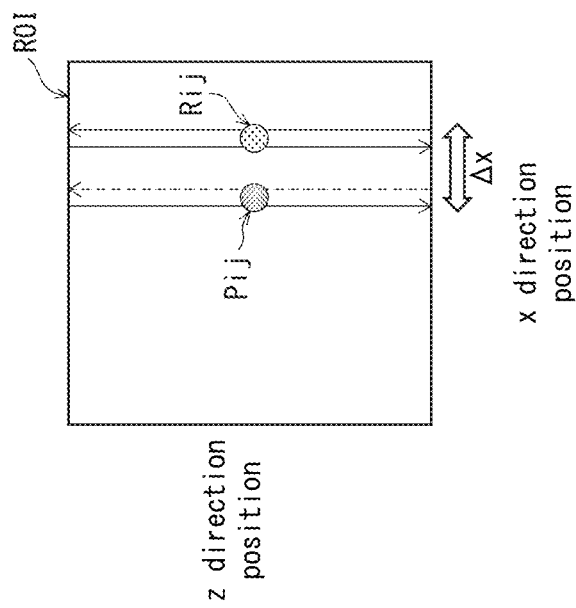

FIG. 24A and FIG. 24B are schematic diagrams showing shear wave propagation analysis operations of the ultrasound diagnostic device 100A. As shown in FIG. 24A, a target observation point Pij and a reference observation point Rij having equal z direction positions and separated by a predefined distance $\Delta x$ are defined in a region of interest ROI. As shown in FIG. 24B, the correlation processor 1103A extracts time series variation data of displacement PTij for the target observation point Pij and the reference observation point Rij, based on a sequence of displacement frame data PT1, performs cross-correlation processing between time series variation data, and calculates travel time $\Delta t$ of displacement PTij between the target observation point Pij and the reference observation point Rij. Thus, by dividing the predefined distance $\Delta x$ by the travel time $\Delta t$, propagation speed Vij of a shear wave is calculated with respect to the target observation point Pij. According to this processing, propagation speed Cf frame data Vo is directly generated by calculating propagation speed Vij of a shear wave for each target observation point Pij in a region of interest ROI.

The elastic modulus calculator 112A is composed of the propagation speed converter 1121 and an elastic modulus converter 1122A, and differs from the ultrasound diagnostic device 100 in that it includes the elastic modulus converter 1122A.

The elastic modulus converter 1122A inputs propagation speed data Vo and propagation speed CF data Vo, and when an observation point Pij in a region of interest ROI is a reliability nonconformance observation point LLij, converts propagation speed data Vij to elastic modulus data ELij for the observation point Pij, and when an observation point Pij in the region of interest ROI is not a reliability nonconformance observation point LLij, converts propagation speed data CFVij to elastic modulus data ELij for the observation point Pij. Thus, elastic modulus frame data ELF is generated for the region of interest ROI.

The elastic modulus calculator 112A outputs generated elastic modulus frame data ELF to the data storage 115 via the controller 116.

<Operations>

The following describes operations of a SWS sequence of the ultrasound diagnostic device 100A.

Operations of a SWS sequence of the ultrasound diagnostic device 100A compared to operation flow of the SWS sequence of the ultrasound diagnostic device 100 differ in part from the flowchart shown in FIG. 13 in details of propagation information analysis of a shear wave according to step S153. Further, elastic modulus calculation shown in step S155 of FIG. 10 is different. These differing operation are described below.

1. Shear Wave Propagation Information Analysis

Figure 25:
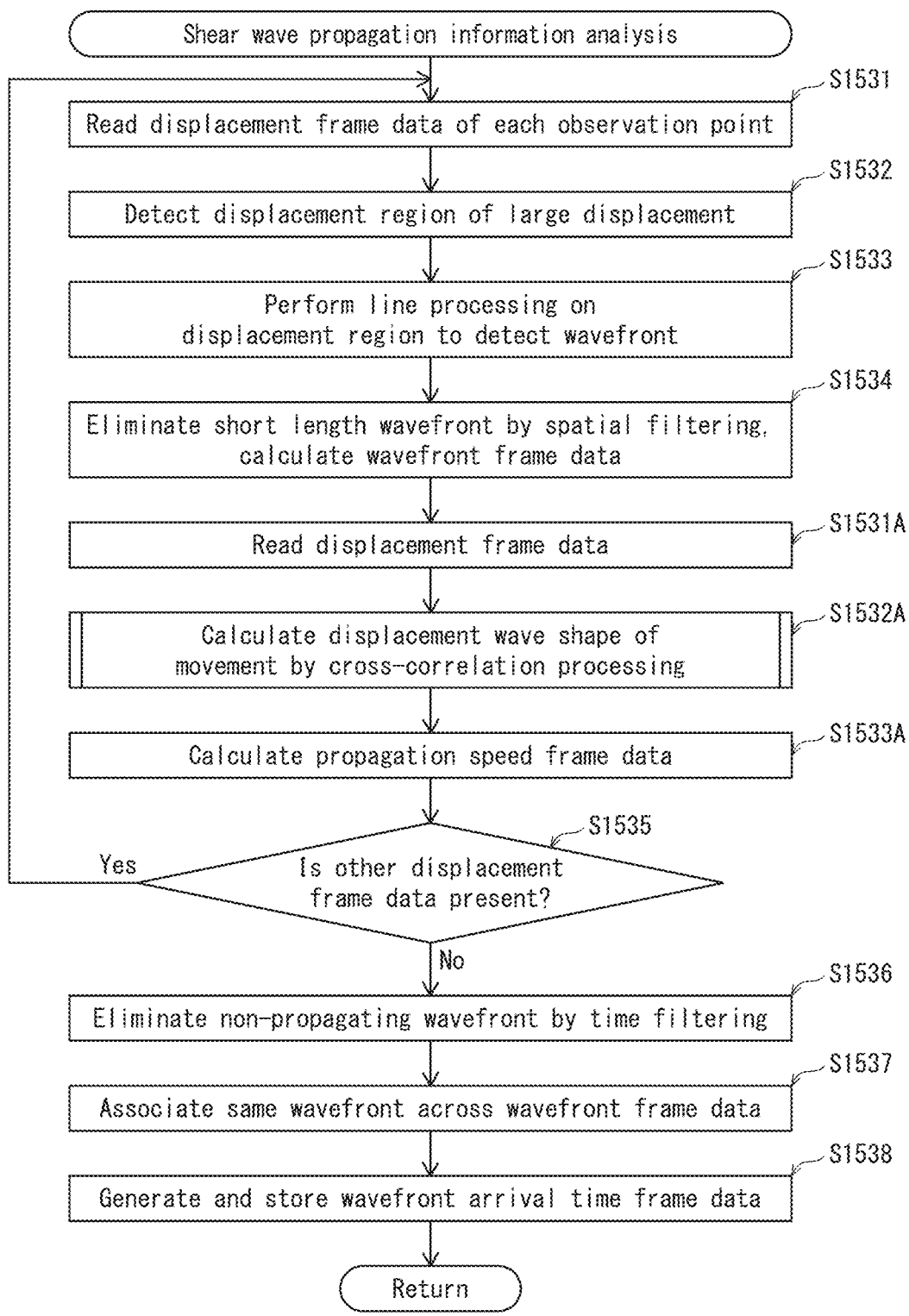
FIG. 25 is a flowchart showing an operation of shear wave propagation information analysis of ultrasound diagnostic device 100A.

FIG. 25 is a flowchart showing an operation of shear wave propagation information analysis of the ultrasound diagnostic device 100A. Operations from step S1531 to S1534 are the same as those of the ultrasound diagnostic device 100 shown in FIG. 13, and therefore not described here.

According to the ultrasound diagnostic device 100A, after step S1534, the correlation processor 1103A reads a sequence of displacement frame data PT1 from the data storage 115 (step S1531A), performs cross-correlation processing between time series variation data of displacement PTij of a target observation point Pij and a reference observation point Rij that is a predefined distance $\Delta x$ from the target observation point Pij, calculates a travel time $\Delta t$ of displacement PTij between the target observation point Pij and the reference observation point Rij (step S1532A), and calculates shear wave propagation speed Vij for the target observation point Pij by dividing $\Delta x$ by $\Delta t$. According to this processing, propagation speed CF frame data Vo is directly generated for each target observation point Pij in a region of interest ROI (step S1533A). Operations from step S1535 to S1538 are the same as those of the ultrasound diagnostic device 100 shown in FIG. 13, and therefore not described here.

2. Operations of Elastic Modulus Calculation

Figure 26:
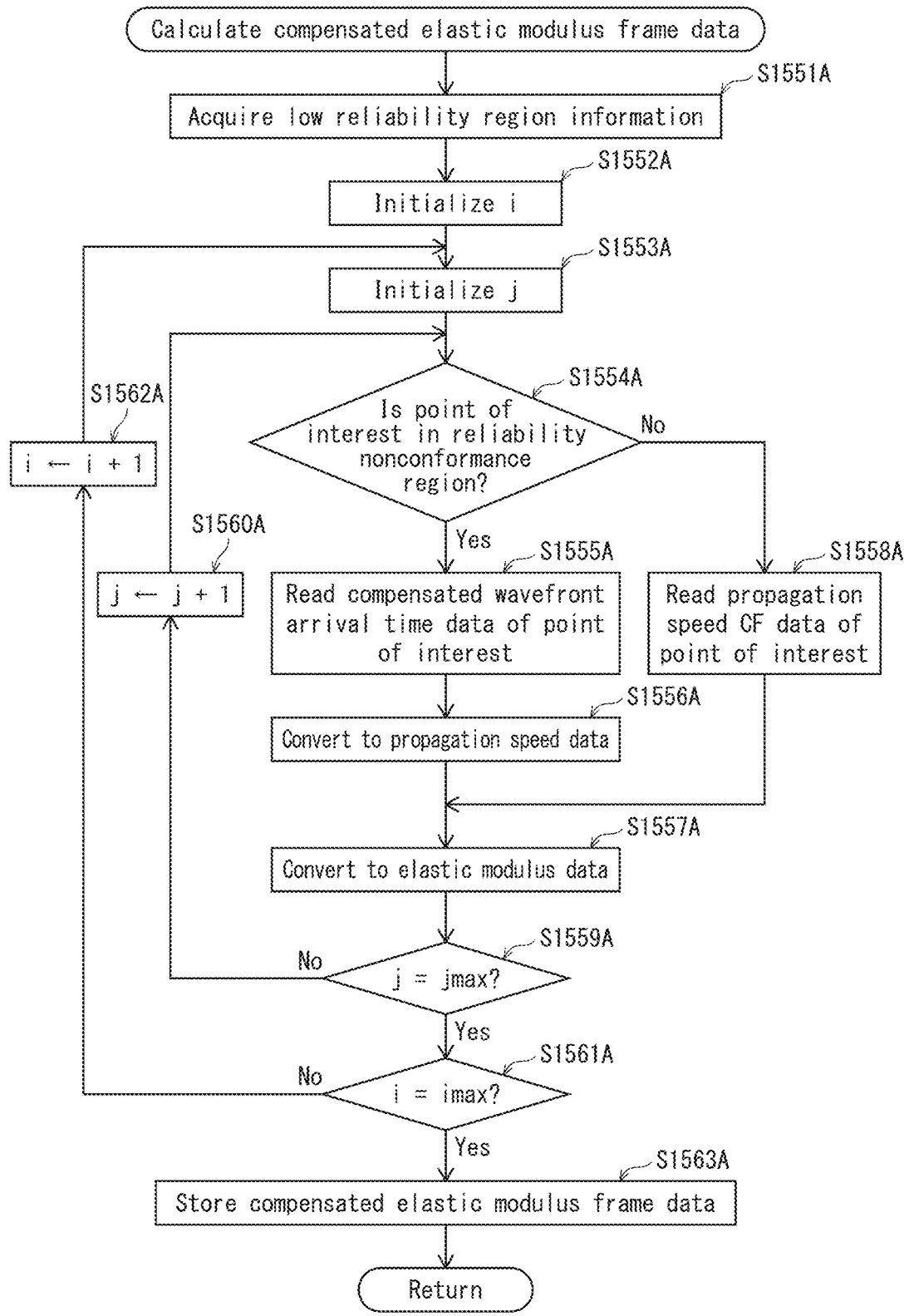
FIG. 26 is a flowchart showing an operation of elastic modulus calculation of ultrasound diagnostic device 100A.

The elastic modulus calculator 112 calculates shear wave propagation speed data or elastic modulus data based on compensated wavefront arrival time frame data CATo for an observation point Pij in the region of interest ROI, and calculates elastic modulus frame data ELF for the region of interest ROI. FIG. 26 is a flowchart showing an operation of ultrasound elastic modulus calculation of the ultrasound diagnostic device 100A. These are the details of the processing in step S155 of FIG. 10.

First, the elastic modulus converter 1122A obtains reliability nonconformance region information relating to coordinates ij of reliability nonconformance observation point LLij in the region of interest ROI from the reliability nonconformance region detector 1111 (step S1551A).

Then, i and j are initialized to minimum values in the region of interest ROI (step S1552A, S1553A). The elastic modulus converter 1122A determines whether or not the target observation point Pij is included in a reliability nonconformance region (step S1554A), and when the target observation point Pij is included in a reliability nonconformance region (Yes), reads compensated wavefront arrival time data CATij for the target observation point Pij from the data storage 115 (step S1555A), and converts it to propagation speed data Vij by the same method as used in step S1552 (step S156A). When the target observation point Pij is not included in a reliability nonconformance region (No), the elastic modulus converter 1122A reads propagation speed CF data Vij of the target observation point Pij from the data storage 115 (step S1558A). Next, the elastic modulus calculator 112A converts the propagation speed data Vij or the propagation speed CF data Vij to elastic modulus data ELij (step S1557A), determines whether or not processing is complete for all of j in the region of interest ROI (step S1559A), determines whether or not processing is complete for all of i in the region of interest ROI (step S1561A), and when not complete, increments i or j (steps S1560A, S1562A) and generates elastic modulus data ELij for a new observation point Pij (step S1557A), and when complete, stores elastic modulus frame data ELF in the data storage 115 (step S1561A) and ends processing.

Thus, elastic modulus measurement calculation is completed.

3. Description of Shear Wave Propagation Speed Vij Calculation by using Cross-Correlation Processing.

Figure 27:
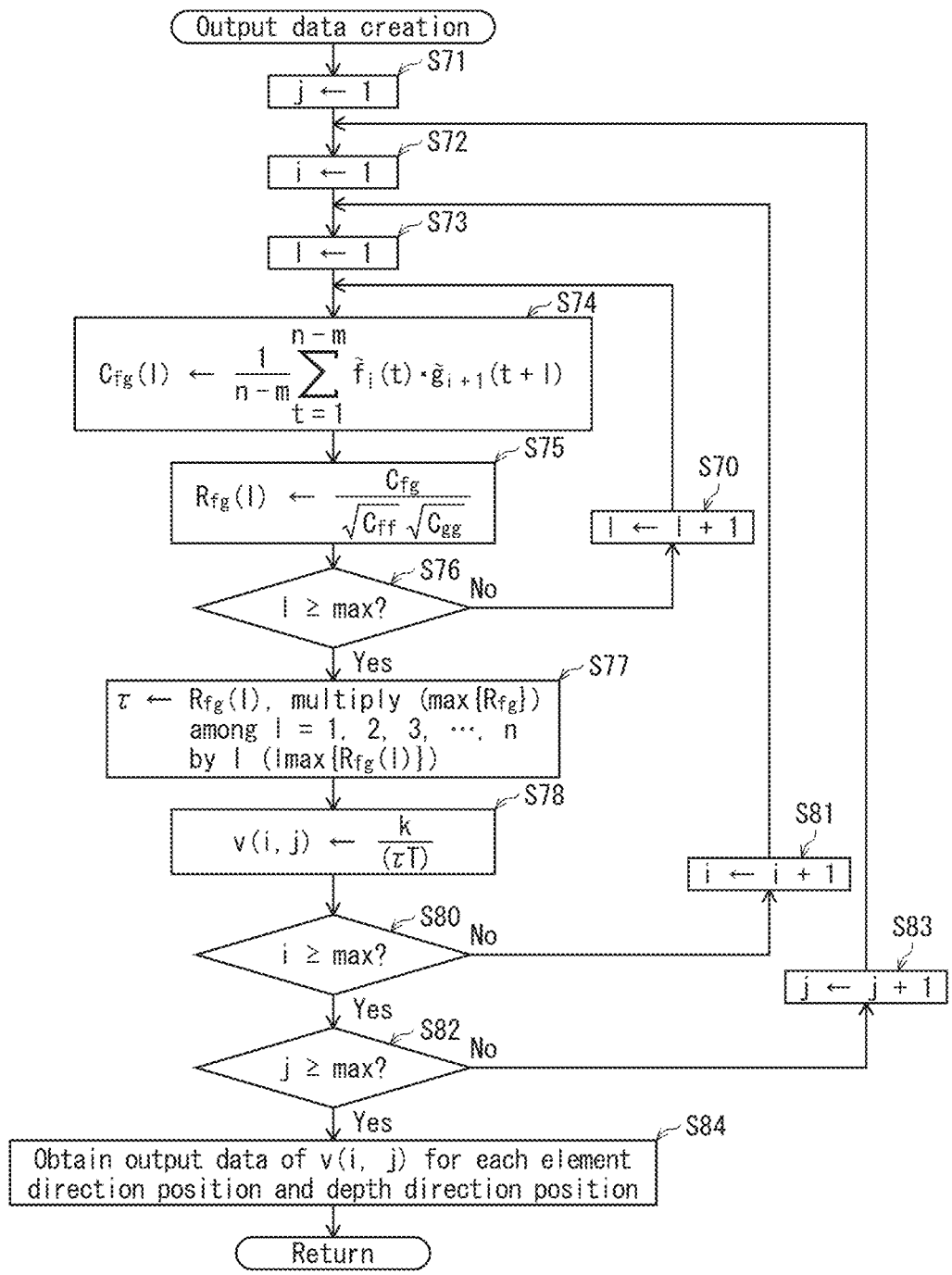
FIG. 27 is a flowchart showing operations of step S1532A and step S1533A.

FIG. 27 is a flowchart showing a procedure of generating output data of shear wave propagation speed Vij that can be used in steps similar to steps S1532A, S1533A in FIG. 25.

This flowchart includes a loop for variable 1, a loop for variable i, and a loop for variable j. The loop for variable 1 that means a difference in wavefront arrival time at a position i in the x direction (transducer array direction) and wavefront arrival time at a position i+1 in the x direction, is for calculating $R_{fg}$, $C_{fg}$ for the various values of variable 1. Here, $f_i(t)$ indicates change in wavefront position in a time axis direction at x direction position (i) and $g_{i+1}(t)$ indicates change in wavefront position in the time axis direction at x direction position (i+1). The loop for variable i is for calculating shear wave propagation speed for each x direction position in one z direction (subject depth direction) position. The loop for variable j is for repeating v(i, j) for each z direction position.

In step S71, variable j that indicates a z direction position is initialized to 1, and in step S72, variable i that indicates a transducer array direction is initialized to 1. In step S73, variable 1 is initialized to 1. In step S74, a product-sum operation is performed for variable 1, which is set to one value by initialization or variable updating, in order to calculate a correlation value $C_{fg}$ between $f_i(t)$ and $g_{i+1}(t+1)$. In step S75, correlation value $C_{fg}$ is normalized to obtain a normalized correlation value $R_{fg}$. Step S76 is a completion condition of the loop for variable 1, and if 1 has not reached a maximum value max, variable 1 is incremented (step S70) and processing returns to step S74. Until variable 1 reaches a maximum value max, the process of incrementing variable 1, calculating $C_{fg}$, and normalizing is repeated. When 1 reaches maximum value max ("Yes" at step S76), processing proceeds to step S77. In step S77, a deviation τ in the time direction is calculated by multiplying a minimum value for Rfg among values of 1=1, 2, 3, 4, 5, . . . , n by variable 1. In step S78, a local value of shear wave speed is calculated by the calculation v←k/(τT), to obtain shear wave propagation speed v(i, j) at coordinates (i, j).

In step S80 it is determined whether or not variable i has reached a maximum value max, and if not reached, variable i is incremented (step S81) and processing returns to step S73. Step S82 is a completion condition of the loop for variable j, and if the maximum value max is not reached ("No" at step S82), variable j is incremented in step S83 and processing returns to step S72. When variable j reaches the maximum value max, processing exits the loop. Step S84 is a final process after all loops are completed, and obtains output data of shear wave propagation speed v(i, j) with respect to each x direction position and z direction position.

As described above, according to this calculation method, apparent temporal resolution and spatial resolution can be increased. Thus, it is possible to calculate shear wave speed at the moment when the shear wave passes through hard tissue, so elasticity evaluation can be performed with high accuracy.

Thus, SWS sequence processing is completed. According to the ultrasound elastic modulus measurement processing of the ultrasound diagnostic device 100A, SWS sequence elastic modulus frame data ELF can be calculated.

<Effects>

As described above, the ultrasound diagnostic device 100A pertaining to Embodiment 2 uses a configuration in which a reliability nonconformance observation point LLij that does not satisfy a predefined condition due to data reliability being equal to or less than a threshold is calculated, and for observation points Pij other than the reliability nonconformance observation point LLij, propagation speed frame data based on displacement frame data PT1 is calculated to convert propagation speed frame data to elastic modulus frame data, while for reliability nonconformance observation points LLij, as for Embodiment 1, the elastic modulus calculator 112 calculates shear wave propagation speed frame data based on compensated wavefront arrival time frame data CATo, in order to convert propagation speed frame data to elastic modulus frame data.

According to this configuration, in ultrasound elastic modulus measurement, with respect to a reliability nonconformance observation point LLij, image omission is suppressed in an elasticity image in a region in which reliability of measured wavefront arrival time data is low, and with respect to an observation point Pij other than a reliability nonconformance observation point LLij, propagation speed frame data and elastic modulus frame data can be calculated with high accuracy by increasing temporal resolution and spatial resolution.

<Other Modifications>

The present invention is described based on the embodiments above, but the present invention is not limited to these embodiments, and the following modification are also included in the scope of the present invention.

For example, the ultrasound diagnostic device 100A pertaining to Embodiment 2 uses a configuration in which a reliability nonconformance observation point LLij for which data reliability is equal to or less than a threshold is calculated, and for observation points Pij other than the reliability nonconformance observation point LLij, propagation speed frame data based on displacement frame data PT1 is calculated to convert propagation speed frame data to elastic modulus frame data, while for reliability nonconformance observation points LLij, as for Embodiment 1, the elastic modulus calculator 112 calculates shear wave propagation speed frame data based on compensated wavefront arrival time frame data CATo, in order to convert propagation speed frame data to elastic modulus frame data. However, as long as a configuration is used in which a reliability nonconformance observation point LLij for which data reliability is equal to or below a threshold is detected, different signal processing is applied in parallel for the reliability nonconformance observation point LLij and an observation point Pij other than the reliability nonconformance observation point LLij, and an elasticity image is simultaneously generated from the different signal processing, the processing method is of course not limited to calculation of propagation speed frame data. For example, the different signal processing for a reliability nonconformance observation point LLij and an observation point Pij other than the reliability nonconformance observation point LLij may be applied to displacement detection, wavefront detection, conversion to elastic modulus, image shape recognition, motion determination, and the like.

Further, in the ultrasound diagnostic device 100 pertaining to an embodiment, configurations of the transmitter 106, the detection wave receiver 108, the displacement detector 109, the propagation information analyzer 110, the propagation information estimator 111, and the elastic modulus calculator 112 may be modified as appropriate.

For example, according to an embodiment, a push wave is transmitted from all of the transducers 101a of the probe 101, but the transmitter 106 may be configured to set a push wave transmission transducer array Px composed of a portion of the transducers 101a of the probe 101, and for each SWS sequence, a transmission transducer array may gradually move in the array direction as ultrasound transmission is repeated. Acoustic radiation force can be increased by push waves.

Further, according to an embodiment, a region of interest ROI is set in a partial region of a detection wave irradiation region Ax of a transducer array (101a) of the transducers 101a, but the region of interest ROI may be set to the maximum range of the detection wave irradiation region Ax.

Further, according to an embodiment, the region of interest ROI is set in a partial region of the detection wave irradiation region Ax; the push wave pulse generator 104 sets a plurality of the transistors 101a as a push wave transmission transducer array Px, and sets a single focus point F in the region of interest ROI for a push wave; an SWS sequence is performed by repeatedly transmitting and receiving detection waves PW1 in the region of interest ROI; and elastic modulus frame data EL is calculated for observation points in the region of interest ROI for one SWS sequence. However, a configuration may be used in which the region of interest ROI is set as a partial region of the detection wave irradiation region Ax, and while the transmission focus point F is gradually moved in the array direction to transmit a push wave PP for each SWS sequence, a target observation region in the region of interest ROI is made different according to position of the transmission focus point F while transmission and reception of a detection wave PW1 is repeated, and combined elastic modulus frame data EMP is calculated for a partial region of the region of interest ROI for each SWS sequence is combined to calculate an integrated SWS sequence combined elastic modulus EL for the entire region of interest ROI.

Further, according to an embodiment, a region in which an observation point exists is an area having a same width as a receive transducer array and is perpendicular to the receive transducer array.

However, the present invention is not limited to this, and the region may be set to an arbitrary region included in an ultrasound irradiation region. For example, a rectangular region having a width of a plurality of transducers and a center line of a straight line perpendicular to a receive transducer array that passes through a center of the receive transducer array may be used.

Further, the present invention may be a computer system including a microprocessor and a memory, for example, the memory storing a computer program and the microprocessor operating according to the computer program. For example, the present invention may be a computer system that operates (or instructs operation of connected elements) according to a computer program of a diagnostic method of an ultrasound diagnostic device of the present invention.

Further, cases in which all or part of the ultrasound diagnostic device, or all or part of a beamforming section are constituted by a computer system including a microprocessor, and a storage medium such as ROM, RAM, etc., are included in the present invention. A computer program for achieving the same operations as the devices described above may be stored in RAM or a hard disk unit. The microprocessor operates according to the computer program, thereby achieving the functions of each device.

Further, all or part of the elements of each device may be configured as one system large scale integration (LSI). A system LSI is an ultra multifunctional LSI manufactured by integrating a plurality of elements on one chip, and more specifically is a computer system including a microprocessor, ROM, RAM, or the like. The plurality of elements can be integrated on one chip, or a portion may be integrated on one chip. Here, LSI may refer to an integrated circuit, a system LSI, a super LSI, or an ultra LSI, depending on the level of integration. A computer program for achieving the same operation as the devices described above may be stored in the RAM. The microprocessor operates according to the computer program, the system LSI thereby achieving the functions. For example, a case of the beamforming method of the present invention stored as a program of an LSI, the LSI inserted into a computer, and a predefined program (beamforming method) being executed is also included in the present invention.

Note that methods of circuit integration are not limited to LSI, and implementation may be achieved by a dedicated circuit or general-purpose processor. After LSI manufacture, a field programmable gate array (FPGA) or a reconfigurable processor, in which circuit cell connections and settings in the LSI can be reconfigured, may be used.

Further, if a circuit integration technology is introduced that replaces LSI due to advances in semiconductor technology or another derivative technology, such technology may of course be used to integrate the function blocks.

Further, all or part of the functions of an ultrasound diagnostic device pertaining to an embodiment may be implemented by execution of a program by a processor such as a CPU. All or part of the functions of an ultrasound diagnostic device pertaining to an embodiment may be implemented by a non-transitory computer-readable storage medium on which a program is stored that causes execution of a diagnostic method or beamforming method of an ultrasound diagnostic device described above. A program and signals may be recorded and transferred on a storage medium so that the program may be executed by another independent computer system, or the program may of course be distributed via a transmission medium such as the Internet.

According to an ultrasound diagnostic device pertaining to an embodiment, the ultrasound diagnostic device includes a data storage as a storage device. However, a storage device is not limited to this and a semiconductor memory, hard disk drive, optical disk drive, magnetic storage device, or the like may be externally connectable to the ultrasound diagnostic device.

Further, the division of function blocks in the block diagrams is merely an example, and a plurality of function blocks may be implemented as one function block, one function block may be divided into a plurality, and a portion of a function may be transferred to another function block. Further, a single hardware or software element may process the functions of a plurality of function blocks having similar functions in parallel or by time division.

Further, the order in which steps described above are executed is for illustrative purposes, and the steps may be in an order other than described above. Further, a portion of the steps described above may be executed simultaneously (in parallel) with another step.

Further, the ultrasound diagnostic device is described as having an externally connected probe and display, but may be configured with an integral probe and/or display.

Further, according to an embodiment above, the probe is configured to have a plurality of piezoelectric transducers arranged in a one-dimensional direction. However, probe configuration is not limited to this example, and as further examples, a two-dimensional transducer array in which piezoelectric transducers are arranged in a two-dimensional direction or a dynamic probe in which transducers arranged in a one-dimensional direction are mechanically swung to acquire a three-dimensional tomographic image may be used, and such probes may be used situationally depending on a measurement. For example, when a two-dimensionally arranged probe is used it is possible to control irradiation position and direction of an ultrasound beam to be transmitted by changes to voltage application timing and value to individual piezoelectric transducers.

Further, a portion of functions of the transmitter and the detection wave receiver may be included in the probe. For example, a transmission electrical signal may be generated and converted to ultrasound in the probe, based on a control signal for generating a transmission electrical signal outputted from the transmitter. It is possible to use a configuration that converts a received reflected wave into a receive wave signal and generates an acoustic line signal based on the receive wave signal in the probe.

Further, at least a portion of functions of each ultrasound diagnostic device pertaining to an embodiment, and each modification thereof, may be combined. Further, the numbers used above are all illustrative, for the purpose of explaining the present invention in detail, and the present invention is not limited to the example numbers used above. Further, the present invention includes various modifications that are within the scope of conceivable ideas by a person skilled in the art.

<<Summary>>

As described above, An ultrasound diagnostic device pertaining to an embodiment is an ultrasound diagnostic device that causes a probe to transmit a push wave focused on a specific site in a subject and detects propagation speed of a shear wave generated by acoustic radiation force of the push wave, the probe being connectable to the ultrasound diagnostic device and including transducers arranged in a row, the ultrasound diagnostic device comprising: ultrasound signal processing circuitry, the ultrasound signal processing circuitry comprising: a push wave pulse transmitter that supplies a push wave pulse to a plurality of the transducers that causes the plurality of the transducers to transmit the push wave; a detection wave pulse transmitter that, a plurality of times after the push wave pulse, supplies a detection wave pulse to a plurality of the transducers that causes the plurality of the transducers to transmit a detection wave that passes through a region of interest that represents a range to be analyzed in the subject; a detection wave receiver that generates acoustic line signals with respect to observation points in the region of interest, based on reflected detection waves that correspond to the detection waves and are reflected from subject tissue and received in a time sequence by a plurality of the transducers, and generates a sequence of acoustic line signal frame data; a displacement detector that, from the sequence of acoustic line signal frame data, detects displacement of tissue in the region of interest for each receive time of the reflected detection waves, and generates a sequence of displacement frame data; a propagation information analyzer that extracts shear wave wavefront position from the sequence of the displacement frame data, generates a sequence of wavefront frame data, and generates wavefront arrival time frame data by associating wavefront position included in each frame of the wavefront frame data with the receive time; a propagation information estimator that evaluates reliability of wavefront arrival time data in the wavefront arrival time frame data and, for reliability nonconformance wavefront arrival time data in the wavefront arrival time frame data that does not satisfy a predefined condition, generates compensated wavefront arrival time data by interpolation based on wavefront arrival time data that does satisfy the predefined condition, replaces the reliability nonconformance wavefront arrival time data with the compensated wavefront arrival time data, and generates compensated wavefront arrival time frame data; and an elastic modulus calculator that calculates shear wave propagation speed and/or elastic modulus frame data in the region of interest, based on the compensated wavefront arrival time frame data.

According to the above configuration, it is possible to suppress image omission in an elasticity image in a region in which reliability of measured wavefront arrival time data is low in ultrasound elastic modulus measurement.

Further, according to another example configuration, the propagation information estimator determines that, in the wavefront arrival time frame data, wavefront arrival time data in a reliability nonconformance region in which signal strength of an acoustic line signal in the acoustic line signal frame data is equal to or less than a threshold value is the reliability nonconformance wavefront arrival time data.

According to this configuration, it is possible to suppress image omission in an elasticity image in a low reliability region of measured wavefront arrival time data in a case such as a region in which it is difficult to obtain a reflected wave in tissue of a subject, and signal intensity of a detected acoustic line signal is minute, accuracy of detection is low, and detection of tissue displacement by a shear wave from the acoustic line signal at at least a predefined accuracy is difficult.

Further, according to another example configuration, the propagation information estimator determines that, in the wavefront arrival time frame data, wavefront arrival time data in a reliability nonconformance region in which an absolute value of displacement data in the displacement frame data is equal to or less than a threshold value is the reliability nonconformance wavefront arrival time data.

According to this configuration, it is possible to suppress image omission in an elasticity image in a low reliability region of measured wavefront arrival time data in a case in which there is a hard part in tissue of a subject, and an absolute value of displacement detected is minute, accuracy of detection is low, and calculation of a wave front of a shear wave from the displacement at at least a predefined accuracy is difficult.

Further, according to another example configuration, the propagation information estimator compensates the reliability nonconformance wavefront arrival time data by using spline interpolation or polygonal line approximation interpolation.

According to this configuration, wavefront arrival time data AT (reliability nonconformance wavefront arrival time data AT) for a reliability nonconformance observation point LLij is interpolated based on wavefront arrival time data AT that satisfies a predefined condition, in order to calculate compensated wavefront arrival time data CATij, by simple calculation.

Further, according to another example configuration, the propagation information analyzer includes a correlation processor that calculates, based on the sequence of the displacement frame data, time series variation data of displacement at a target observation point and a reference observation point a predefined distance from the observation point, calculates a travel time of displacement between the target observation point and the reference observation point, based on cross-correlation processing performed on the time series variation data, calculates shear wave propagation speed at the target observation point by dividing the predefined distance by the travel time, and directly generates propagation speed frame data by calculating shear wave propagation speed at each of the observation points in the region of interest by setting each of the observation points as the target observation point, and the elastic modulus calculator, for a reliability nonconformance region in the region of interest in which reliability nonconformance wavefront arrival time data in the wavefront arrival time frame data is obtained, calculates elastic modulus data based on propagation speed data that depends on the compensated wavefront arrival time frame data, and for a region other than the reliability nonconformance region in the region of interest, calculates elastic modulus data based on the directly generated propagation speed data.

According to this configuration, in ultrasound elastic modulus measurement, with respect to a reliability nonconformance observation point LLij, image omission is suppressed in an elasticity image in a region in which reliability of measured wavefront arrival time data is low, and with respect to an observation point Pij other than a reliability nonconformance observation point LLij, propagation speed frame data and elastic modulus frame data can be calculated with high accuracy by increasing temporal resolution and spatial resolution.

Further, another example configuration further comprises: a display that displays an image, wherein the elastic modulus calculator generates an elasticity image by mapping the elastic modulus frame data, converts the elasticity image to a display image, and causes the display to display the display image.

According to this configuration, for example, an elasticity image may be generated in different colors in which coordinates for which the elastic modulus is equal to or greater than a certain value are red, coordinates for which the elastic modulus is less than the certain value are green, and coordinates for which elastic modulus could not be acquired are black, thereby improving convenience for a user.

Further, according to another example configuration, the elastic modulus calculator generates the elasticity image so as to display elastic modulus data that depends on the compensated wavefront arrival time data in a manner different from elastic modulus data that does not depend on the compensated wavefront arrival time data.

According to the above configuration, a user can recognize that a portion of an elasticity image that depends on compensated wavefront arrival time data is a region of lower reliability that measured wavefront arrival time data, improving convenience for the user.

Further, according to another example configuration, the detection wave is a plane wave that propagates in the subject in a direction perpendicular to the row of the transducers.

According to this configuration, operation is simple in cases such as when a subject is not specified and convenience for a user is improved in cases such as when a subject is first measured.

Further, according to another example configuration, a center in a row direction of the plurality of the transducers that transmit the detection wave coincides with a center in the row direction of the region of interest.

According to this configuration, elastic modulus frame data EL can be calculated for an observation point in a region of interest ROI by one SWS sequence.

Further, a control method of an ultrasound diagnostic device pertaining to an embodiment is a control method of an ultrasound diagnostic device that causes a probe to transmit a push wave focused on a specific site in a subject and detects propagation speed of a shear wave generated by acoustic radiation force of the push wave, the probe being connectable to the ultrasound diagnostic device and including transducers arranged in a row, the control method comprising: supplying a push wave pulse to a plurality of the transducers that causes the plurality of the transducers to transmit the push wave; a plurality of times after the push wave pulse, supplying a detection wave pulse to a plurality of the transducers that causes the plurality of the transducers to transmit a detection wave that passes through a region of interest that represents a range to be analyzed in the subject; generating acoustic line signals with respect to observation points in the region of interest, based on reflected detection waves that correspond to the detection waves and are reflected from subject tissue and received in a time sequence by a plurality of the transducers, and generating a sequence of acoustic line signal frame data; from the sequence of acoustic line signal frame data, detecting displacement of tissue in the region of interest for each receive time of the reflected detection wave, and generating a sequence of displacement frame data; extracting shear wave wavefront position from the sequence of the displacement frame data, generating a sequence of wavefront frame data, and generating wavefront arrival time frame data by associating wavefront position included in each frame of the wavefront frame data with the receive time; evaluating reliability of wavefront arrival time data in the wavefront arrival time frame data and, for reliability nonconformance wavefront arrival time data in the wavefront arrival time frame data that does not satisfy a predefined condition, generating compensated wavefront arrival time data by interpolation based on wavefront arrival time data that does satisfy the predefined condition, replacing the reliability nonconformance wavefront arrival time data with the compensated wavefront arrival time data, and generating compensated wavefront arrival time frame data; and calculating shear wave propagation speed and/or elastic modulus frame data in the region of interest, based on the compensated wavefront arrival time frame data.

According to the above configuration, it is possible to suppress image omission in an elasticity image in a region in which reliability of measured wavefront arrival time data is low, and measure elasticity using an ultrasound diagnostic device.

As described above, according to the ultrasound diagnostic device and the ultrasound signal processing method pertaining to aspects of the present disclosure, it is possible to suppress image omission in an elasticity image in a region in which reliability of measured wavefront arrival time data is low in ultrasound elastic modulus measurement.

Although the present invention has been fully described by way of examples with reference to the accompanying drawings, it is to be noted that various changes and modifications will be apparent to those skilled in the art. Therefore, unless such changes and modifications depart from the scope of the present invention, they should be construed as being included therein.

What is claimed is:

1. An ultrasound diagnostic device that causes a probe to transmit a push wave focused on a specific site in a subject and detects propagation speed of a shear wave generated by acoustic radiation force of the push wave, the probe being connectable to the ultrasound diagnostic device and including transducers arranged in a row, the ultrasound diagnostic device comprising:

ultrasound signal processing circuitry, the ultrasound signal processing circuitry comprising:

a push wave pulse transmitter that supplies a push wave pulse to a first plurality of the transducers that causes the first plurality of the transducers to transmit the push wave;

a detection wave pulse transmitter that, a plurality of times after the push wave pulse, supplies a detection wave pulse to a second plurality of the transducers that causes the second plurality of the transducers to transmit a detection wave that passes through a region of interest that represents a range to be analyzed in the subject;

a detection wave receiver that generates acoustic line signals with respect to observation points in the region of interest, based on reflected detection waves that correspond to the detection waves and are reflected from subject tissue and received in a time sequence by a third plurality of the transducers, and generates a sequence of acoustic line signal frame data;

a displacement detector that, from the sequence of acoustic line signal frame data, detects displacement of tissue in the region of interest for each receive time of the reflected detection waves, and generates a sequence of displacement frame data;

a propagation information analyzer that extracts shear wave wavefront position from the sequence of the displacement frame data, generates a sequence of wavefront frame data, and generates wavefront arrival time frame data by associating wavefront position included in each frame of the sequence of wavefront frame data with the receive time, wherein the shear wave wavefront position is extracted by extracting a displacement region from the displacement frame data in which a displacement amount exceeds a threshold, performing a thinning process on the displacement region to extract at least one wavefront, and applying spatial filtering and time filtering to the at least one wavefront;

a propagation information estimator that evaluates reliability of wavefront arrival time data in the wavefront arrival time frame data and, for reliability nonconformance wavefront arrival time data in the wavefront arrival time frame data that does not satisfy a predefined condition, generates compensated wavefront arrival time data by interpolation based on wavefront arrival time data that does satisfy the predefined condition, replaces the reliability nonconformance wavefront arrival time data with the compensated wavefront arrival time data, and generates compensated wavefront arrival time frame data; and an elastic modulus calculator that calculates shear wave propagation speed and/or elastic modulus frame data in the region of interest, based on the compensated wavefront arrival time frame data.

2. The ultrasound diagnostic device of claim 1, wherein the propagation information estimator determines that, in the wavefront arrival time frame data, wavefront arrival time data in a reliability nonconformance region in which an absolute value of displacement data in the displacement frame data is equal to or less than a threshold value is the reliability nonconformance wavefront arrival time data.

3. The ultrasound diagnostic device of claim 1, wherein the propagation information estimator compensates the reliability nonconformance wavefront arrival time data by using spline interpolation or polygonal line approximation interpolation.

4. The ultrasound diagnostic device of claim 1, wherein the propagation information analyzer includes a correlation processor that calculates, based on the sequence of the displacement frame data, time series variation data of displacement at a target observation point and a reference observation point a predefined distance from the observation point, calculates a travel time of displacement between the target observation point and the reference observation point, based on cross-correlation processing performed on the time series variation data, calculates shear wave propagation speed at the target observation point by dividing the predefined distance by the travel time, and directly generates propagation speed frame data by calculating shear wave propagation speed at each of the observation points in the region of interest by setting each of the observation points as the target observation point, and the elastic modulus calculator, for a reliability nonconformance region in the region of interest in which reliability nonconformance wavefront arrival time data in the wavefront arrival time frame data is obtained, calculates elastic modulus data based on propagation speed data that depends on the compensated wavefront arrival time frame data, and for a region other than the reliability nonconformance region in the region of interest, calculates elastic modulus data based on the directly generated propagation speed data.

5. The ultrasound diagnostic device of claim 1, further comprising:

a display that displays an image, wherein the elastic modulus calculator generates an elasticity image by mapping the elastic modulus frame data, converts the elasticity image to a display image, and causes the display to display the display image.

6. The ultrasound diagnostic device of claim 5, wherein the elastic modulus calculator generates the elasticity image so as to display elastic modulus data that depends on the compensated wavefront arrival time data in a manner different from elastic modulus data that does not depend on the compensated wavefront arrival time data.

7. The ultrasound diagnostic device of claim 1, wherein the detection wave is a plane wave that propagates in the subject in a direction perpendicular to the row of the transducers.

8. The ultrasound diagnostic device of claim 1, wherein a center in a row direction of the second plurality of the transducers that transmit the detection wave coincides with a center in the row direction of the region of interest.

9. A control method of an ultrasound diagnostic device that causes a probe to transmit a push wave focused on a specific site in a subject and detects propagation speed of a shear wave generated by acoustic radiation force of the push wave, the probe being connectable to the ultrasound diagnostic device and including transducers arranged in a row, the control method comprising:

supplying a push wave pulse to a first plurality of the transducers that causes the first plurality of the transducers to transmit the push wave;

a plurality of times after the push wave pulse, supplying a detection wave pulse to a second plurality of the transducers that causes the second plurality of the transducers to transmit a detection wave that passes through a region of interest that represents a range to be analyzed in the subject;

generating acoustic line signals with respect to observation points in the region of interest, based on reflected detection waves that correspond to the detection waves and are reflected from subject tissue and received in a time sequence by a third plurality of the transducers, and generating a sequence of acoustic line signal frame data;

from the sequence of acoustic line signal frame data, detecting displacement of tissue in the region of interest for each receive time of the reflected detection wave, and generating a sequence of displacement frame data;

extracting shear wave wavefront position from the sequence of the displacement frame data, generating a sequence of wavefront frame data, and generating wavefront arrival time frame data by associating wavefront position included in each frame of the wavefront frame data with the receive time, wherein the shear wave wavefront position is extracted by extracting a displacement region from the displacement frame data in which a displacement amount exceeds a threshold, performing a thinning process on the displacement region to extract at least one wavefront, and applying spatial filtering and time filtering to the at least one wavefront;

evaluating reliability of wavefront arrival time data in the wavefront arrival time frame data and, for reliability nonconformance wavefront arrival time data in the wavefront arrival time frame data that does not satisfy a predefined condition, generating compensated wavefront arrival time data by interpolation based on wavefront arrival time data that does satisfy the predefined condition, replacing the reliability nonconformance wavefront arrival time data with the compensated wavefront arrival time data, and generating compensated wavefront arrival time frame data; and calculating shear wave propagation speed and/or elastic modulus frame data in the region of interest, based on the compensated wavefront arrival time frame data.

10. The ultrasound diagnostic device of claim 1, wherein in the wavefront arrival time frame data, wavefront arrival time data in a reliability nonconformance region in which an absolute value of displacement data in the displacement frame data is equal to or less than a threshold value is determined to be the reliability nonconformance wavefront arrival time data.

* * * * *